US008293241B2

(12) United States Patent
Desnoyers et al.

(10) Patent No.: US 8,293,241 B2
(45) Date of Patent: Oct. 23, 2012

(54) ANTI-FGF19 ANTIBODIES AND METHODS USING SAME

(75) Inventors: Luc Desnoyers, San Francisco, CA (US); Dorothy French, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/315,220

(22) Filed: Dec. 8, 2011

(65) Prior Publication Data

US 2012/0128675 A1 May 24, 2012

Related U.S. Application Data

(62) Division of application No. 12/913,660, filed on Oct. 27, 2010, now Pat. No. 8,241,633, which is a division of application No. 12/692,468, filed on Jan. 22, 2010, now Pat. No. 7,846,691, which is a division of application No. 11/673,411, filed on Feb. 9, 2007, now Pat. No. 7,678,373.

(60) Provisional application No. 60/772,310, filed on Feb. 10, 2006, provisional application No. 60/780,608, filed on Mar. 9, 2006, provisional application No. 60/885,866, filed on Jan. 19, 2007.

(51) Int. Cl.
*A61K 39/395* (2006.01)
(52) U.S. Cl. ............... 424/158.1; 424/141.1; 424/145.1; 424/139.1; 514/1.1; 514/19.2; 514/19.3
(58) Field of Classification Search ........................ None
See application file for complete search history.

(56) References Cited

U.S. PATENT DOCUMENTS

| | | | |
|---|---|---|---|
| 6,632,927 B2 | 10/2003 | Adair et al. |
| 7,678,373 B2 | 3/2010 | Desnoyers et al. |
| 7,846,691 B2 | 12/2010 | Desnoyers et al. |
| 2002/0012961 A1 | 1/2002 | Botstein et al. |
| 2002/0042367 A1 | 4/2002 | Stewart et al. |
| 2002/0155543 A1 | 10/2002 | Adams et al. |
| 2004/0126852 A1 | 7/2004 | Stewart et al. |
| 2004/0146908 A1 | 7/2004 | Adams et al. |
| 2005/0026243 A1 | 2/2005 | Stewart et al. |
| 2005/0026832 A1 | 2/2005 | Adams et al. |
| 2005/0196842 A1 | 9/2005 | Botstein et al. |
| 2007/0042395 A1 | 2/2007 | Botstein et al. |
| 2007/0077626 A1 | 4/2007 | Botstein et al. |
| 2007/0248604 A1 | 10/2007 | Desnoyers et al. |

FOREIGN PATENT DOCUMENTS

| | | |
|---|---|---|
| WO | WO-99/27100 A2 | 6/1999 |
| WO | WO-01/18172 A2 | 3/2001 |
| WO | WO-01-18172 A3 | 3/2001 |
| WO | WO-01/18210 A1 | 3/2001 |
| WO | WO-01/70977 A2 | 9/2001 |
| WO | WO-01/70977 A3 | 9/2001 |
| WO | WO-02/46467 A2 | 6/2002 |
| WO | WO-03/025138 A2 | 3/2003 |
| WO | WO-03/065006 A2 | 8/2003 |
| WO | WO-03/103725 A1 | 12/2003 |
| WO | WO-2007/136893 A2 | 11/2007 |

OTHER PUBLICATIONS

Abbass et al. (Apr. 1997). "Altered Expression of Fibroblast Growth Factor Receptors in Human Pituitary Adenomas," *J. Clin. Endocrinol. Metab.* 82(4):1160-1166.
Amit, A.G. et al. (Aug. 15, 1986). "Three-Dimensional Structure of an Antigen-Antibody Complex at 2.8 Å Resolution," *Science* 233(4765):747-753.
Desnoyers, L.R. et al. (Jan. 3, 2008, e-pub. Jun. 25, 2007). "Targeting FGF19 Inhibits Tumor Growth in Colon Cancer Xenograft and FGF19 Transgenic Hepatocellular Carcinoma Models," *Oncogene* 27(1):85-97.
Eswarakumar et al. (Apr. 2005). "Cellular Signaling by Fibroblast Growth Factor Receptors," *Cytokine Growth Factor Rev.* 16(2):139-149.
Fu et al. (Jun. 2004). "Fibroblast Growth Factor 19 Increases Metabolic Rate and Reverses Dietry and Leptin-Deficient Diabetes," *Endocrinology* 145(6):2594-2603.
Gutierrez et al. (Feb. 2006). "Bile Acids Decrease Hepatic Paraoxonase 1 Expression and Plasma High-Density Lipoprotein Levels via FXR-Mediated Signaling of FGFR4," *Arterioscler. Thromb. Vasc. Biol.* 26(2):301-306.
Harmer et al. (Jan. 27, 2004). "The Crystal Structure of Fibroblast Growth Factor (FGF) 19 Reveals Novel Features of the FGF Family and Offers a Structural Basis for its Unusual Receptor Affinity," *Biochemistry* 43(3):629-640.
Holt et al. (Jul. 1, 2003)."Definition of a Novel Growth Factor-Dependent Signal Cascade for the Suppression of Bile Acid Biosynthesis," *Genes Dev.* 17(13):1581-1591.
Hotzel, K.H. et al. (Sep. 2007). "Targeting FGF19 as a Therapeutic for Hepatocellular Carcinoma," Poster *presented at 14th European Cancer Conference (ECCO 14)*, Barcelona, Spain, Sep. 23-27, 2007, *EJC Supplements* 5(4):65, Abstract No. 328.
International Search Report mailed Mar. 28, 2008, for PCT Application No. PCT/US2007/061936, filed Feb. 9, 2007, six pages.
Jaakkola et al. (May 28, 1993). "Amplification of fgfr4 Gene in Human Breast and Gynecological Cancers," *Int. J. Cancer* 54(3):378-382.
Jeffers et al. (Aug. 2002). "Fibroblast Growth Factors in Cancer: Therapeutic Possibilities," *Expert Opin. Ther. Targets* 6(4):469-482.
Kan et al. (May 28, 1999). "Specificity for Fibroblast Growth Factors Determined by Heparan Sulfate in an Binary Complex with the Receptor Kinase," *J. Biol. Chem.* 274(22):15947-15952.
Kiuri-Kuhlefelt et al. (Apr. 2000). "FGF4 and INT2 Oncogenes are Amplified and Expressed in Kaposi's Sarcoma," *Mod. Pathol.* 13(4):433-437.
Morimoto et al. (Nov. 15, 2003). "Single Nucleotide Polymorphism in Fibroblast Growth Factor Receptor 4 at Codon 388 is Associated with Prognosis in High-Grade Soft Tissue Sarcoma," *Cancer* 98(10):2245-2250.

(Continued)

*Primary Examiner* — Prema Mertz
(74) *Attorney, Agent, or Firm* — Morrison & Foerster LLP

(57) ABSTRACT

The invention provides anti-FGF19 antibodies, and compositions comprising and methods of using these antibodies, methods using anti-FGF19 antibodies, and methods comprising detection of FGF19 and/or FGFR4.

18 Claims, 28 Drawing Sheets

OTHER PUBLICATIONS

Nicholes, K. et al. (Jun. 2002). "Animal Model: A Mouse Model of Hepatocellular Carcinoma, Ectopic Expression of Fibroblast Growth Factor 19 in Skeletal Muscle of Transgenic Mice," *American Journal of Pathology* 160(6):2295-2307.

Nishimura et al. (Jan. 18, 1999). "Structure and Expression of a Novel Human FGF, FGF-19, Expressed in the Fetal Brain," *Biochim. Biophys. Acta* 1444(1):148-151.

Ozawa et al. (Sep. 5, 1966). "Expression of the Fibroblast Growth Factor Family and Their Receptor Family Genes During Mouse Brain Development," *Brain Res. Mol. Brain Res.* 41(1-2):279-288.

Panka, D.J. et al. (May 1, 1988). "Variable Region Framework Differences Result in Decreased of Increased Affinity of Variant Anti-Digoxin Antibodies," *Proc. Natl. Acad. Sci. USA* 85(9):3080-3084.

Partanen et al. (Jun. 1991). "FGFR-4, a Novel Acidic Fibroblast Growth Factor Receptor with a Distinct Expression Pattern," *EMBO Journal* 10(6):1347-1354.

Penault-Llorca et al. (Apr. 10, 1995). "Expression of FGF and FGF Receptor Genes in Human Breat Cancer," *Int. J. Cancer* 61(2):170-176.

Qian et al. (Apr. 2004). "Cytoplasmic Expression of Fibroblast Growth Factor Receptor-4 in Human Pituitary Adenomas: Relation to Tumor Type, Size, Proliferation, and Invasiveness," *J. Clin. Endocrinol. Metab.* 89(4):1904-1911.

Ron et al. (Mar. 15, 1993). "Fibroblast Growth Factor Receptor 4 is a High Affinity Receptor for Both Acidic and Basic Fibroblast Growth Factor but not for Keratinocyte Growth Factor," *Journal of Biological Chemistry* 268(8):5388-5394.

Rudikoff, S. et al. (Mar. 15, 1982). "Single Amino Acid Substitution Altering Antigen-Binding Specificity," *Proc. Natl. Acad. Sci. USA* 79(6):1979-1983.

Schlessinger (Nov. 26, 2004). "Common and Distinct Elements in Cellular Signaling via EGF and FGF Receptors," *Science* 306(5701):1506-1507.

Spinola et al. (Oct. 10, 2005). "Functional FGFR4 Gly388Arg Polymorphism Predicts Prognosis in Lung Adenocarcinoma Patients," *J. Clin. Oncol.* 23(29):7307-7311.

Stark et al. (Oct. 1991). "FGFR-4, a New Member of the Fibroblast Growth Factor Receptor Family, Expressed in the Definitive Endoderm and Skeletal Muscle Lineages of the Mouse," *Development* 113(2):641-651.

Streit et al. (Aug. 20, 2004). "Involvement of the FGFR4 Arg388 Allele in Head and Neck Squamous Cell Carcinoma," *Int. J. Cancer* 111(2):213-217.

Tomlinson et al. (May 2002). "Transgenic Mice Expressing Human Fibroblast Growth Factor-19 Display Increased Metabolic Rate and Decreased Adiposity," *Endocrinology* 143(5):1741-1747.

Wang et al. (Jan. 1994). "Fibroblast Growth Factor Receptors Have Different Signaling and Mitogenic Potentials," *Molecular & Cellular Biology* 14(1):181-188.

Xie et al. (Oct. 1999). "FGF-19, a Novel Fibroblast Growth Factor with Unique Specificity for FGFR4," *Cytokine* 11(10):729-735.

Yamada et al. (Apr. 2002). "Fibroblast Growth Factor Receptor (FGFR) 4 Correlated with the Malignancy of Human Astrocytomas," *Neurol Res.* 24(3):244-248.

Yu et al. (May 19, 2000). "Elevated Cholesterol Metabolism and Bile Acid Synthesis in Mice Lacking Membrane Tyrosine Kinase Receptor FGFR4," *J. Biol. Chem.* 275(20):15482-15489.

VL Sequences

| Kabat# | 1 2 3 4 5 6 7 8 9 10 11 12 13 14 15 16 17 18 19 20 21 22 23 24 25 26 27 28 29 30 31 32 33 34 35 36 37 | mu1A6 D I K M T Q S P S S M Y A S L G E R V T I P C K A S Q D I N S F L S W F Q

| Kabat# | 38 39 40 41 42 43 44 45 46 47 48 49 50 51 52 53 54 55 56 57 58 59 60 61 62 63 64 65 66 67 68 69 70 71 72 73 74 75 76 77 78 79 80 | mu1A6 Q K P G K S P K T L I Y R A N R L V D G V P S R F S G S G S G Q D Y S L T I S S L E Y

| Kabat# | 81 82 83 84 85 86 87 88 89 90 91 92 93 94 95 96 97 98 99 100 101 102 103 104 105 106 107 108 | mu1A6 E D M G I Y Y C L Q Y D E F P L T F G A G T K V E I K R

VH Sequences

```
Kabat#  1  2  3  4  5  6  7  8  9  10 11 12 13 14 15 16 17 18 19 20 21 22 23 24 25 26 27 28 29 30 31 32 33 34 35 36 37 38 39 40 41
                                                                                        |Chothia - CDR H1|
                                                                                              |Kabat - CDR H1|
                                                                                                 |Contact - CDR H1|
mu1A6   Q  V  Q  L  K  Q  S  G  P  G  L  V  Q  P  S  Q  S  L  S  I  T  C  T  V  S  G  F  S  L  T  T  Y  G  V  H  W  V  R  Q  S  P Kabat#  42 43 44 45 46 47 48 49 50 51 52 53 54 55 56 57 58 59 60 61 62 63 64 65 66 67 68 69 70 71 72 73 74 75 76 77 78 79 80
                              |Kabat - CDR H2|
                               |Chothia - CDR H2|
                        |Contact - CDR H2|
mu1A6   G  K  G  L  E  W  L  G  V  I  W  P  G  G  G  T  D  Y  N  A  A  F  I  S  R  L  S  I  T  K  D  N  S  K  S  Q  V  F  F Kabat#  81 82 A  B  C  83 84 85 86 87 88 89 90 91 92 93 94 95 96 97 98 99 100 A  B  C  101 102 103 104 105 106 107 108 109 110 111 112 113
                                                            |Kabat - CDR H3|
                                                            |Chothia - CDR H3|
                                                            |Contact - CDR H3|
mu1A6   K  M  N  S  L  L  A  N  D  T  A  I  Y  F  C  V  R  K  E  Y  A  N  L  Y  A  M  D  Y  W  G  Q  G  T  L  L  T  V  S  A
```

FIG. 1B

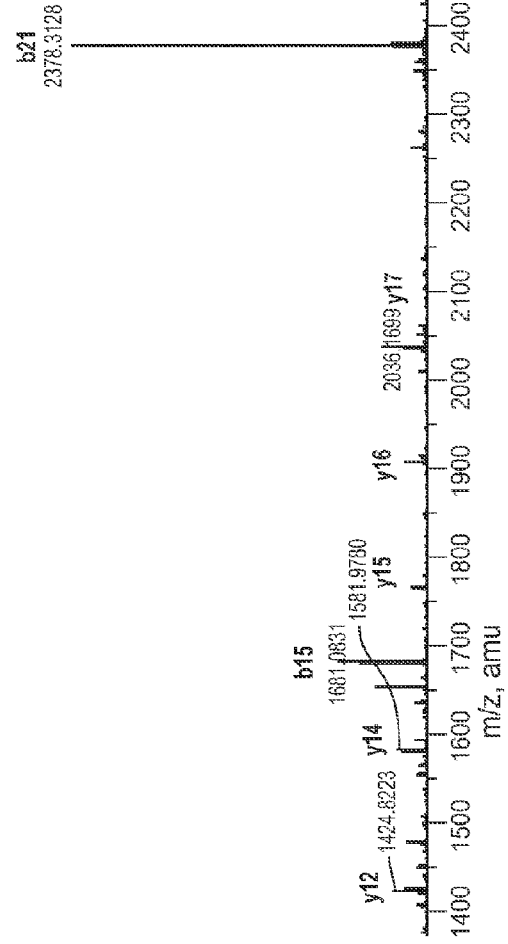

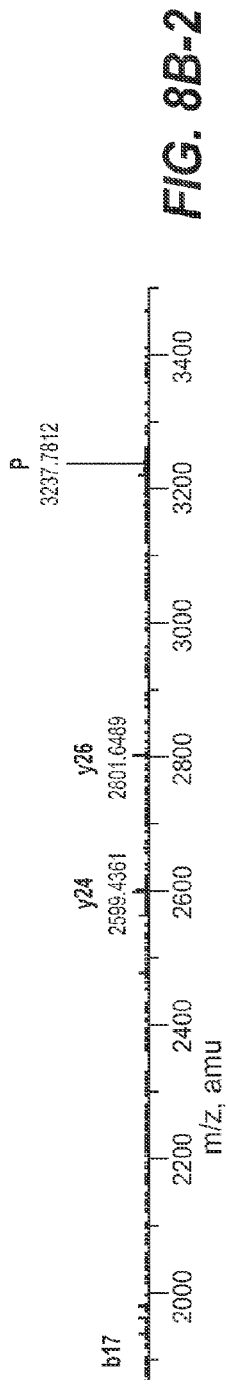

FGFR4 shRNA, HUSH-EGFP (CTRL): Stables (5 µg/ml puromycin)

SEQUENCE LISTING

```
<160> NUMBER OF SEQ ID NOS: 46

<210> SEQ ID NO 1
<211> LENGTH: 11
<212> TYPE: PRT
<213> ORGANISM: Mus musculus

<400> SEQUENCE: 1

Lys Ala Ser Gln Asp Ile Asn Ser Phe Leu Ser
                 5                  10

<210> SEQ ID NO 2
<211> LENGTH: 8
<212> TYPE: PRT
<213> ORGANISM: Mus musculus

<400> SEQUENCE: 2

Tyr Arg Ala Asn Arg Leu Val Asp
                 5

<210> SEQ ID NO 3
<211> LENGTH: 9
<212> TYPE: PRT
<213> ORGANISM: Mus musculus

<400> SEQUENCE: 3

Leu Gln Tyr Asp Glu Phe Pro Leu Thr
                 5
```

<210> SEQ ID NO 4
<211> LENGTH: 108
<212> TYPE: PRT
<213> ORGANISM: Mus musculus

<400> SEQUENCE: 4

```
Asp Ile Lys Met Thr Gln Ser Pro Ser Ser Met Tyr Ala Ser Leu
 1               5                  10                  15

Gly Glu Arg Val Thr Ile Pro Cys Lys Ala Ser Gln Asp Ile Asn
                20                  25                  30

Ser Phe Leu Ser Trp Phe Gln Gln Lys Pro Gly Lys Ser Pro Lys
                35                  40                  45

Thr Leu Ile Tyr Arg Ala Asn Arg Leu Val Asp Gly Val Pro Ser
                50                  55                  60

Arg Phe Ser Gly Ser Gly Ser Gly Gln Asp Tyr Ser Leu Thr Ile
                65                  70                  75

Ser Ser Leu Glu Tyr Glu Asp Met Gly Ile Tyr Tyr Cys Leu Gln
                80                  85                  90

Tyr Asp Glu Phe Pro Leu Thr Phe Gly Ala Gly Thr Lys Val Glu
                95                 100                 105

Ile Lys Arg
```

<210> SEQ ID NO 5
<211> LENGTH: 5
<212> TYPE: PRT
<213> ORGANISM: Mus musculus

<400> SEQUENCE: 5

```
Thr Tyr Gly Val His
                5
```

<210> SEQ ID NO 6
<211> LENGTH: 16
<212> TYPE: PRT
<213> ORGANISM: Mus musculus

<400> SEQUENCE: 6

```
Val Ile Trp Pro Gly Gly Gly Thr Asp Tyr Asn Ala Ala Phe Ile
 1               5                  10                  15

Ser
```

<210> SEQ ID NO 7
<211> LENGTH: 11
<212> TYPE: PRT
<213> ORGANISM: Mus musculus

<400> SEQUENCE: 7

```
Lys Glu Tyr Ala Asn Leu Tyr Ala Met Asp Tyr
                5                  10
```

<210> SEQ ID NO 8
<211> LENGTH: 119
<212> TYPE: PRT
<213> ORGANISM: Mus musculus

<400> SEQUENCE: 8

```
Gln Val Gln Leu Lys Gln Ser Gly Pro Gly Leu Val Gln Pro Ser
 1               5                  10                  15

Gln Ser Leu Ser Ile Thr Cys Thr Val Ser Gly Phe Ser Leu Thr
                20                  25                  30
```

```
Thr Tyr Gly Val His Trp Val Arg Gln Ser Pro Lys Gly Leu
             35                  40                  45

Glu Trp Leu Gly Val Ile Trp Pro Gly Gly Thr Asp Tyr Asn
             50                  55                  60

Ala Ala Phe Ile Ser Arg Leu Ser Ile Thr Lys Asp Asn Ser Lys
             65                  70                  75

Ser Gln Val Phe Phe Lys Met Asn Ser Leu Leu Ala Asn Asp Thr
             80                  85                  90

Ala Ile Tyr Phe Cys Val Arg Lys Glu Tyr Ala Asn Leu Tyr Ala
             95                 100                 105

Met Asp Tyr Trp Gly Gln Gly Thr Leu Leu Thr Val Ser Ala
            110                 115

<210> SEQ ID NO 9
<211> LENGTH: 23
<212> TYPE: PRT
<213> ORGANISM: Homo sapiens

<400> SEQUENCE: 9

Gly Phe Leu Pro Leu Ser His Phe Leu Pro Met Leu Pro Met Val
 1               5                  10                  15

Pro Glu Glu Pro Glu Asp Leu Arg
                 20

<210> SEQ ID NO 10
<211> LENGTH: 29
<212> TYPE: PRT
<213> ORGANISM: Homo sapiens

<400> SEQUENCE: 10

His Leu Glu Ser Asp Met Phe Ser Ser Pro Leu Glu Thr Asp Ser
 1               5                  10                  15

Met Asp Pro Phe Gly Leu Val Thr Gly Leu Glu Ala Val Arg
                 20                  25

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
ccatgatgca aaacctccaa t                                        21

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
acccagacag cgctctttga                                          20

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13
```
tgtcatgaga cctccgggcc ttcc                                              24

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
aatttgccgt gagtggagtc                                                   20

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
cagtggcaaa gtggagattg t                                                 21

<210> SEQ ID NO 16
<211> LENGTH: 26
<212> TYPE: DNA
<213> ORGANISM: Artificial Sequence
<220> FEATURE:
<223> OTHER INFORMATION: Synthetic Construct

<400> SEQUENCE: 16
ccatcaacga ccccttcatt gacctc                                            26

<210> SEQ ID NO 17
<211> LENGTH: 23
<212> TYPE: DNA
<213> ORGANISM: Artificial Sequence
<220> FEATURE:
<223> OTHER INFORMATION: Synthetic Construct

<400> SEQUENCE: 17
agaccccaag tcttgtcaat aac                                               23

<210> SEQ ID NO 18
<211> LENGTH: 24
<212> TYPE: DNA
<213> ORGANISM: Artificial Sequence
<220> FEATURE:
<223> OTHER INFORMATION: Synthetic Construct

<400> SEQUENCE: 18
aatatcatgt tggaaaacca agtg                                              24

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
ccgctgcttc cacacagcaa                                                   20

<210> SEQ ID NO 20
<211> LENGTH: 18
<212> TYPE: DNA
<213> ORGANISM: Artificial Sequence
<220> FEATURE:

<223> OTHER INFORMATION: Synthetic Construct

<400> SEQUENCE: 20
gctcttgacg ggagcatt                                             18

<210> SEQ ID NO 21
<211> LENGTH: 18
<212> TYPE: DNA
<213> ORGANISM: Artificial Sequence
<220> FEATURE:
<223> OTHER INFORMATION: Synthetic Construct

<400> SEQUENCE: 21
cgccatttgc tcctgttt                                             18

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct

<400> SEQUENCE: 22
gcaggcttcc agcttctc                                             18

<210> SEQ ID NO 23
<211> LENGTH: 19
<212> TYPE: DNA
<213> ORGANISM: Artificial Sequence
<220> FEATURE:
<223> OTHER INFORMATION: Synthetic Construct

<400> SEQUENCE: 23
agcggattct catggaaca                                            19

<210> SEQ ID NO 24
<211> LENGTH: 18
<212> TYPE: DNA
<213> ORGANISM: Artificial Sequence
<220> FEATURE:
<223> OTHER INFORMATION: Synthetic Construct

<400> SEQUENCE: 24
ctggtcagcc aggagctt                                             18

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
tccacaagct gaaggcagac aagg                                      24

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
gctgctcctg gtgaacaagc                                           20

<210> SEQ ID NO 27

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
tgttcaatga aatcgtgcgg                                               20

<210> SEQ ID NO 28
<211> LENGTH: 24
<212> TYPE: DNA
<213> ORGANISM: Artificial Sequence
<220> FEATURE:
<223> OTHER INFORMATION: Synthetic Construct

<400> SEQUENCE: 28
caagtggaac ctggccgcaa  tgac                                         24

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
gaaaaatggt cgctacagca  tct                                          23

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
ggtgctattg aaagccttgc  a                                            21

<210> SEQ ID NO 31
<211> LENGTH: 19
<212> TYPE: DNA
<213> ORGANISM: Artificial Sequence
<220> FEATURE:
<223> OTHER INFORMATION: Synthetic Construct

<400> SEQUENCE: 31
cggacggagg ccgctgacc                                                19

<210> SEQ ID NO 32
<211> LENGTH: 20
<212> TYPE: DNA
<213> ORGANISM: Artificial Sequence
<220> FEATURE:
<223> OTHER INFORMATION: Synthetic Construct

<400> SEQUENCE: 32
gacttgagcc agctgcacag                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Construct

<400> SEQUENCE: 33
```

```
gttggtgcaa cgtcgttacg                                                    20

<210> SEQ ID NO 34
<211> LENGTH: 22
<212> TYPE: DNA
<213> ORGANISM: Artificial Sequence
<220> FEATURE:
<223> OTHER INFORMATION: Synthetic Construct

<400> SEQUENCE: 34
cctggacgct cggcctgaag tg                                                 22

<210> SEQ ID NO 35
<211> LENGTH: 21
<212> TYPE: DNA
<213> ORGANISM: Artificial Sequence
<220> FEATURE:
<223> OTHER INFORMATION: Synthetic Construct

<400> SEQUENCE: 35
cgttaacagt gggtgccaac t                                                  21

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
cccgacggtc tctcttcaaa                                                    20

<210> SEQ ID NO 37
<211> LENGTH: 24
<212> TYPE: DNA
<213> ORGANISM: Artificial Sequence
<220> FEATURE:
<223> OTHER INFORMATION: Synthetic Construct

<400> SEQUENCE: 37
atgctaacgc agcagttgca aaca                                               24

<210> SEQ ID NO 38
<211> LENGTH: 19
<212> TYPE: DNA
<213> ORGANISM: Artificial Sequence
<220> FEATURE:
<223> OTHER INFORMATION: Synthetic Construct

<400> SEQUENCE: 38
agcggattct catggaaca                                                     19

<210> SEQ ID NO 39
<211> LENGTH: 18
<212> TYPE: DNA
<213> ORGANISM: Artificial Sequence
<220> FEATURE:
<223> OTHER INFORMATION: Synthetic Construct

<400> SEQUENCE: 39
ctggtcagcc aggagctt                                                      18

<210> SEQ ID NO 40
<211> LENGTH: 24
<212> TYPE: DNA
<213> ORGANISM: Artificial Sequence
<220> FEATURE:
```

<223> OTHER INFORMATION: Synthetic Construct

<400> SEQUENCE: 40
tccacaagct gaaggcagac aagg        24

<210> SEQ ID NO 41
<211> LENGTH: 65
<212> TYPE: DNA
<213> ORGANISM: Artificial Sequence
<220> FEATURE:
<223> OTHER INFORMATION: Synthetic Construct

<400> SEQUENCE: 41
gatcccccct cgtgagtcta gatctattca agagatagat ctagactcac        50
gaggtttttt ggaaa        65

<210> SEQ ID NO 42
<211> LENGTH: 65
<212> TYPE: DNA
<213> ORGANISM: Artificial Sequence
<220> FEATURE:
<223> OTHER INFORMATION: Synthetic Construct

<400> SEQUENCE: 42
agcttttcca aaaaacctcg tgagtctaga tctatctctt gaatagatct        50
agactcacga ggggg        65

<210> SEQ ID NO 43
<211> LENGTH: 65
<212> TYPE: DNA
<213> ORGANISM: Artificial Sequence
<220> FEATURE:
<223> OTHER INFORMATION: Synthetic Construct

<400> SEQUENCE: 43
gatccccgaa ccgcattgga ggcattatca agagaaatgc ctccaatgcg        50
gttctttttt ggaaa        65

<210> SEQ ID NO 44
<211> LENGTH: 65
<212> TYPE: DNA
<213> ORGANISM: Artificial Sequence
<220> FEATURE:
<223> OTHER INFORMATION: Synthetic Construct

<400> SEQUENCE: 44
agcttttcca aaaagaacc gcattggagg catttctctt gataatgcct        50
ccaatgcggt tcggg        65

<210> SEQ ID NO 45
<211> LENGTH: 65
<212> TYPE: DNA
<213> ORGANISM: Artificial Sequence
<220> FEATURE:
<223> OTHER INFORMATION: Synthetic Construct

<400> SEQUENCE: 45
gatccccgca gcacgacttc ttcaagttca agagacttga agaagtcgtg        50
ctgctttttt ggaaa        65

<210> SEQ ID NO 46
<211> LENGTH: 65
<212> TYPE: DNA

```
<213> ORGANISM: Artificial Sequence
<220> FEATURE:
<223> OTHER INFORMATION: Synthetic Construct

<400> SEQUENCE: 46
agcttttcca aaaaagcagc acgacttctt caagtctctt gaacttgaag          50
aagtcgtgct gcggg                                                65
```

ANTI-FGF19 ANTIBODIES AND METHODS USING SAME

CROSS-REFERENCE TO RELATED APPLICATIONS

This application is a divisional of U.S. application Ser. No. 12/913,660 filed Oct. 27, 2010, which is a divisional of U.S. application Ser. No. 12/692,468, filed on Jan. 22, 2010, which is a divisional of U.S. application Ser. No. 11/673,411, filed on Feb. 9, 2007 and issued as U.S. Pat. No. 7,678,373, which claims priority under 35 USC §119 to U.S. Provisional Application No. 60/772,310, filed Feb. 10, 2006, U.S. Provisional Application No. 60/780,608, filed Mar. 9, 2006, and U.S. Provisional Application No. 60/885,866, filed Jan. 19, 2007, the entire contents of which are hereby incorporated by reference.

FIELD OF THE INVENTION

The present invention relates generally to the fields of molecular biology. More specifically, the invention concerns anti-FGF19 antibodies, uses of same, and detection of FGF19 and/or FGFR4.

BACKGROUND OF THE INVENTION

The fibroblast growth factor (FGF) family is composed of 22 structurally related polypeptides that bind to 4 receptor tyrosine kinases (FGFR1-4) and one kinase deficient receptor (FGFR5) (Eswarakumar et at (2005) Cytokine Growth Factor Rev 16, 139-149; Ornitz et at (2001) Genome Biol 2, REVIEWS3005; Sleeman et at (2001) Gene 271, 171-182). FGFs' interaction with FGFR1-4 results in receptor homodimerization and autophosphorylation, recruitment of cytosolic adaptors such as FRS2 and initiation of multiple signaling pathways (Powers et al (2000) Endocr Relat Cancer 7, 165-197; Schlessinger, J. (2004) Science 306, 1506-1507).

FGFs and FGFRs play important roles in development and tissue repair by regulating cell proliferation, migration, chemotaxis, differentiation, morphogenesis and angiogenesis (Ornitz et al (2001) Genome Biol 2, REVIEWS3005; Auguste et al (2003) Cell Tissue Res 314, 157-166; Steiling et al (2003) Curr Opin Biotechnol 14, 533-537). Several FGFs and FGFRs are associated with the pathogenesis of breast, prostate, cervix, stomach and colon cancers (Jeffers et al (2002) Expert Opin Ther Targets 6, 469-482; Mattila et al. (2001) Oncogene 20, 2791-2804; Ruohola et al. (2001) Cancer Res 61, 4229-4237; Marsh et al (1999) Oncogene 18, 1053-1060; Shimokawa et al (2003) Cancer Res 63, 6116-6120; Jang (2001) Cancer Res 61, 3541-3543; Cappellen (1999) Nat Genet. 23, 18-20; Gowardhan (2005) Br J Cancer 92, 320-327).

FGF19 is a member of the most distant of the seven subfamilies of the FGFs. FGF19 is a high affinity ligand of FGFR4 (Xie et al (1999) Cytokine 11:729-735). FGF19 is normally secreted by the biliary and intestinal epithelium. FGF19 plays a role in cholesterol homeostasis by repressing hepatic expression of cholesterol-7-α-hydroxylase 1 (Cyp7α1), the rate-limiting enzyme for cholesterol and bile acid synthesis (Gutierrez et al (2006) Arterioscler Thromb Vasc Biol 26, 301-306; Yu et al (2000) J Biol Chem 275, 15482-15489; Holt, J A, et al. (2003) Genes Dev 17(130): 158). FGF19 ectopic expression in a transgenic mouse model increases hepatocytes proliferation, promotes hepatocellular dysplasia and results in neoplasia by 10 months of age (Nicholes et al. (2002). Am J Pathol 160, 2295-2307). The mechanism of FGF19 induced hepatocellular carcinoma is thought to involve FGFR4 interaction. Treatment with FGF-19 increases metabolic rate and reverses dietary and leptin-deficient diabetes. Fu et al (2004) 145:2594-2603. FGF-19 is also described in, for example, Xie et al. (1999) Cytokine 11:729-735; and Harmer et al (2004) 43:629-640.

FGFR4 expression is widely distributed and was reported in developing skeletal muscles, liver, lung, pancreas, adrenal, kidney and brain (Kan et al. (1999) J Biol Chem 274, 15947-15952; Nicholes et al. (2002). Am J Pathol 160, 2295-2307; Ozawa et al. (1996) Brain Res Mol Brain Res 41, 279-288; Stark et al (1991) Development 113, 641-651). FGFR4 amplification was reported in mammary and ovarian adenocarcinomas (Jaakkola et al (1993) Int J Cancer 54, 378-382). FGFR4 mutation and truncation were correlated with the malignancy and in some cases the prognosis of prostate and lung adenocarcinomas, head and neck squamous cell carcinoma, soft tissue sarcoma, astrocytoma and pituitary adenomas (Jaakkola et al (1993) Int J Cancer 54, 378-382; Morimoto (2003) Cancer 98, 2245-2250; Qian (2004) J Clin Endocrinol Metab 89, 1904-1911; Spinola et al. (2005) J Clin Oncol 23, 7307-7311; Streit et al (2004) Int J Cancer 111, 213-217; Wang (1994) Mol Cell Biol 14, 181-188; Yamada (2002) Neurol Res 24, 244-248).

It is clear that there continues to be a need for agents that have clinical attributes that are optimal for development as therapeutic agents. The invention described herein meets this need and provides other benefits.

All references cited herein, including patent applications and publications, are incorporated by reference in their entirety.

SUMMARY OF THE INVENTION

The invention is in part based on the identification of a variety of FGF19 binding agents (such as antibodies, and fragments thereof). FGF19 presents as an important and advantageous therapeutic target, and the invention provides compositions and methods based on binding FGF19. FGF19 binding agents, as described herein, provide important therapeutic and diagnostic agents for use in targeting pathological conditions associated with expression and/or activity of the FGF19-FGFR4 pathways. Accordingly, the invention provides methods, compositions, kits and articles of manufacture related to FGF19 binding and detection of FGF19 and/or FGFR4 binding.

In one aspect, the invention provides an isolated anti-FGF19 antibody, wherein a full length IgG form of the antibody specifically binds human FGF19 with a binding affinity of about 20 pM or better. In some embodiments, the antibody specifically binds human FGF19 with a binding affinity of about 40 pM or better. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA) and ELISA.

In one aspect, the invention provides an isolated anti-FGF19 antibody, wherein a full length IgG form of the antibody specifically binds human FGF19 with a $k_{on}$ of $6\times10^5$ $(M^{-1}s^{-1})$ or better and/or with a K, of $5\times10^{-6}$ $(s^{-1})$ or better.

In one aspect, the invention provides an isolated antibody that binds an FGFR4 binding region of FGF19.

In one aspect, the invention provides an isolated antibody that bind a peptide comprising, consisting essentially of or consisting of the following amino acid sequence: GFLPLSH-FLPMLPMVPEEPEDLR (SEQ ID NO:9) or HLESDMFSS-PLETDSMDPFGLVTGLEAVR (SEQ. ID NO:10).

In some embodiments, the isolated antibody binds a polypeptide comprising, consisting essentially of or consisting of amino acid numbers 160-217, 140-159, G133-R155, G156-R180 and/or A183-G192 of the mature human FGF19 amino acid sequence (i.e., lacking the signal peptide). In some embodiments, the isolated antibody binds a polypeptide comprising, consisting essentially of, or consisting of amino acid numbers P41-Y47, P41-F58, P51-F58, E81-R88, E124-N132 and/or H164-P171 of the mature human FGF19 amino acid sequence (i.e., lacking the signal peptide).

In one aspect, the invention provides an anti-FGF19 antibody comprising: at least one, two, three, four, five, and/or six hypervariable region (HVR) sequences selected from the group consisting of: KASQDINSFLS (SEQ ID NO:1), YRANRLVD (SEQ ID NO:2), LQYDEFPLT (SEQ ID NO:3), TYGVH (SEQ ID NO:5), VIWPGGGTDYNAAFIS (SEQ ID NO:6), and KEYANLYAMDY (SEQ ID NO:7).

In one aspect, the invention provides an anti-FGF19 antibody comprising: at least one, two, three, four, five, and/or six hypervariable region (HVR) sequences selected from the group consisting of: (a) HVR-L1 comprising sequence KASQDINSFLS (SEQ ID NO:1); (b) HVR-L2 comprising sequence YRANRLVD (SEQ ID NO:2); (c) HVR-L3 comprising sequence LQYDEFPLT (SEQ ID NO:3); (d) HVR-H1 comprising sequence TYGVH (SEQ ID NO:5); (e) HVR-H2 comprising sequence VIWPGGGTDYNAAFIS (SEQ ID NO:6); and (f) HVR-H3 comprising sequence KEYANLYAMDY (SEQ ID NO:7).

In one aspect, the invention provides an anti-FGF19 antibody comprising a light chain comprising (a) HVR-L1 comprising sequence KASQDINSFLS (SEQ ID NO:1); (b) HVR-L2 comprising sequence YRANRLVD (SEQ ID NO:2); and (c) HVR-L3 comprising sequence LQYDEFPLT (SEQ ID NO:3).

In one aspect, the invention provides an anti-FGF19 antibody comprising a heavy chain comprising
(a) HVR-H1 comprising sequence TYGVH (SEQ ID NO:5); (b) HVR-H2 comprising sequence VIWPGGGTDY-NAAFIS (SEQ ID NO:6); and (c) HVR-H3 comprising sequence KEYANLYAMDY (SEQ ID NO:7).

In one aspect, the invention provides an anti-FGF19 antibody comprising (a) a light chain comprising (i) HVR-L1 comprising sequence KASQDINSFLS (SEQ ID NO:1); (ii) HVR-L2 comprising sequence YRANRLVD (SEQ ID NO:2); and (iii) HVR-L3 comprising sequence LQYDEFPLT (SEQ ID NO:3); and (b) a heavy chain comprising (i) HVR-H1 comprising sequence TYGVH (SEQ ID NO:5); (ii) HVR-H2 comprising sequence VIWPGGGTDYNAAFIS (SEQ ID NO:6); and (iii) HVR-H3 comprising sequence KEYANLYAMDY (SEQ ID NO:7).

In one embodiment, an antibody of the invention comprises a light chain variable domain having the sequence:
DIKMTQSPSSMYASLGERVTIPCKASQ-DINSFLSWFQQKPGKSPKTLIYRANR-LVDGVPSRFSGSGSGQDYSL TISSLEYEDMGIYY-CLQYDEFPLTFGAGTKVEIKR (SEQ ID NO:4); and comprises a heavy chain variable domain having the sequence:

```
                                        (SEQ ID NO: 8)
QVQLKQSGPGLVQPSQSLSITCTVSGFSLTTYGVHWVRQSPGKGLEWL

GVIWPGGGTDYNAAFISRLSITKDNSKSQVFFKMNSLLANDTAIYFCV

RKEYANLYAMDYWGQGTLLTVSA.
```

In one embodiment, an antibody of the invention comprises a light chain comprising at least one, at least two or all three of HVR sequences selected from the group consisting of KASQDINSFLS (SEQ ID NO:1); YRANRLVD (SEQ ID NO:2); and LQYDEFPLT (SEQ ID NO:3).

In one embodiment, the antibody comprises light chain HVR-L1 having amino acid sequence KASQDINSFLS (SEQ ID NO:1). In one embodiment, the antibody comprises light chain HVR-L2 having amino acid sequence YRANRLVD (SEQ ID NO:2). In one embodiment, the antibody comprises light chain HVR-L3 having amino acid sequence LQYDEFPLT (SEQ ID NO:3).

In one embodiment, an antibody of the invention comprises a heavy chain comprising at least one, at least two or all three of HVR sequences selected from the group consisting of TYGVH (SEQ ID NO:5); (e) VIWPGGGTDYNAAFIS (SEQ ID NO:6); and KEYANLYAMDY (SEQ ID NO:7).

In one embodiment, the antibody comprises heavy chain HVR-H1 having amino acid sequence TYGVH (SEQ ID NO:5). In one embodiment, the antibody comprises heavy chain HVR-H2 having amino acid sequence VIWPGGGT-DYNAAFIS (SEQ ID NO:6). In one embodiment, the antibody comprises heavy chain HVR-H3 having amino acid sequence KEYANLYAMDY (SEQ ID NO:7).

In one embodiment, an antibody of the invention comprises a heavy chain comprising at least one, at least two or all three of HVR sequences selected from the group consisting of TYGVH (SEQ ID NO:5); (e) VIWPGGGTDYNAAFIS (SEQ ID NO:6); and KEYANLYAMDY (SEQ ID NO:7) and a light chain comprising at least one, at least two or all three of HVR sequences selected from the group consisting of KASQDINSFLS (SEQ ID NO: 1); YRANRLVD (SEQ ID NO:2); and LQYDEFPLT (SEQ ID NO:3).

In one embodiment, an antibody of the invention comprises a light chain variable domain having the sequence:

```
                                        (SEQ ID NO: 4)
DIKMTQSPSSMYASLGERVTIPCKASQDINSFLSWFQQKPGKSPKTLI

YRANRLVDGVPSRFSGSGSGQDYSLTISSLEYEDMGIYYCLQYDEFPL

TFGAGTKVEIKR.
```

In one embodiment, an antibody of the invention comprises a heavy chain variable domain having the sequence:

```
                                        (SEQ ID NO: 8)
QVQLKQSGPGLVQPSQSLSITCTVSGFSLTTYGVHWVRQSPGKGLEWL

GVIWPGGGTDYNAAFISRLSITKDNSKSQVFFICMNSLLANDTAIYFC

VRKEYANLYAMDYWGQGILLTVSA.
```

In another aspect, the invention provides anti-FGF19 monoclonal antibodies that compete with an antibody comprising a light chain variable domain having the sequence:
DIKMTQSPSSMYASLGERVTIPCKASQ-DINSFLSWFQQKPGKSPKTLIYRANR-LVDGVPSRFSGSGSGQDYSL TISSLEYEDMGIYY-CLQYDEFPLTFGAGTKVEIKR (SEQ ID NO:4) and a heavy chain variable domain having the sequence:

```
                                                      (SEQ ID NO: 8)
QVQLKQSGPGLVQPSQSLSITCTVSGFSLTTYGVHWVRQSPGKGLEWL

GVIWPGGGTDYNAAFISRLSITKDNSKSQVFFKMNSLLANDTAIYFCV

RKEYANLYAMDYWGQGTLLTVSA
for binding to FGF19.
```

In another aspect, the invention provides anti-FGF19 monoclonal antibodies that bind the same (or a substantially similar) FGF19 epitope as an antibody comprising a light chain variable domain having the sequence: DIKMTQSPSSMYASLGERVTIPCKASQ-DINSFLSWFQQKPGKSPKTLIYRANR-LVDGVPSRFSGSGSGQDYSL TISSLEYEDMGIYY-CLQYDEFPLTFGAGTKVEIKR (SEQ ID NO:4) and a heavy chain variable domain having the sequence:

```
                                                      (SEQ ID NO: 8)
QVQLKQSGPGLVQPSQSLSITCTVSGFSLTTYGVHWVRQSPGKGLEWL

GVIWPGGGTDYNAAFISRLSITKDNSKSQVFFKMNSLLANDTAIYFCV

RKEYANLYAMDYWGQGTLLTVSA.
```

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below).

In some embodiments, the antibody is a monoclonal antibody. In some embodiments, the antibody is a polyclonal antibody. In some embodiments, the antibody is selected from the group consisting of a chimeric antibody, an affinity matured antibody, a humanized antibody, and a human antibody. In some embodiments, the antibody is an antibody fragment. In some embodiments, the antibody is a Fab, Fab', Fab'-SH, F(ab')$_2$, or scFv.

In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g. obtained by mutagenesis (e.g., phage display screening, etc.). In one embodiment, a chimeric antibody of the invention has murine V regions and human C region. In one embodiment, the murine light chain V region is fused to a human kappa light chain. In one embodiment, the murine heavy chain V region is fused to a human IgG1 C region.

Humanized antibodies of the invention include those that have amino acid substitutions in the FR and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g. decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA. In some embodiments, the antibodies of the invention is of the IgG class (e.g., IgG1 or IgG4) and comprises at least one mutation in E233, L234, L235, G236, D265, D270, N297, E318, K320, K322, A327, A330, P331 and/or P329 (numbering according to the EU index). In some embodiments, the antibodies comprise the mutation L234A/L235A or D265A/N297A.

In one aspect, the invention provides anti-FGF19 polypeptides comprising any of the antigen binding sequences provided herein, wherein the anti-FGF19 polypeptides specifically bind to FGF19.

In one aspect, the invention provides an immunoconjugate (interchangeably termed "antibody drug conjugate" or "ADC") comprising any of the anti-FGF19 antibodies disclosed herein conjugated to an agent, such as a drug.

The antibodies of the invention bind FGF19, and in some embodiments, may modulate one or more aspects of FGF19-associated effects, including but not limited to FGFR4 activation, FGFR4 downstream molecular signaling, disruption of FGFR4 binding to FGF19, FGFR4 multimerization, expression of a CYP7α1 gene, phosphorylation of FGFR4, MAPK, FRS2 and/or ERK2, activation of β-catenin, FGF19-promoted cell migration, and/or disruption of any biologically relevant FGF19 and/or FGFR4 biological pathway, and/or treatment and/or prevention of a tumor, cell proliferative disorder or a cancer; and/or treatment or prevention of a disorder associated with FGF19 expression and/or activity (such as increased FGF19 expression and/or activity). In some embodiments, the antibody of the invention specifically binds to FGF19. In some embodiments, the antibody specifically binds to an FGFR4 binding region of FGF19. In some embodiments, the antibody specifically binds FGF19 with a Kd of about 20 pM or stronger. In some embodiments, the antibody specifically binds FGF19 with a Kd of about 40 nM or stronger. In some embodiments, the antibody of the invention reduces, inhibits, and/or blocks FGF19 activity in vivo and/or in vitro. In some embodiments, the antibody competes for binding with FGFR4 (reduces and/or blocks FGFR4 binding to FGF19).

In one aspect, the invention provides an isolated anti-FGF19 antibody that inhibits, reduces, and/or blocks FGF19-induced repression of expression of a CYP7α1 gene in a cell exposed to FGF19.

In one aspect, the invention provides an isolated anti-FGF19 antibody that inhibits, reduces, and/or blocks FGF19-induced phosphorylation of FGFR4, MAPK, FRS2 and/or ERK2 in a cell exposed to FGF19.

In one aspect, the invention provides an isolated anti-FGF19 antibody that inhibits, reduces, and/or blocks FGF19-promoted cell migration. In some embodiments, the cell is a tumor cell. In some embodiments, the cell is a tumor cell. In some embodiments, the cell is an HCT116 cell.

In one aspect, the invention provides an isolated anti-FGF19 antibody that inhibits, reduces, and/or blocks Wnt pathway activation in a cell. In some embodiments, Wnt pathway activation comprises one or more of β-catenin immunoreactivity, tyrosine phosphorylation of β-catenin, expression of Wnt target genes, β-catenin mutation, and E-cadherin binding to β-catenin. Detection of Wnt pathway activation is known in the art, and some examples are described and exemplified herein.

In one aspect, the invention provides compositions comprising one or more antibodies of the invention and a carrier. In one embodiment, the carrier is pharmaceutically acceptable.

In another aspect, the invention supplies a composition comprising one or more anti-FGF19 antibodies described herein, and a carrier. This composition may further comprise a second medicament, wherein the antibody is a first medicament. This second medicament, for cancer treatment, for example, may be another antibody, chemotherapeutic agent, cytotoxic agent, anti-angiogenic agent, immunosuppressive agent, prodrug, cytokine, cytokine antagonist, cytotoxic radiotherapy, corticosteroid, anti-emetic cancer vaccine, analgesic, anti-vascular agent, or growth-inhibitory agent. In another embodiment, a second medicament is administered to the subject in an effective amount, wherein the antibody is a first medicament. This second medicament is more than one medicament, and is preferably another antibody, chemotherapeutic agent, cytotoxic agent, anti-angiogenic agent, immunosuppressive agent, prodrug, cytokine, cytokine antagonist, cytotoxic radiotherapy, corticosteroid, anti-emetic, cancer vaccine, analgesic, anti-vascular agent, or growth-inhibitory agent. More specific agents include, for example, irinotecan (CAMPTOSAR®), cetuximab (ERBITUX®), fulvestrant (FASLODEX®), vinorelbine (NAVELBINE®), EFG-receptor antagonists such as erlotinib (TARCEVA®) VEGF antagonists such as bevacizumab (AVASTIN®), vincristine (ONCOVIN®), inhibitors of mTor (a serine/threonine protein kinase) such as rapamycin and CCI-779, and anti-HER1, HER2, ErbB, and/or EGFR antagonists such as trastuzumab (HERCEPTIN®), pertuzumab (OMNITARG™), or lapatinib, and other cytotoxic agents including chemotherapeutic agents. In some embodiments, the second medicament is an anti-estrogen drug such as tamoxifen, fulvestrant, or an aromatase inhibitor, an antagonist to vascular endothelial growth factor (VEGF) or to ErbB or the Efb receptor, or Her-1 or Her-2. In some embodiments, the second medicament is tamoxifen, letrozole, exemestane, anastrozole, irinotecan, cetuximab, fulvestrant, vinorelbine, erlotinib, bevacizumab, vincristine, imatinib, sorafenib, lapatinib, or trastuzumab, and preferably, the second medicament is erlotinib, bevacizumab, or trastuzumab.

In one aspect, the invention provides an anti-idiotype antibody that specifically binds an anti-FGF19 antibody of the invention.

In one aspect, the invention provides nucleic acids encoding an anti-FGF19 antibody of the invention.

In one aspect, the invention provides vectors comprising a nucleic acid of the invention.

In one aspect, the invention provides compositions comprising one or more nucleic acid of the invention and a carrier. In one embodiment, the carrier is pharmaceutically acceptable.

In one aspect, the invention provides host cells comprising a nucleic acid or a vector of the invention. A vector can be of any type, for example a recombinant vector such as an expression vector. Any of a variety of host cells can be used. In one embodiment, a host cell is a prokaryotic cell, for example, *E. coli*. In one embodiment, a host cell is a eukaryotic cell, for example a mammalian cell such as Chinese Hamster Ovary (CHO) cell.

In one aspect, the invention provides methods of making an antibody of the invention. For example, the invention provides methods of making an anti-FGF19 antibody (which, as defined herein includes full length and fragments thereof), said method comprising expressing in a suitable host cell a recombinant vector of the invention encoding said antibody, and recovering said antibody.

In one aspect, the invention provides an article of manufacture comprising a container; and a composition contained within the container, wherein the composition comprises one or more anti-FGF19 antibodies of the invention. In one embodiment, the composition comprises a nucleic acid of the invention. In one embodiment, a composition comprising an antibody further comprises a carrier, which in some embodiments is pharmaceutically acceptable. In one embodiment, an article of manufacture of the invention further comprises instructions for administering the composition (for e.g., the antibody) to an individual (such as instructions for any of the methods described herein).

In one aspect, the invention provides a kit comprising a first container comprising a composition comprising one or more anti-FGF19 antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In one embodiment, a kit further comprises instructions for administering the composition (for e.g., the antibody) to an individual.

In one aspect, the invention provides use of an anti-FGF19 antibody of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a nucleic acid of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of an expression vector of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a host cell of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of an article of manufacture of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

In one aspect, the invention provides use of a kit of the invention in the preparation of a medicament for the therapeutic and/or prophylactic treatment of a disorder, such as a cancer, a tumor, and/or a cell proliferative disorder. In some embodiments, the cancer, a tumor, and/or a cell proliferative disorder is colorectal cancer, hepatocellular carcinoma, lung cancer, breast cancer, or pancreatic cancer. In some embodiments, the disorder is a liver disorder, such as cirrhosis. In some embodiments, the disorder is a wasting disorder.

The invention provides methods and compositions useful for modulating disease states associated with expression and/or activity of FGF19 and/or FGFR4, such as increased expression and/or activity or undesired expression and/or activity, said methods comprising administration of an effective dose of an anti-FGF19 antibody to an individual in need of such treatment.

In one aspect, the invention provides methods for killing a cell (such as a cancer or tumor cell), the methods comprising administering an effective amount of an anti-FGF19 antibody to an individual in need of such treatment.

In one aspect, the invention provides methods for reducing, inhibiting, blocking, or preventing growth of a tumor or cancer, the methods comprising administering an effective amount of an anti-FGF19 antibody to an individual in need of such treatment.

Methods of the invention can be used to affect any suitable pathological state. Exemplary disorders are described herein, and include a cancer selected from the group consisting of esophageal cancer, bladder cancer, lung cancer, ovarian cancer, pancreatic cancer, mammary fibroadenoma, prostate cancer, head and neck squamous cell carcinoma, soft tissue sarcoma, astrocytoma, pituitary cancer, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell, a colon cancer cell, a pancreatic cancer cell, an ovarian cancer cell, a cervical cancer cell, a central nervous system cancer cell, an esophageal cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, a leukemia cell, a brain cancer cell, a endometrial cancer cell, a testis cancer cell, a cholangiocarcinoma cell, a gallbladder carcinoma cell, a lung cancer cell, and/or a prostate cancer cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell.

In one embodiment of the invention, the cell that is targeted is a cirrhotic liver cell.

Methods of the invention can further comprise additional treatment steps. For example, in one embodiment, a method further comprises a step wherein a targeted cell and/or tissue (for e.g., a cancer cell) is exposed to radiation treatment or a chemotherapeutic agent.

Any suitable anti-FGF19 antibody may be used for methods involving treatment and/or prevention of a disorder, including monoclonal and/or polyclonal antibodies, a human antibody, a chimeric antibody, an affinity-matured antibody, a humanized antibody, and/or an antibody fragment. In some embodiments, the anti-FGF19 antibody is any of the anti-FGF19 antibodies described herein.

In another aspect, the invention provides a complex of any of the anti-FGF19 antibodies described herein and FGF19. In some embodiments, the complex is in vivo or in vitro. In some embodiments, the anti-FGF19 antibody is detectably labeled.

In another aspect, the invention provides methods for detection of FGF19, the methods comprising detecting FGF19-anti-FGF19 antibody complex in a biological sample. The term "detection" as used herein includes qualitative and/or quantitative detection (measuring levels) with or without reference to a control.

In another aspect, the invention provides methods for detecting a disorder associated with FGF19 expression and/or activity, the methods comprising detecting FGF19 in a biological sample from an individual. In some embodiments, the FGF19 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for diagnosing a disorder associated with FGFR4 expression and/or activity, the methods comprising detecting FGFR4 in a biological sample from an individual. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for diagnosing a disorder associated with FGFR4 and FGF19 expression and/or activity, the methods comprising detecting FGFR4 and FGF19 in a biological sample from an individual. In some embodiments, the FGF19 expression is increased expression or abnormal expression. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor. In some embodiments, expression of FGFR4 is detected in a first biological sample, and expression of FGF19 is detected in a second biological sample.

In another aspect, the invention provides methods for selecting treatment for an individual, the methods comprising: (a) detecting FGF19 expression, if any, in an individual's biological sample; and (b) subsequence to step (a), selecting treatment for the individual, wherein the selection of treatment is based on the FGF19 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, FGF19 expression is detected and treatment with an anti-FGF19 antibody is selected. In some embodiments, the individual has a tumor, cancer, and/or a cell proliferative disorder, such as colorectal cancer, lung cancer, hepatocellular carcinoma, breast cancer and/or pancreatic cancer.

In another aspect, the invention provides methods for selecting treatment for an individual, the methods comprising: (a) detecting FGFR4 expression, if any, in an individual's biological sample; and (b) subsequence to step (a), selecting treatment for the individual, wherein the selection of treatment is based on the FGFR4 expression detected in step (a). In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 expression is detected and treatment with an anti-FGF19 antibody is selected. In some embodiments, the individual has a tumor, cancer, and/or a cell proliferative disorder, such as colorectal cancer, lung cancer, hepatocellular carcinoma, breast cancer and/or pancreatic cancer.

In another aspect, the invention provides methods for selecting treatment for an individual, the methods comprising: (a) detecting FGF19 and FGFR4 expression, if any, in an individual's biological sample; and (b) subsequence to step (a), selecting treatment for the individual, wherein the selection of treatment is based on the FGF19 and FGFR4 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 and FGF19 expression are detected and treatment with an anti-FGF19 antibody is selected. In some embodiments, expression of FGFR4 is detected in a first biological sample, and expression of FGF19 is detected in a second biological sample. In some embodiments, the individual has a tumor, cancer, and/or a cell proliferative disorder, such as colorectal cancer, lung cancer, hepatocellular carcinoma, breast cancer and/or pancreatic cancer.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, further wherein FGF19 expression and/or FGFR4 expression is detected in the individual's biological sample before, during or after administration of an anti-FGF19 antibody. In some embodiments, the biological sample is of the cancer, tumor and/or cell proliferative disorder. In some embodiments, the biological sample is serum. In some embodiments, FGF19 over-expression is detected before, during and/or after administration of an anti-FGF19 antibody. In some embodiments, FGFR4 expression is detected before, during and/or after administration of an anti-FGF19 antibody. Expression may be detected before; during; after; before and during; before and after; during and after; or before, during and after administration of an anti-FGF19 antibody.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, wherein a biological sample of the cancer, tumor and/or cell disorder or liver disorder expresses FGF19 and/or FGFR4.

In embodiments involving detection, expression of FGFR4 downstream molecular signaling may be detected in addition to or as an alternative to detection of FGFR4 expression. In some embodiments, detection of FGFR4 downstream molecular signaling comprises one or more of detection of phosphorylation of MAPK, FRS2 or ERK2.

In some embodiments involving detection, expression of FGFR4 comprises detection of FGFR4 gene deletion, gene amplification and/or gene mutation. In some embodiments involving detection, expression of FGF19 comprises detection of FGF19 gene deletion, gene amplification and/or gene mutation.

Some embodiments involving detection further comprise detection of Wnt pathway activation. In some embodiments, detection of Wnt pathway activation comprises one or more of tyrosine phosphorylation of β-catenin, expression of Wnt target genes, β-catenin mutation, and E-cadherin binding to β-catenin. Detection of Wnt pathway activation is known in the art, and some examples are described and exemplified herein.

In some embodiments, the treatment is for a cancer selected from the group consisting of colorectal cancer, lung cancer, ovarian cancer, pituitary cancer, pancreatic cancer, mammary fibroadenoma, prostate cancer, head and neck squamous cell carcinoma, soft tissue sarcoma, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

Biological samples are described herein, e.g., in the definition of Biological Sample. In some embodiment, the biological sample is serum or of a tumor.

In embodiments involving detection of FGF19 and/or FGFR4 expression, FGF19 and/or FGFR4 polynucleotide expression and/or FGF19 and/or FGFR4 polypeptide expression may be detected. In some embodiments involving detection of FGF19 and/or FGFR4 expression, FGF19 and/or FGFR4 mRNA expression is detected. In other embodiments, FGF19 and/or FGFR4 polypeptide expression is detected using an anti-FGF19 agent and/or an anti-FGFR4 agent. In some embodiments, FGF19 and/or FGFR4 polypeptide expression is detected using an antibody. Any suitable antibody may be used for detection and/or diagnosis, including monoclonal and/or polyclonal antibodies, a human antibody, a chimeric antibody, an affinity-matured antibody, a humanized antibody, and/or an antibody fragment. In some embodiments, an anti-FGF19 antibody described herein is used for detection. In some embodiments, FGF19 and/or FGFR4 polypeptide expression is detected using immunohistochemistry (IHC). In some embodiments, FGF19 expression is scored at 2 or higher using an IHC.

In some embodiments involving detection of FGF19 and/or FGFR4 expression, presence and/or absence and/or level of FGF19 and/or FGFR4 expression may be detected. FGF19 and/or FGFR4 expression may be increased. It is understood that absence of FGF19 and/or FGFR4 expression includes insignificant, or de minimus levels. In some embodiments, FGF19 expression in the test biological sample is higher than that observed for a control biological sample (or control or reference level of expression). In some embodiments, FGF19 expression is at least about 2-fold, 5-fold, 10-fold, 20-fold, 30-fold, 40-fold, 50-fold, 75-fold, 100-fold, 150-fold higher, or higher, in the test biological sample than in the control biological sample. In some embodiments, FGF19 polypeptide expression is determined in an immunohistochemistry ("IHC") assay to score at least 2 or higher for staining intensity. In some embodiments, FGF19 polypeptide expression is determined in an IHC assay to score at least 1 or higher, or at least 3 or higher for staining intensity. In some embodiments, FGF19 expression in the test biological sample is lower than that observed for a control biological sample (or control expression level).

In one aspect, the invention provides an isolated polynucleotide comprising, consisting of, or consisting essentially of one or more of the following polynucleotide sequences:

```
                                           (SEQ ID NO: 41)
GAT CCC CCC TCG TGA GTC TAG ATC TAT TCA AGA GAT
AGA TCT AGA CTC ACG AGG TTT TTT GGA AA;

(SEQ ID NO: 42)
AGC TTT TCC AAA AAA CCT CGT GAG TCT AGA TCT ATC
TCT TGA ATA GAT CTA GAC TCA CGA GGG GG;

(SEQ ID NO: 43)
GAT CCC CGA ACC GCA TTG GAG GCA TTA TCA AGA GAA
ATG CCT CCA ATG CGG TTC TTT TTT GGA AA;
or (SEQ ID NO: 44)
AGC TTT TCC AAA AAA GAA CCG CAT TGG AGG CAT TTC
TCT TGA TAA TGC CTC CAA TGC GGT TCG GG.
```

DETAILED DESCRIPTION OF THE INVENTION

Figure 1A:
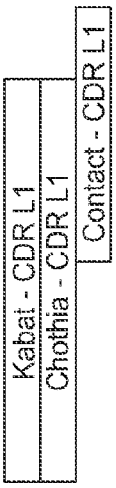
FIGS. 1A and B: depicts the amino acid sequences of mouse anti-human FGF19 monoclonal antibody 1A6 variable regions. (A) light chain variable region (SEQ ID NO:4). (B) heavy chain variable region (SEQ ID NO:8) Amino acids are numbered according to Kabat. The positions of the HVRs are depicted in the Figures.
Figure 1A:
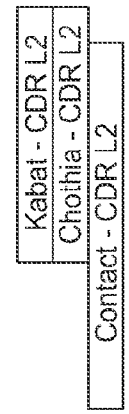
Figure 1A:
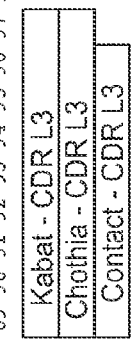

The invention herein provides anti-FGF19 antibodies, which are useful for, e.g., treatment or prevention of disease states associated with expression and/or activity of FGF19, such as increased expression and/or activity or undesired expression and/or activity. In some embodiments, the antibodies of the invention are used to treat a tumor, a cancer, and/or a cell proliferative disorder.

In another aspect, the anti-FGF19 antibodies of the invention find utility as reagents for detection and/or isolation of FGF19, such as detention of FGF19 in various tissues and cell type.

The invention further provides methods of making anti-FGF19 antibodies, polynucleotides encoding anti-FGF19 antibodies, and cells comprising polynucleotides encoding anti-FGF19 antibodies.

In another aspect, the invention provides methods comprising detection of FGF19 and/or FGFR4

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS 1N MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol 293: 865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment the Kd or Kd value is measured by using surface plasmon resonance assays using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol 293:865-881. If the on-rate exceeds $10^6 M^{-1}S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25 C with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 ug/ml (~0.2 uM) before injection at a flow rate of 5 ul/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 ul/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol 293:865-881. However, if the on-rate exceeds $10^6 M^{-1}S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The term "FGF19" (interchangeably termed "Fibroblast growth factor 19"), as used herein, refers, unless specifically or contextually indicated otherwise, to any native or variant (whether native or synthetic) FGF19 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type FGF19" generally refers to a polypeptide comprising the amino acid sequence of a naturally occurring FGF19 protein. The term "wild type FGF19 sequence" generally refers to an amino acid sequence found in a naturally occurring FGF19.

The term "FGFR4" (interchangeably termed "Fibroblast growth factor receptor 4"), as used herein, refers, unless specifically or contextually indicated otherwise, to any native or variant (whether native or synthetic) FGFR4 polypeptide. The term "native sequence" specifically encompasses naturally occurring truncated or secreted forms (e.g., an extracellular domain sequence), naturally occurring variant forms (e.g., alternatively spliced forms) and naturally-occurring allelic variants. The term "wild type FGFR4" generally refers to a polypeptide comprising the amino acid sequence of a naturally occurring FGFR4 protein. The term "wild type FGFR4 sequence" generally refers to an amino acid sequence found in a naturally occurring FGFR4.

The terms "antibody" and "immunoglobulin" are used interchangeably in the broadest sense and include monoclonal antibodies (for e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CHI) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures.

Hypervariable regions may comprise "extended hypervariable regions" as follows: 24-36 (L1), 46-56 (L2) and 89-97 (L3) in the VL and 26-35 (H1), 49-65 or 50 to 65 (H2) and 93-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g. from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins.

WO00/42072 (Presta) describes antibody variants with improved or diminished binding to FcRs. The content of that patent publication is specifically incorporated herein by reference. See, also, Shields et al. *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen: To assess complement activation, a CDC assay, e.g. as described in Gazzano-Santoro et al., *J. Immunol. Methods* 202:163 (1996), may be performed.

Polypeptide variants with altered Fc region amino acid sequences and increased or decreased Clq binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

A "blocking" antibody or an "antagonist" antibody is one which inhibits or reduces biological activity of the antigen it binds. Preferred blocking antibodies or antagonist antibodies substantially or completely inhibit the biological activity of the antigen.

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

A "medicament" is an active drug to treat the disorder in question or its symptoms, or side effects.

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, pituitary cancer, esophageal cancer, astrocytoma, soft tissue sarcoma, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The term "wasting" disorders (e.g., wasting syndrome, cachexia, sarcopenia) refers to a disorder caused by undesirable and/or unhealthy loss of weight or loss of body cell mass. In the elderly as well as in AIDS and cancer patients, wasting disease can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease which is sometimes also referred to as cachexia, a metabolic and, sometimes, an eating disorder. Cachexia is additionally characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Mayer, 1999, J. Nutr. 129 (IS Suppl.):256S-259S). Sarcopenia, yet another such disorder which can affect the aging individual, is typically characterized by loss of muscle mass. End stage wasting disease as described above can develop in individuals suffering from either cachexia or sarcopenia.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or disorder.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT/SU11248 (sunitinib malate), AMG706). Anti-angiogenesis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12):1359-1364 (1999); Tonini et al., Oncogene, 22:6549-6556 (2003) (e.g., Table 2 listing antiangiogenic factors); and, Sato Int. J. Clin. Oncol., 8:200-206 (2003) (e.g., Table 1 lists Anti-angiogenic agents used in clinical trials).

An "individual" is a vertebrate, preferably a mammal, more preferably a human. Mammals include, but are not limited to, farm animals (such as cows), sport animals, pets (such as cats, dogs and horses), primates, mice and rats.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin; azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Rat H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing FGF19) either in vitro or in vivo. Thus, the growth inhibitory agent may be one which significantly reduces the percentage of cells (such as a cell expressing FGF19) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-Iyxo-hexapyranosyl)oxy]-7,8,9,10-tetrahydro-6,8,11-trihydroxy-8-(hydroxyacetyl)-1-methoxy-5,12-naphthacenedione.

The term "Fc region-comprising polypeptide" refers to a polypeptide, such as an antibody or immunoadhesin (see definitions below), which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

Compositions of the Invention and Methods of Making Same

This invention encompasses compositions, including pharmaceutical compositions, comprising an anti-FGF19 antibody; and polynucleotides comprising sequences encoding an anti-FGF19 antibody. As used herein, compositions comprise one or more antibodies that bind to FGF19, and/or one or more polynucleotides comprising sequences encoding one or more antibodies that bind to FGF19. These compositions may further comprise suitable carriers, such as pharmaceutically acceptable excipients including buffers, which are well known in the art.

The invention also encompasses isolated antibody and polynucleotide embodiments. The invention also encompasses substantially pure antibody and polynucleotide embodiments.

The anti-FGF19 antibodies of the invention are preferably monoclonal. Also encompassed within the scope of the invention are Fab, Fab', Fab'-SH and F(ab')$_2$ fragments of the anti-FGF19 antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-FGF19 monoclonal antibodies of the invention can be made using the hybridoma method first described by Kohler et al, *Nature*, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to FGF19 generally are raised in animals by multiple subcutaneous (sc) or intraperitoneal (ip) injections of FGF19 and an adjuvant. FGF19 may be prepared using methods well-known in the art, some of which are further described herein. For example, recombinant production of FGF19 is described below. In one embodiment, animals are immunized with a derivative of FGF19 that contains the extracellular domain (ECD) of FGF19 fused to the Fc portion of an immunoglobulin heavy chain. In one embodiment, animals are immunized with an FGF19-IgG1 fusion protein. Animals ordinarily are immunized against immunogenic conjugates or derivatives of FGF19 with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-FGF19 titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against FGF19. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-FGF19 antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-FGF19 antibodies of the invention can be obtained by designing a suitable antigen screening procedure to select for the phage clone of interest followed by construction of a full length anti-FGF19 antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., J. Mol. Biol., 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-FGF19 clones is desired, the subject is immunized with FGF19 to generate an antibody response, and spleen cells and/or circulating B cells other peripheral blood lymphocytes (PBLs) are recovered for library construction. In a preferred embodiment, a human antibody gene fragment library biased in favor of anti-human FGF19 clones is obtained by generating an anti-human FGF19 antibody response in transgenic mice carrying a functional human immunoglobulin gene array (and lacking a functional endogenous antibody production system) such that FGF19 immunization gives rise to B cells producing human antibodies against FGF19. The generation of human antibody-producing transgenic mice is described below.

Additional enrichment for anti-FGF19 reactive cell populations can be obtained by using a suitable screening procedure to isolate B cells expressing FGF19-specific membrane bound antibody, e.g., by cell separation with FGF19 affinity chromatography or adsorption of cells to fluorochrome-labeled FGF19 followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which FGF19 is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (*USA*), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al, *Proc. Natl. Acad. Sci.* (*USA*), 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991). Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol.* 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al, *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ $M^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$M range.

Nucleic acid sequence encoding an FGF19 can be designed using the amino acid sequence of the desired region of FGF19. Alternatively, the cDNA sequence (or fragments thereof) may be used. Additional FGF19 sequences are further disclosed in, e.g., NM_022963, and Xie et al. (1999) *Cytokine* 11:729-735. DNAs encoding FGF19 can be prepared by a variety of methods known in the art. These methods include, but are not limited to, chemical synthesis by any of the methods described in Engels et al., *Agnew. Chem. Int.*

*Ed. Engl.,* 28: 716-734 (1989), such as the triester, phosphite, phosphoramidite and H-phosphonate methods. In one embodiment, codons preferred by the expression host cell are used in the design of the FGF19-encoding DNA. Alternatively, DNA encoding FGF19 can be isolated from a genomic or cDNA library.

Following construction of the DNA molecule encoding FGF19, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding FGF19 is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.,* 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce FGF19 can be cultured as described generally in Sambrook et al., supra.

The mammalian host cells used to produce FGF19 can be cultured in a variety of media, which is well known in the art and some of which is described herein.

The host cells referred to in this disclosure encompass cells in in vitro culture as well as cells that are within a host animal.

Purification of FGF19 may be accomplished using art-recognized methods.

The purified FGF19 can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the FGF19 protein to the matrix can be accomplished by the methods described in *Methods in Enzymology,* vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, FGF19 can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized FGF19 under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA,* 88: 7978-7982 (1991), or by alkali, e.g. as described in Marks et al., *J. Mol. Biol.,* 222: 581-597 (1991), or by FGF19 antigen competition, e.g. in a procedure similar to the antigen competition method of Clackson et al., *Nature,* 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

It is possible to select between phage antibodies of different affinities, even with affinities that differ slightly, for FGF19. However, random mutation of a selected antibody (e.g. as performed in some of the affinity maturation techniques described above) is likely to give rise to many mutants, most binding to antigen, and a few with higher affinity. With limiting FGF19, rare high affinity phage could be competed out. To retain all the higher affinity mutants, phages can be incubated with excess biotinylated FGF19, but with the biotinylated FGF19 at a concentration of lower molarity than the target molar affinity constant for FGF19. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics. Anti-FGF19 clones may also be activity selected.

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs,* 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-FGF19 antibody derived from a hybridoma of the invention can also be modified, for example, by substituting the coding sequence for human heavy- and light-chain constant domains in place of homologous murine sequences derived from the hybridoma clone (e.g. as in the method of Morrison et al, *Proc. Natl. Acad. Sci. USA,* 81: 6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869, 046. Other techniques for the production of antibody fragments will be apparent to the skilled practitioner. In other embodiments, the antibody of choice is a single chain Fv fragment (scFv). See WO 93/16185; U.S. Pat. Nos. 5,571, 894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816, 567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-FGF19 antibodies of the invention can be constructed by combining Fv clone variable domain sequence(s) selected from human-derived phage display libraries with known human constant domain sequences(s) as described above. Alternatively, human monoclonal anti-FGF19 antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for FGF19 and the other is for any other antigen. Exemplary bispecific antibodies may bind to two different epitopes of the FGF19 protein. Bispecific antibodies may also be used to localize cytotoxic agents to cells which express FGF19. These antibodies possess an FGF19-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $CH_2$, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human. T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et at, Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al. J. Immunol. 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336: 1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) hydrophobic: norleucine, met, ala, val, leu, ile;
  (2) neutral hydrophilic: Cys, Ser, Thr, Asn, Gln;
  (3) acidic: asp, glu;
  (4) basic: his, lys, arg;
  (5) residues that influence chain orientation: gly, pro; and
  (6) aromatic: trp, tyr, phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine. In accordance with this description and the teachings of the art, it is contemplated that in some embodiments, an antibody used in methods of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the invention bind FGF19, and in some embodiments, may modulate one or more aspects of FGF19-associated effects, including but not limited to FGFR4 activation, FGFR4 downstream molecular signaling, disruption of FGFR4 binding to FGF19, FGFR4 multimerization, expression of a CYP7α1 gene, phosphorylation of FGFR4, MAPK, FRS2 and/or ERK2, activation of β-catenin, FGF19-promoted cell migration, and/or disruption of any biologically relevant FGF19 and/or FGFR4 biological pathway, and/or treatment and/or prevention of a tumor, cell proliferative disorder or a cancer; and/or treatment or prevention of a disorder associated with FGF19 expression and/or activity (such as increased FGF19 expression and/or activity).

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding assay are provided below in the Examples section.

In some embodiments, the invention provides anti-FGF19 monoclonal antibodies that compete with an antibody comprising a light chain variable domain having the sequence: DIKMTQSPSSMYASLGERVTIPCKASQ-DINSFLSWFQQKPGKSPKTLIYRANR-LVDGVPSRFSGSGSGQDYSL TISSLEYEDMGIYY-CLQYDEFPLTFGAGTKVEIKR (SEQ ID NO:4) and a heavy chain variable domain having the sequence: QVQLKQSGPGLVQPSQSLSITCTVSGFS-LITYGVHWVRQSPGKGLEWLGVIW-PGGGTDYNAAFISRLSITKD NSKSQVFFK-MNSLLANDTAIYFCVRKEYANLYAMDYWGQGTLLT VSA (SEQ ID NO:8) for binding to FGF19. Such competitor antibodies include antibodies that recognize an FGF19 epitope that is the same as or overlaps with the FGF19 epitope recognized by the antibody. Such competitor antibodies can be obtained by screening anti-FGF19 hybridoma supernatants for binding to immobilized FGF19 in competition with labeled antibody comprising a light chain variable domain having the sequence: DIKMTQSPSSMYASLGERVTIPCKASQ-DINSFLSWFQQKPGKSPKTLIYRANR-LVDGVPSRFSGSGSGQDYSL TISSLEYEDMGIYY-CLQYDEFPLTFGAGTKVEIKR (SEQ ID NO:4) and a heavy chain variable domain having the sequence: QVQLKQSGPGLVQPSQSLSITCTVSGFS-LTTYGVHWVRQSPGKGLEWLGVIW-PGGGTDYNAAFISRLSITKD NSKSQVFFK-MNSLLANDTAIYFCVRKEYANLYAMDYWGQGTLLT VSA (SEQ ID NO:8). A hybridoma supernatant containing competitor antibody will reduce the amount of bound, labeled antibody detected in the subject competition binding mixture as compared to the amount of bound, labeled antibody detected in a control binding mixture containing irrelevant (or no) antibody. Any of the competition binding assays described herein are suitable for use in the foregoing procedure.

Anti-FGF19 antibodies of the invention possessing the properties described herein can be obtained by screening anti-FGF19 hybridoma clones for the desired properties by any convenient method. For example, if an anti-FGF19 monoclonal antibody that blocks or does not block the binding of FGFR4 to FGF19 is desired, the candidate antibody can be tested in a binding competition assay. Competition assays are well known in the art, and one such assay is described in the Examples.

Other functional assays to determine the inhibitory capacity of anti-FGF19 antibodies are known in the art, some of which are exemplified herein.

In some embodiments, the present invention contemplates altered antibodies that possess some but not all effector functions, which make it a desired candidate for many applications in which the half life of the antibody in vivo is important yet certain effector functions (such as complement and ADCC) are unnecessary or deleterious. In certain embodiments, the Fe activities of the produced immunoglobulin are measured to ensure that only the desired properties are maintained. In vitro and/or in vivo cytotoxicity assays can be conducted to confirm the reduction/depletion of CDC and/or ADCC activities. For example, Fe receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

In some embodiments, the invention provides altered antibodies that possess increased effector functions and/or increased half-life.

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 karat (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J Bio Chem 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from Staphylococcus aureas which binds with a high affinity to the Fc region of antibodies. Lindmark et al (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively; host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-FGF19 antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (eg., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolastatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7):778-784; "Monomethylvaline Compounds Capable of Conjugation to Ligands", U.S. Ser. No. 10/983, 340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712, 374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAN, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \quad\quad\quad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

The invention provides methods and compositions useful for modulating disease states associated with expression and/or activity of FGF19 and/or FGFR4, such as increased expression and/or activity or undesired expression and/or activity, said methods comprising administration of an effective dose of an anti-FGF19 antibody to an individual in need of such treatment. In some embodiments, the disease state is associated with increased expression of FGF19, and the disease state comprises cholestasis or dysregulation of bile acid metabolism.

In one aspect, the invention provides methods for treating or preventing a tumor, a cancer, and/or a cell proliferative disorder, the methods comprising administering an effective amount of an anti-FGF19 antibody to an individual in need of such treatment.

In one aspect, the invention provides methods for treating or preventing a tumor, a cancer, and/or a cell proliferative disorder associated with increased expression and/or activity of FGF19, the methods comprising administering an effective amount of an anti-FGF19 antibody to an individual in need of such treatment.

In one aspect, the invention provides methods for treating or preventing a tumor, a cancer, and/or a cell proliferative disorder associated with increased expression and/or activity of FGFR4, the methods comprising administering an effective amount of an anti-FGF19 antibody to an individual in need of such treatment.

In one aspect, the invention provides methods for treating and/or preventing a liver disorder, the methods comprising administering an effective amount of an anti-FGF19 antibody to an individual in need of such treatment In some embodiments, the liver disorder is cirrhosis.

In one aspect, the invention provides methods for treating and/or preventing a wasting disorder, the methods comprising administering an effective amount of an anti-FGF19 antibody to an individual in need of such treatment. In some embodiments, the individual has a tumor, a cancer, and/or a cell proliferative disorder.

It is understood that any suitable anti-FGF19 antibody may be used in methods of treatment, including monoclonal and/or polyclonal antibodies, a human antibody, a chimeric antibody, an affinity-matured antibody, a humanized antibody, and/or an antibody fragment. In some embodiments, any anti-FGF19 antibody described herein is used for treatment.

Moreover, at least some of the antibodies of the invention can bind antigen from other species. Accordingly, the antibodies of the invention can be used to bind specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for binding an antigen in an individual suffering from a disorder associated with increased antigen expression and/or activity, comprising administering to the subject an antibody of the invention such that the antigen in the subject is bound. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of one or more antigen molecules.

In certain embodiments, an immunoconjugate comprising an antibody conjugated with one or more cytotoxic agent(s) is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

In any of the methods herein, one may administer to the subject or patient along with the antibody herein an effective amount of a second medicament (where the antibody herein is a first medicament), which is another active agent that can treat the condition in the subject that requires treatment. For instance, an antibody of the invention may be co-administered with another antibody, chemotherapeutic agent(s) (including cocktails of chemotherapeutic agents), anti-angiogenic agent(s), immunosuppressive agents(s), cytokine(s), cytokine antagonist(s), and/or growth-inhibitory agent(s). The type of such second medicament depends on various factors, including the type of disorder, such as cancer or an autoimmune disorder, the severity of the disease, the condition and age of the patient, the type and dose of first medicament employed, etc.

Where an antibody of the invention inhibits tumor growth, for example, it may be particularly desirable to combine it with one or more other therapeutic agents that also inhibit tumor growth. For instance, an antibody of the invention may be combined with an anti-angiogenic agent, such as an anti-VEGF antibody (e.g., AVASTIN®) and/or anti-ErbB antibodies (e.g. HERCEPTIN® trastuzumab anti-HER2 antibody or an anti-HER2 antibody that binds to Domain II of HER2, such as OMNITARG™ pertuzumab anti-HER2 antibody) in a treatment scheme, e.g. in treating any of the disease described herein, including colorectal cancer, lung cancer, hepatocellular carcinoma, breast cancer and/or pancreatic cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies. In addition, combining an antibody of this invention with a relatively non-cytotoxic agent such as another biologic molecule, e.g., another antibody is expected to reduce cytotoxicity versus combining the antibody with a chemotherapeutic agent of other agent that is highly toxic to cells.

Treatment with a combination of the antibody herein with one or more second medicaments preferably results in an improvement in the signs or symptoms of cancer. For instance, such therapy may result in an improvement in survival (overall survival and/or progression-free survival) relative to a patient treated with the second medicament only (e.g., a chemotherapeutic agent only), and/or may result in an objective response *(partial or complete, preferably complete). Moreover, treatment with the combination of an antibody herein and one or more second medicament(s) preferably results in an additive, and more preferably synergistic (or greater than additive), therapeutic benefit to the patient. Preferably, in this combination method the timing between at least one administration of the second medicament and at least one administration of the antibody herein is about one month or less, more preferably, about two weeks or less.

For treatment of cancers, the second medicament is preferably another antibody, chemotherapeutic agent (including cocktails of chemotherapeutic agents), anti-angiogenic agent, immunosuppressive agent, prodrug, cytokine, cytokine antagonist, cytotoxic radiotherapy, corticosteroid, anti-emetic, cancer vaccine, analgesic, anti-vascular agent, and/or growth-inhibitory agent. The cytotoxic agent includes an agent interacting with DNA, the antimetabolites, the topoisomerase I or II inhibitors, or the spindle inhibitor or stabilizer agents (e.g., preferably vinca alkaloid, more preferably selected from vinblastine, deoxyvinblastine, vincristine, vindesine, vinorelbine, vinepidine, vinfosiltine, vinzolidine and vinfunine), or any agent used in chemotherapy such as 5-FU, a taxane, doxorubicin, or dexamethasone.

In another embodiment, the second medicament is another antibody used to treat cancers such as those directed against the extracellular domain of the HER2/neu receptor, e.g., trastuzumab, or one of its functional fragments, pan-HER inhibitor, a Src inhibitor, a MEK inhibitor, or an EGFR inhibitor (e.g., an anti-EGFR antibody (such as one inhibiting the tyrosine kinase activity of the EGFR), which is preferably the mouse monoclonal antibody 225, its mouse-man chimeric derivative C225, or a humanized antibody derived from this antibody 225 or derived natural agents, dianilinophthalimides, pyrazolo- or pyrrolopyridopyrimidines, quinazilines, gefitinib, erlotinib, cetuximab, ABX-EFG, canertinib, EKB-569 and PKI-166), or dual-EGFR/HER-2 inhibitor such as lapatanib. Additional second medicaments include alemtuzumab (CAMPATH™), FavID (IDKLH), CD20 antibodies with altered glycosylation, such as GA-101/GLYCART™, oblimersen (GENASENSE™), thalidomide and analogs thereof, such as lenalidomide (REVLIMID™), imatinib, sorafenib, ofatumumab (HUMAX-CD20™), anti-CD40 antibody, e.g. SGN-40, and anti-CD-80 antibody, e.g. galiximab:

The anti-emetic agent is preferably ondansetron hydrochloride, granisetron hydrochloride, metroclopramide, domperidone, haloperidol, cyclizine, lorazepam, prochlorperazine, dexamethasone, levomepromazine, or tropisetron. The vaccine is preferably GM-CSF DNA and cell-based vaccines, dendritic cell vaccine, recombinant viral vaccines, heat shock protein (HSP) vaccines, allogeneic or autologous tumor vaccines. The analgesic agent preferably is ibuprofen, naproxen, choline magnesium trisalicylate, or oxycodone hydrochloride. The anti-vascular agent preferably is bevacizumab, or rhuMAb-VEGF. Further second medicaments include anti-proliferative agents such a farnesyl protein transferase inhibitors, anti-VEGF inhibitors, p53 inhibitors, or PDGFR inhibitors. The second medicament herein includes also biologic-targeted therapy such as treatment with antibodies as well as small-molecule-targeted therapy, for example, against certain receptors.

Many anti-angiogenic agents have been identified and are known in the art, including those listed herein, e.g., listed under Definitions, and by, e.g., Carmeliet and Jain, Nature 407:249-257 (2000); Ferrara et al., Nature Reviews: Drug Discovery, 3:391-400 (2004); and Sato Int. J. Clin. Oncol., 8:200-206 (2003). See also, US Patent Application US20030055006. In one embodiment, an anti-FGF19 antibody is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the patient in addition to VEGF antagonist and other agent. In certain embodiment, one or more additional therapeutic agents, e.g., anti-cancer agents, can be administered in combination with anti-FGF19 antibody, the VEGF antagonist, and an anti-angiogenesis agent.

Chemotherapeutic agents useful herein are described supra, e.g., in the definition of "chemotherapeutic agent".

Exemplary second medicaments include an alkylating agent, a folate antagonist, a pyrimidine antagonist, a cytotoxic antibiotic, a platinum compound or platinum-based compound, a taxane, a vinca alkaloid, a c-Kit inhibitor, a topoisomerase inhibitor, an anti-angiogenesis inhibitor such as an anti-VEGF inhibitor, a HER-2 inhibitor, an EGFR inhibitor or dual EGFR/HER-2 kinase inhibitor, an anti-estrogen such as fulvestrant, and a hormonal therapy agent, such as carboplatin, cisplatin, gemcitabine, capecitabine, epirubicin, tamoxifen, an aromatase inhibitor, and prednisone. Most preferably, the cancer is colorectal cancer and the second medicament is an EGFR inhibitor such as erlotinib, an anti-VEGF inhibitor such as bevacizumab, or is cetuximab, arinotecan, irinotecan, or FOLFOX, or the cancer is breast cancer an the second medicament is an anti-estrogen modulator such as fulvestrant, tamoxifen or an aromatase inhibitor such as letrozole, exemestane, or anastrozole, or is a VEGF inhibitor such as bevacizumab, or is a chemotherapeutic agent such as doxorubicin, and/or a taxane such as paclitaxel, or is an anti-HER-2 inhibitor such as trastuzumab, or a dual EGFR/HER-2 kinase inhibitor such as lapatinib or a HER-2 downregulator such as 17AAG (geldanamycin derivative that is a heat shock protein [Hsp] 90 poison) (for example, for breast cancers that have progressed on trastuzumab). In other embodiments, the cancer is lung cancer, such as small-cell lung cancer, and the second medicament is a VEGF inhibitor such as bevacizumab, or an EGFR inhibitor such as, e.g., erlotinib or a c-Kit inhibitor such as e.g., imatinib. In other embodiments, the cancer is liver cancer, such as hepatocellular carcinoma, and the second medicament is an EGFR inhibitor such as erlotinib, a chemotherapeutic agent such as doxorubicin or irinotecan, a taxane such as paclitaxel, thalidomide and/or interferon. Further, a preferred chemotherapeutic agent for front-line therapy of cancer is taxotere, alone or in combination with other second medicaments. Most preferably, if chemotherapy is administered, it is given first, followed by the antibodies herein.

Such second medicaments may be administered within 48 hours after the antibodies herein are administered, or within 24 hours, or within 12 hours, or within 3-12 hours after said agent, or may be administered over a pre-selected period of time, which is preferably about 1 to 2 days. Further, the dose of such agent may be sub-therapeutic.

The antibodies herein can be administered concurrently, sequentially, or alternating with the second medicament or upon non-responsiveness with other therapy. Thus, the combined administration of a second medicament includes co-administration (concurrent administration), using separate formulations or a single pharmaceutical formulation, and consecutive administration in either order, wherein preferably there is a time period while both (or all) medicaments simultaneously exert their biological activities. All these second medicaments may be used in combination with each other or by themselves with the first medicament, so that the express "second medicament" as used herein does not mean it is the only medicament besides the first medicament, respectively. Thus, the second medicament need not be one medicament, but may constitute or comprise more than one such drug.

These second medicaments as set forth herein are generally used in the same dosages and with administration routes as the first medicaments, or about from 1 to 99% of the dosages of the first medicaments. If such second medicaments are used at all, preferably, they are used in lower amounts than if the first medicament were not present, especially in subsequent dosings beyond the initial dosing with the first medicament, so as to eliminate or reduce side effects caused thereby.

The invention also provides methods and compositions for inhibiting or preventing relapse tumor growth or relapse cancer cell growth. Relapse tumor growth or relapse cancer cell growth is used to describe a condition in which patients undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the patients or the patients are no longer receiving any beneficial effect from the therapy such that these patients need additional effective therapy. As used herein, the phrase can also refer to a condition of the "non-responsive/refractory" patient, e.g., which describe patients who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in a subject by administering one or more anti-FGF19 antibody to block or reduce the relapse tumor growth or relapse cancer cell growth in subject. In certain embodiments, the antagonist can be administered subsequent to the cancer therapeutic. In certain embodiments, the anti-FGF19 antibody is administered simultaneously with cancer therapy. Alternatively, or additionally, the anti-FGF19 antibody therapy alternates with another cancer therapy, which can be performed in any order. The invention also encompasses methods for administering one or more inhibitory antibodies to prevent the onset or recurrence of cancer in patients predisposed to having cancer. Generally, the subject was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and an anti-FGF19 antibody for blocking or reducing relapse tumor growth or relapse cancer cell growth.

The antibodies of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibodies are suitably administered by pulse infusion, particularly with declining doses of the antibody. Dosing can be by any suitable route, e.g. by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

The anti-FGF19 antibodies of the invention are useful in assays detecting FGF19 expression (such as diagnostic or prognostic assays) in specific cells or tissues wherein the antibodies are labeled as described below and/or are immobilized on an insoluble matrix. However, it is understood that any suitable anti-FGF19 antibody may be used in embodiments involving detection and diagnosis. Some methods for making anti-FGF19 antibodies are described herein and methods for making anti-FGF19 antibodies are well known in the art.

In another aspect, the invention provides methods for detection of FGF19, the methods comprising detecting FGF19-anti-FGF19 antibody complex in the sample. The term "detection" as used herein includes qualitative and/or quantitative detection (measuring levels) with or without reference to a control.

In another aspect, the invention provides methods for diagnosing a disorder associated with FGF19 expression and/or activity, the methods comprising detecting FGF19-anti-FGF19 antibody complex in a biological sample from an individual having or suspected of having the disorder. In some embodiments, the FGF19 expression is increased expression or abnormal (undesired) expression.

In another aspect, the invention provides any of the anti-FGF19 antibodies described herein, wherein the anti-FGF19 antibody comprises a detectable label.

In another aspect, the invention provides a complex of any of the anti-FGF19 antibodies described herein and FGF19. In some embodiments, the complex is in vivo or in vitro. In some embodiments, the complex comprises a cancer cell. In some embodiments, the anti-FGF19 antibody is detectably labeled.

Anti-FGF19 antibodies (e.g., any of the FGF19 antibodies described herein) can be used for the detection of FGF19 in any one of a number of well known detection assay methods.

In one aspect, the invention provides methods for detecting a disorder associated with FGF19 expression and/or activity, the methods comprising detecting FGF19 in a biological sample from an individual. In some embodiments, the FGF19 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for selecting treatment for an individual, the methods comprising: (a) detecting FGF19 expression in an individual's biological sample, if any; and (b) subsequence to step (a), selecting treatment for the individual, wherein the selection of treatment is based on the FGF19 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, FGF19 expression is detected and treatment with an anti-FGF19 antibody is selected. Methods of treating a disorder with an anti-FGF19 antibody are described herein and some methods are exemplified herein.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, further wherein FGF19 expression and/or FGFR4 is detected in cells and/or tissue from the human patient before, during or after administration of an anti-FGF19 antibody. In some embodiments, FGF19 overexpression is detected before, during and/or after administration of an anti-FGF19 antibody. In some embodiments, FGFR4 expression is detected before, during and/or after administration of an anti-FGF19 antibody. Expression may be detected before; during; after; before and during; before and after, during and after; or before, during and after administration of an anti-FGF19 antibody. Methods of treating a disorder with an anti-FGF19 antibody are described herein and some methods are exemplified herein.

For example, a biological sample may be assayed for FGF19 by obtaining the sample from a desired source, admixing the sample with anti-FGF19 antibody to allow the antibody to form antibody/FGF19 complex with any FGF19 present in the mixture, and detecting any antibody/FGF19 complex present in the mixture. The biological sample may be prepared for assay by methods known in the art which are suitable for the particular sample. The methods of admixing the sample with antibodies and the methods of detecting antibody/FGF19 complex are chosen according to the type of assay used. Such assays include immunohistochemistry, competitive and sandwich assays, and steric inhibition assays. For sample preparation, a tissue or cell sample from a mammal (typically a human patient) may be used. Examples of samples include, but are not limited to, cancer cells such as colon, breast, prostate, ovary, lung, stomach, pancreas, lymphoma, and leukemia cancer cells. FGF19 may also be measured in serum. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology (See e.g., "Manual of Histological Staining Method of the Armed Forces Institute of Pathology," 3$^{rd}$ edition (1960) Lee G. Luna, H T (ASCP) Editor, The Blakston Division McGraw-Hill Book Company, New York; *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used. By way of example, neutral buffered formalin, Bouin's or paraformaldehyde, may be used to fix a sample. Generally, the sample is first fixed and is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissuemay. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine. If paraffin has been used as the embedding material, the tissue sections are generally deparaffinized and rehydrated to water. The tissue sections may be deparaffinized by several conventional standard methodologies. For example, xylenes and a gradually descending series of alcohols may be used (See e.g., "Manual of Histological Staining Method of the Armed Forces Institute of Pathology", supra). Alternatively, commercially available deparaffinizing non-organic agents such as Hemo-De7 (CMS, Houston, Tex.) may be used.

Analytical methods for FGF19 all use one or more of the following reagents: labeled FGF19 analogue, immobilized FGF19 analogue, labeled anti-FGF19 antibody, immobilized anti-FGF19 antibody and steric conjugates. The labeled reagents also are known as "tracers."

The label used is any detectable functionality that does not interfere with the binding of FGF19 and anti-FGF19 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected.

The label used is any detectable functionality that does not interfere with the binding of FGF19 and anti-FGF19 antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. Nos. 3,940,475 (fluorimetry) and 3,645,090 (enzymes); Hunter et al., *Nature,* 144: 945 (1962); David et al., *Biochemistry,* 13: 1014-1021 (1974); Pain et al., *J. Immunol. Methods,* 40: 219-230 (1981); and Nygren, *J. Histochem. and Cytochem.,* 30: 407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology,* ed. J. J. Langone and H. Van Vunakis, Vol. 73 (Academic Press, New York, N.Y., 1981), pp. 147-166.

Immobilization of reagents is required for certain assay methods. Immobilization entails separating the anti-FGF19 antibody from any FGF19 that remains free in solution. This conventionally is accomplished by either insolubilizing the anti-FGF19 antibody or FGF19 analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-FGF19 antibody or FGF19 analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human patient) may be used. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e. preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., FGF19) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g. HRPO) which catalyzes a chemical alteration of the chromogenic substrate such as 3,3'-diaminobenzidine chromogen. Preferably the enzymatic label is conjugated to antibody which binds specifically to the primary antibody (e.g. the primary antibody is rabbit polyclonal antibody and secondary antibody is goat anti-rabbit antibody).

Specimens thus prepared may be mounted and coverslipped. Slide evaluation is then determined, e.g. using a microscope, and staining intensity criteria, routinely used in the art, may be employed.

Other assay methods, known as competitive or sandwich assays, are well established and widely used in the commercial diagnostics industry.

Competitive assays rely on the ability of a tracer FGF19 analogue to compete with the test sample FGF19 for a limited number of anti-FGF19 antibody antigen-binding sites. The anti-FGF19 antibody generally is insolubilized before or after the competition and then the tracer and FGF19 bound to the anti-FGF19 antibody are separated from the unbound tracer and FGF19. This separation is accomplished by decanting (where the binding partner was preinsolubilized) or by centrifuging (where the binding partner was precipitated after the competitive reaction). The amount of test sample FGF19 is inversely proportional to the amount of bound tracer as measured by the amount of marker substance. Dose-response curves with known amounts of FGF19 are prepared and compared with the test results to quantitatively determine the amount of FGF19 present in the test sample. These assays are called ELISA systems when enzymes are used as the detectable markers.

Another species of competitive assay, called a "homogeneous" assay, does not require a phase separation. Here, a conjugate of an enzyme with the FGF19 is prepared and used such that when anti-FGF19 antibody binds to the FGF19 the presence of the anti-FGF19 antibody modifies the enzyme activity. In this case, the FGF19 or its immunologically active fragments are conjugated with a bifunctional organic bridge to an enzyme such as peroxidase. Conjugates are selected for use with anti-FGF19 antibody so that binding of the anti-FGF19 antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small FGF19 fragment so that antibody to hapten is substantially unable to bind the conjugate at the same time as anti-FGF19 antibody. Under this assay procedure the FGF19 present in the test sample will bind anti-FGF19 antibody, thereby allowing anti-hapten to bind the conjugate, resulting in a change in the character of the conjugate hapten, e.g., a change in fluorescence when the hapten is a fluorophore.

Sandwich assays particularly are useful for the determination of FGF19 or anti-FGF19 antibodies. In sequential sandwich assays an immobilized anti-FGF19 antibody is used to adsorb test sample FGF19, the test sample is removed as by washing, the bound FGF19 is used to adsorb a second, labeled anti-FGF19 antibody and bound material is then separated from residual tracer. The amount of bound tracer is directly proportional to test sample FGF19. In "simultaneous" sandwich assays the test sample is not separated before adding the labeled anti-FGF19. A sequential sandwich assay using an anti-FGF19 monoclonal antibody as one antibody and a polyclonal anti-FGF19 antibody as the other is useful in testing samples for FGF19.

The foregoing are merely exemplary detection assays for FGF19. Other methods now or hereafter developed that use anti-FGF19 antibody for the determination of FGF19 are included within the scope hereof, including the bioassays described herein.

In one aspect, the invention provides methods to detect (e.g., presence or absence of or amount) a polynucleotide(s) (e.g., FGF19 polynucleotides) in a biological sample from an individual, such as a human subject. A variety of methods for detecting polynucleotides can be employed and include, for example, RT-PCR, TaqMan, amplification methods, polynucleotide microarray, and the like.

Methods for the detection of polynucleotides (such as mRNA) are well known and include, for example, hybridization assays using complementary DNA probes (such as in situ hybridization using labeled FGF19 riboprobes), Northern blot and related techniques, and various nucleic acid amplification assays (such as RT-PCR using complementary primers specific for FGF19, and other amplification type detection methods, such as, for example, branched DNA, SPIA, Ribo-SPIA, SISBA, TMA and the like).

Biological samples from mammals can be conveniently assayed for, e.g., FGF19 mRNAs using Northern, dot blot or PCR analysis. For example, RT-PCR assays such as quantitative PCR assays are well known in the art. In an illustrative embodiment of the invention, a method for detecting FGF19 mRNA in a biological sample comprises producing cDNA from the sample by reverse transcription using at least one primer; amplifying the cDNA so produced using an FGF19 polynucleotide as sense and antisense primers to amplify FGF19 cDNAs therein; and detecting the presence or absence of the amplified FGF19 cDNA. In addition, such methods can include one or more steps that allow one to determine the amount (levels) of FGF19 mRNA in a biological sample (e.g. by simultaneously examining the levels a comparative control mRNA sequence of a housekeeping gene such as an actin family member). Optionally, the sequence of the amplified FGF19 cDNA can be determined.

Probes and/or primers may be labeled with a detectable marker, such as, for example, a radioisotope, fluorescent compound, bioluminescent compound, a chemiluminescent compound, metal chelator or enzyme. Such probes and primers can be used to detect the presence of FGF19 polynucleotides in a sample and as a means for detecting a cell expressing FGF19 proteins. As will be understood by the skilled artisan, a great many different primers and probes may be prepared (e.g., based on the sequences provided in herein) and used effectively to amplify, clone and/or determine the presence or absence of and/or amount of FGF19 mRNAs.

Optional methods of the invention include protocols comprising detection of polynucleotides, such as FGF19 polynucleotide, in a tissue or cell sample using microarray technologies. For example, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment. (see, e.g., WO 01/75166 published Oct. 11, 2001; (See, for example, U.S. Pat. No. 5,700,637, U.S. Pat. No. 5,445,934, and U.S. Pat. No. 5,807,522, Lockart, Nature Biotechnology, 14:1675-1680 (1996); Cheung, V. G. et al., Nature Genetics 21(Suppl):15-19 (1999) for a discussion of array fabrication). DNA microarrays are miniature arrays containing gene fragments that are either synthesized directly onto or spotted onto glass or other substrates. Thousands of genes are usually represented in a single array. A typical microarray experiment involves the following steps: 1. preparation of fluorescently labeled target from RNA isolated from the sample, 2. hybridization of the labeled target to the microarray, 3. washing, staining, and scanning of the array, 4. analysis of the scanned image and 5. generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides, usually 25 mers, are directly synthesized onto a glass wafer by a combination of semiconductor-based photolithography and solid phase chemical synthesis technologies. Each array contains up to 400,000 different oligos and each oligo is present in millions of copies. Since oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligo. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, FGF19 gene deletion, gene mutation, or gene amplification is detected. Gene deletion, gene mutation, or amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., FISH), using an appropriately labeled probe, cytogenetic methods or comparative genomic hybridization (CGH) using an appropriately labeled probe. In addition, these methods may be employed to detect FGF19 ligand gene deletion, ligand mutation, or gene amplification. As used herein, "detecting FGF19 expression" encompasses detection of FGF19 gene deletion, gene mutation or gene amplification.

Additionally, one can examine the methylation status of the FGF19 gene in a tissue or cell sample. Aberrant demethylation and/or hypermethylation of CpG islands in gene 5' regulatory regions frequently occurs in immortalized and transformed cells, and can result in altered expression of various genes. A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found for example in Current Protocols In Molecular Biology, Unit 12, Frederick M. Ausubel et al. eds., 1995; De Marzo et al., Am. J. Pathol. 155(6): 1985-1992 (1999); Brooks et al, Cancer Epidemiol. Biomarkers Prev., 1998, 7:531-536); and Lethe et al., Int. J. Cancer 76(6): 903-908 (1998). As used herein, "detecting FGF19 expression" encompasses detection of FGF19 gene methylation.

The Examples of the present application disclose that FGFR4 is expressed in human primary liver, lung and colon tumors and in colon cancer cell lines, and further that FGF19 and FGFR4 are co-expressed in human primary liver, lung and colon tumors and in colon cancer cell lines. Accordingly, in some embodiments, expression of FGFR4 polypeptide and/or polynucleotide is detected (alone or in conjunction (simultaneously and/or sequentially)) with FGF19 expression) in a biological sample. As described above and in the art, it is presently believed that FGF19 binds to the FGFR4 receptor. Using methods known in the art, including those described herein, the polynucleotide and/or polypeptide expression of FGFR4 can be detected. By way of example, the IHC techniques described above may be employed to detect the presence of one of more such molecules in the sample. As used herein, "in conjunction" is meant to encompass any simultaneous and/or sequential detection. Thus, it is contemplated that in embodiments in which a biological sample is being examined not only for the presence of FGF19, but also for the presence of FGFR4, separate slides may be prepared from the same tissue or sample, and each slide tested with a reagent that binds to FGF19 and/or FGFR4, respectively. Alternatively, a single slide may be prepared from the tissue or cell sample, and antibodies directed to FGF19 and FGFR4 may be used in connection with a multi-color staining protocol to allow visualization and detection of the FGF19 and FGFR4.

In another aspect, the invention provides methods for diagnosing a disorder associated with FGFR4 expression and/or activity, the methods comprising detecting FGFR4 in a biological sample from an individual. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor.

In another aspect, the invention provides methods for diagnosing a disorder associated with FGFR4 and FGF19 expression and/or activity, the methods comprising detecting FGFR4 and FGF19 in a biological sample from an individual. In some embodiments, the FGF19 expression is increased expression or abnormal expression. In some embodiments, FGFR4 expression is increased expression or abnormal expression. In some embodiments, the disorder is a tumor, cancer, and/or a cell proliferative disorder, such as colorectal cancer, lung cancer, hepatocellular carcinoma, breast cancer and/or pancreatic cancer. In some embodiment, the biological sample is serum or of a tumor. In some embodiments, expression of FGFR4 is detected in a first biological sample, and expression of FGF19 is detected in a second biological sample.

In another aspect, the invention provides methods for selecting treatment for an individual, the methods comprising: (a) detecting FGFR4 expression in an individual's biological sample, if any; and (b) subsequence to step (a), selecting treatment for the individual, wherein the selection of treatment is based on the FGFR4 expression detected in step (a). In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 expression is detected and treatment with an anti-FGF19 antibody is selected.

In another aspect, the invention provides methods for selecting treatment for an individual, the methods comprising: (a) detecting FGF19 and FGFR4 expression in the biological sample, if any; and (b) subsequence to step (a), selecting treatment for the individual, wherein the selection of treatment is based on the FGF19 and FGFR4 expression detected in step (a). In some embodiments, increased FGF19 expression in the individual's biological sample relative to a reference value or control sample is detected. In some embodiments, decreased FGF19 expression in the individual's biological sample relative to a reference value or control sample is detected in the individual. In some embodiments, increased FGFR4 expression in the individual's biological sample relative to a reference value or control sample is detected. In some embodiments, decreased FGFR4 expression in the individual's biological sample relative to a reference value or control sample is detected in the individual. In some embodiments, FGFR4 and FGF19 expression are detected and treatment with an anti-FGF19 antibody is selected. In some embodiments, expression of FGFR4 is detected in a first biological sample, and expression of FGF19 is detected in a second biological sample.

In another aspect, the invention provides methods for treating an individual having or suspected of having a cancer, a tumor, and/or a cell proliferative disorder or a liver disorder (such as cirrhosis) by administering an effective amount of an anti-FGF19 antibody, further wherein FGF19 expression and/or FGFR4 is detected in cells and/or tissue from the human patient before, during or after administration of an anti-FGF19 antibody. In some embodiments, FGF19 overexpression is detected before, during and/or after administration of an anti-FGF19 antibody. In some embodiments, FGFR4 expression is detected before, during and/or after administration of an anti-FGF19 antibody. Expression may be detected before; during; after; before and during; before and after; during and after; or before, during and after administration of an anti-FGF19 antibody.

In some embodiments involving detection, expression of FGFR4 downstream molecular signaling is detected in addition to or as an alternative to detection of FGFR4 detection. In some embodiments, detection of FGFR4 downstream molecular signaling comprises one or more of detection of phosphorylation of MAPK, FRS2 or ERK2.

Some embodiments involving detection further comprise detection of Wnt pathway activation. In some embodiments, detection of Wnt pathway activation comprises one or more of tyrosine phosphorylation of β-catenin, expression of Wnt target genes, β-catenin mutation, and E-cadherin binding to β-catenin. Detection of Wnt pathway activation is known in the art, and some examples are described and exemplified herein.

In some embodiments, the treatment is for a cancer selected from the group consisting of colorectal cancer, lung cancer, ovarian cancer, pituitary cancer, pancreatic cancer, mammary fibroadenoma, prostate cancer, head and neck squamous cell carcinoma, soft tissue sarcoma, breast cancer, neuroblastomas, melanoma, breast carcinoma, gastric cancer, colorectal cancer (CRC), epithelial carcinomas, brain cancer, endometrial cancer, testis cancer, cholangiocarcinoma, gallbladder carcinoma, and hepatocellular carcinoma.

Biological samples are described herein, e.g., in the definition of Biological Sample. In some embodiment, the biological sample is serum or of a tumor.

In embodiments involving detection of FGF19 and/or FGFR4 expression, FGF19 and/or FGFR4 polynucleotide expression and/or FGF19 and/or FGFR4 polypeptide expression may be detected. In some embodiments involving detection of FGF19 and/or FGFR4 expression, FGF19 and/or FGFR4 mRNA expression is detected. In other embodiments, FGF19 and/or FGFR4 polypeptide expression is detected using an anti-FGF19 agent and/or an anti-FGFR4 agent. In some embodiments, FGF19 and/or FGFR4 polypeptide expression is detected using an antibody. Any suitable antibody may be used for detection and/or diagnosis, including monoclonal and/or polyclonal antibodies, a human antibody, a chimeric antibody, an affinity-matured antibody, a humanized antibody, and/or an antibody fragment. In some embodiments, an anti-FGF19 antibody described herein is use for detection. In some embodiments, FGF19 and/or FGFR4 polypeptide expression is detected using immunohistochemistry (IHC). In some embodiments, FGF19 expression is scored at 2 or higher using an IHC.

In some embodiments involving detection of FGF19 and/or FGFR4 expression, presence and/or absence and/or level of FGF19 and/or FGFR4 expression may be detected. FGF19 and/or FGFR4 expression may be increased. It is understood that absence of FGF19 and/or FGFR4 expression includes insignificant, or de minims levels. In some embodiments, FGF19 expression in the test biological sample is higher than that observed for a control biological sample (or control or reference level of expression). In some embodiments, FGF19 expression is at least about 2-fold, 5-fold, 10-fold, 20-fold, 30-fold, 40-fold, 50-fold, 75-fold, 100-fold, 150-fold higher, or higher in the test biological sample than in the control biological sample. In some embodiments, FGF19 polypeptide expression is determined in an immunohistochemistry ("IHC") assay to score at least 2 or higher for staining intensity. In some embodiments, FGF19 polypeptide expression is determined in an IHC assay to score at least 1 or higher, or at least 3 or higher for staining intensity. In some embodiments, FGF19 expression in the test biological sample is lower than that observed for a control biological sample (or control expression level).

In some embodiments, FGF19 expression is detected in serum and FGFR4 expression is detected in a tumor sample. In some embodiments, FGF19 expression and FGFR4 expression are detected in a tumor sample. In some embodiments, FGF19 expression is detected in serum or a tumor sample, and FGFR4 downstream molecular signaling and/or FGFR4 expression is detected in a tumor sample. In some embodiments, FGF19 expression is detected in serum or a tumor sample, and Wnt pathway activation is detected in a tumor sample. In some embodiments, FGF19 expression is detected in serum or a tumor sample, and FGFR4 downstream molecular signaling and/or FGFR4 expression and/or Wnt pathway activation is detected in a tumor sample.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

The following materials and methods were used in Examples 1-12.

Gene Expression

Total RNA from frozen tissue samples was extracted using RNA STAT-60 according to the manufacturer's protocol (Tel-test "B" Inc.). Total RNA from cultured cells was isolated with RNeasy kit using the manufacturer's protocol (Qiagen). The contaminating DNA was removed using the DNA-free kit (Ambion; cat#1906)) and the samples were used for real-time PCR. Specific primers and fluorogenic probes for human FGF19, FGFR4 and RPL19 mRNAs (Table 2) were designed using Primer Express 1.1 (PE Applied Biosystems) and used to quantify gene expression. The gene specific signals were normalized to the signal of the RPL19 housekeeping gene. Triplicate sets of data were averaged for each condition.

TABLE 2

| | Forward Primer | Reverser Primer | Probe |
|---|---|---|---|
| CYP7α1 | CCATGATGCAAAACCTCCAAT (SEQ ID NO: 11) | ACCCAGACAGCGCTCTTTGA (SEQ ID NO: 12) | TGTCATGAGACCTCCGGGCCTTCC (SEQ ID NO: 13) |
| GAPDH | AATTTGCCGTGAGTGGAGTC (SEQ ID NO: 14) | CAGTGGCAAAGTGGAGATTGT (SEQ ID NO: 15) | CCATCAACGACCCCTTCATTGACCTC (SEQ ID NO: 16) |
| FGF19 | AGACCCCAAGTCTTGTCAATAAC (SEQ ID NO: 17) | AATATCATGTTGGAAAACCAAGTG (SEQ ID NO: 18) | CCGCTGCTTCCACACAGCAA (SEQ ID NO: 19) |
| FGFR4 | GCTCTTGACGGGAGCATT (SEQ ID NO: 20) | CGCCATTTGCTCCTGTTT (SEQ ID NO: 21) | GCAGGCTTCCAGCTTCTC (SEQ ID NO: 22) |
| RPL19 | AGCGGATTCTCATGGAACA (SEQ ID NO: 23) | CTGGTCAGCCAGGAGCTT (SEQ ID NO: 24) | TCCACAAGCTGAAGGCAGACAAGG (SEQ ID NO: 25) |

In Situ Hybridization $^{33}$P-UTP labeled sense or antisense probes corresponding to human FGFR4 (nucleotides 435 to 1183 of NM_022963) or FGF19 (nucleotides 495 to 1132 of NM 005117) were generated by polymerase chain reaction (Mauad et al. (1994) Am J Pathol 145, 1237-1245). Sections were deparaffinized, deproteinated in 4 mg/ml of proteinase K for 30 min at 37° C., and further processed for in situ hybridization (Holcomb et al. (2000) Embo J 19, 4046-4055). Probes were hybridized to the sections at 55° C. overnight and unhybridized probes were removed by RNAse A treatments. The slides were dipped in NBT2 emulsion (Eastman Kodak), exposed for 4 weeks at 4° C., developed and counterstained with hematoxylin and eosin.

Immunoprecipitation and Immunoblotting

Tissue samples (50 mg) were homogenized in 500 µl extraction buffer (20 mM Tris pH 8, 137 mM NaCl, 1 mM EGTA, 1% Triton X-100, 10% glycerol, 1.5 mM $MgCl_2$, complete protease inhibitor cocktail (Roche Applied Sciences)). Total proteins from cultured cells were extracted on ice for 30 min with the extraction buffer. Lysates were centrifuged (10,000×g, 15 min) and then cleared with Cibacron blue-agarose and Protein G-agarose (GE Healthcare Life Sciences) overnight at 4° C. Lysates (100 µg protein) were incubated in 1 ml PBS/0.1% Triton with 2 ug of the agarose coupled antibodies of interest for 1 h at 4° C. The gel slurry was washed with the same buffer and eluted with 10 µl Elution buffer (Pierce Biotechnology). Samples were analyzed by Westerns blot using 2 ug of biotinylated FGF19 antibody (BAF969; R&D systems), FGFR4 antibody (Genentech, Inc.) and IRDye 800 conjugated secondary reagents and visualized using the Odyssey scanner (L1-Cor Biotechnology).

Immunohistochemistry

Formalin fixed paraffin embedded tissue sections were treated for antigen retrieval using Trilogy (Cell Marque) and then incubated with 10 ug/ml FGF19 antibody (1D1; Genentech Inc). The immunostaining was accomplished using a biotinylated secondary antibody, an ABC-HRP reagent (Vector Labs) and a metal-enhanced DAB colorimetric peroxydase substrate (Pierce Laboratories).

Cell Migration Assay

The surface of 8 µm porosity 24-well format PET membrane filters (BD Biosciences) was coated overnight at 4° C. with 50 µl of type 1 collagen (50 µg/ml; Sigma) in 0.02 M acetic acid. Cells ($5 \times 10^4$) in serum free minimal essential medium containing 0.1% BSA were added to the upper chamber. The lower chamber was filled with the same media and the plates were incubated at 37° C. The next day the upper chamber was wiped with a cotton swab and the cells that migrated to the lower side of the insert were stained and counted under a microscope. Triplicate sets of data were averaged for each condition.

Solid Phase Receptor Binding Assay

Maxisorb 96 well plates were coated overnight at 4° C. with 50 µl of 2 µg/ml anti-human immunoglobulin Fcγ fragment specific antibody (Jackson Immunoresearch) and used to capture 1 µg/ml FGFR-Fc chimeric proteins (R & D Systems). The non-specific binding sites were saturated with PBS/3% BSA and FGF19 was incubated for 2 h in PBS/0.3% BSA in the presence of glycosaminoglycans (Seikagaku Corporation) or oligosaccharides (Neoparin Inc.). FGF19 binding was detected using a biotinylated FGF19 specific polyclonal antibody (BAF969; R & D Systems) followed by streptavidin-HRP and TMB colorimetric substrate.

Receptor Pull Down Assay

FGFR-Fc chimeric proteins (400 ng) were incubated with 400 ng FGF19 or 400 ng FGF1 and heparin (200 ng) in 50:50

Dulbecco's Modified Essential Media:Ham F12 containing 10 mM HEPES pH 7.4 and 0.1% BSA for 1 h. Protein G-agarose (20 µl) was added and further incubated for 30 min. The matrix was washed with PBS/0.1% Triton-X100, eluted with SDS-PAGE sample buffer containing reducing agent and analyzed by Western blot using biotinylated FGF19 antibody (BAF969) or biotinylated FGF1 antibody (BAF232; R&D systems).

HSPG Solid Phase Binding Assay

Heparan sulfate proteoglycan (Sigma) was adsorbed to Maxisorb 96 well plates overnight at 4° C. The non-specific binding sites were saturated with PBS/3% BSA and the wells were incubated with FGF19 or FGF1 (1:3 serial dilutions from 1 ug/ml to 0.00017 ug/ml) (R & D Systems) for 1 h. The non-specific binding was determined in the presence of an excess of heparin (10 ug/ml). The binding was detected with biotinylated specific antibodies and TMB colorimetric substrate. The specific binding was calculated by subtracting the non-specific binding from the total binding.

Heparin Agarose Binding Assay

FGF19 and FGF1 protein (each at 400 ng/ml) were incubated with 20 µl heparin-agarose (GE Healthcare Life Sciences) in 50:50 Dulbecco's Modified Essential Media:Ham F12 containing 10 mM HEPES pH 7.4 and 0.1% BSA for 1 h. The gel slurry was washed with 1 ml of 20 mM Tris pH 7.4 containing various NaCl concentrations and then with 1 ml of the same buffer containing 20 mM NaCl. The bound proteins were eluted with SDS PAGE sample buffer containing reducing agent and analyzed by Western blot.

Generation of FGF19 Monoclonal Antibodies

Balb/c mice were sequentially immunized with FGF19-His. In particular, Balb/c mice were immunized into each hind footpad 9 times (at two week intervals) with 2.0 µg of hu FGF-19-His resuspended in MPL-TDM (Ribi Immunochemical Research, Inc., Hamilton, Mont.). Three days after the final boost, spleens were harvested and popliteal lymph node cells were fused with murine myeloma cells P3X63Ag8.U.1 (ATCC CRL1597), using 35% polyethylene glycol. Hybridomas were selected in HAT medium. Ten days after the fusion, hybridoma culture supernatants were screened for mAbs binding to the hu FGF-19 by ELISA. Cell lines producing antibodies against human FGF-19 were cloned twice by limiting dilution. Selected FGF19 antibody producing hybridomas were subcloned twice to insure monoclonality. The clones were inoculated for ascites production and antibodies were purified by protein A-agarose affinity chromatography.

Total RNA was extracted from hybridoma cells producing the antibodies, using standard methods. The variable light (VL) and variable heavy (VH) domains were amplified using RT-PCR with the degenerate primers to heavy and light chain. The forward primers were specific for the N-terminal amino acid sequence of the VL and VH region. Respectively, the LC and HC reverse primers were designed to anneal to a region in the constant light (CL) and constant heavy domain 1 (CH1), which is highly conserved across species. Amplified VL and VH were cloned into mammalian expression vectors. The polynucleotide sequence of the inserts was determined using routine sequencing methods.

Analysis of Antibody Binding Affinity and Kinetics

For binding kinetics, Surface Plasmon Resonance (SRP) measurement with a BIAcore™-3000 was used (BIAcore, Inc., Piscataway, N.J.). Briefly, carboxymethylated dextran biosensor chips (CMS, BIAcore Inc.) were activated with N-ethyl-N'-(3-dimethylaminopropyl)-carbodiimide hydrochloride (EDC) and N-hydroxysuccinimide (NHS) according to the supplier's instructions. Anti-FGF19 or FGFR4 antibody was diluted with 10 mM sodium acetate, pH 4.8, into 5 ug/ml before injected at a flow rate of 5 ul/minute to achieve approximately 500 response units (RU) of coupled antibody. Next, 1M ethanolamine was injected to block unreacted groups. For kinetics measurements, two-fold serial dilutions of either FGF19-His or FGFR4 molecules (0.7 nM to 500 nM) were injected in PBS with 0.05% Tween 20 at 25'C at a flow rate of 25 ul/min. Association rates ($k_{on}$) and dissociation rates ($k_{off}$) were calculated using a simple one-to-one Langmuir binding model (BIAcore Evaluation Software version 3.2). The equilibrium dissociation constant ($K_d$) was calculated as the ratio $k_{off}/k_{on}$.

Antibody Epitope Excision

FGF19 protein (10 µg) was incubated for 2 h in 50 mM Tris, pH 7.4 with 50 µl of agarose coupled-antibody. The resin was washed and digested with 0.1 µg trypsin (Promega) overnight at 37° C. in 100 mM ammonium bicarbonate pH 8. The gel slurry was washed and the bound peptides were eluted with 10% trifluoroacetic acid (TFA) and analyzed by MALDI-TOF-MS (Voyager; Applied Biosystems). Candidate peptides were subjected to collision induced dissociation (QSTAR) and manually sequenced to confirm the peptide mass mapping identification (FIG. S1).

Solid Phase Antibody Binding Assay

Non-specific binding sites of HisGrab Nickel coated plates (Pierce) were saturated with PBS/3% BSA. The wells were incubated with 1 µg/ml FGF19-His in PBS/0.3% BSA for 1 h. The plates were washed and incubated for 1 h with FGF19 antibodies (at concentrations ranging from 1 ug/ml to 0.000017 ug/ml) in the presence or the absence of FGF19 peptides in PBS/0.3% BSA. The bound antibodies were detected using a HRP conjugated anti-mouse IgG (Jackson Immunoresearch) and the TMB peroxydase colorigenic substrate (KPL).

CYP7α1 Expression Analysis

HEP3B cells were starved overnight in serum free Dulbecco's Modified Essential Media:Ham F12 (50:50) and treated with 100 ng/ml FGF19 for 6 h in the presence or the absence of antibodies 1A6, 1A1 or isotype-matched control antibody (each at concentrations ranging from 10 ug/ml to 0.04 ug/ml). CYP7α1 expression was evaluated by semi-quantitative RT-PCR using gene specific primers and probes (Taqman ABI PRISM 7700, Applied Biosystems) and normalized to GAPDH expression. Triplicate sets of data were averaged for each condition.

FGFR4/MAPK Phosphorylation

HEP3B cells starved overnight in serum free media were treated with 40 ng/ml FGF19 for 10 mM in the presence or the absence of antibodies. Cells were lysed in R27A buffer (Upstate) supplemented with 10 mM NaF, 1 mM sodium orthovanadate, and Complete protease inhibitor tablet (Roche). Lysates were prepared, electrophoresed and analyzed by Western blot using phospho-FRS2, phospho-MAPK and MAPK specific antibodies (Cell Signaling) and FRS2 specific antibody (Santa Cruz).

Xenograft Experiments

All animal protocols were approved by an Institutional Animal Care and Use Committee. Six- to eight-week-old athymic BALB/c female mice (Charles Rivers Inc.) were inoculated subcutaneously with $5 \times 10^6$ cells (200 µl/mouse). After 7 days, mice bearing tumors of equivalent volumes (~100 mm$^3$) were randomized into groups (n=10) and treated intraperitoneally twice weekly. Tumors were measured with an electronic caliper (Fowler Sylvac Ultra-Cal Mark III) and average tumor volume was calculated using the formula: (W2×L)/2 (W, the smaller diameter; L, the larger diameter).

The statistical difference was analyzed using the Student's t-test for normal distribution. Values of P<0.05 were considered significant.

FGFR4, FRS2, and β-Catenin Phosphorylation in Xenograft Tumors

Tumors excised from control (gp120) and anti-FGF19 (1A6) antibodies treated animals were homogenized in lysis buffer containing 50 mM Tris-HCl, pH 7.5, 150 mM NaCl, 1% NP-40, 1 mM EDTA, 0.25% sodium deoxycholate, 1 mM NaF, 1 mM sodium orthovanadate, and mini protease inhibitor tablet (Roche). Protein concentrations of the lysates were determined using the BCA protein assay reagent (Pierce). Equal amounts of proteins (100 μg protein) were incubated with 1 μg of anti-FGFR4 antibody (clone 1G7; Genentech inc.) or anti-FRS2 (UpState) antibody immobilized onto protein A-Sepharose for 2 h at 4° C. with gentle rotation. Matrix was washed with lysis buffer and immunocomplexes eluted in 2× Laemmli buffer, boiled, and microcentrifuged. Proteins were electrophoresed on SDS-PAGE, transferred to nitrocellulose membrane, and probed with phosphotyrosine antibody (1:1000 dilution, 4G 10, UpState). After washing and incubating with secondary antibody, immunoreactive proteins were visualized by the ECL detection system (Amersham). ERK2 phosphorylation levels were assessed without prior immunoprecipitation using phospho-ERK2 antibody (1:1000 dilution, Santa Cruz Biotech) and β-catenin phosphorylation was assessed without prior immunoprecipitation using an antibody directed against N-terminally dephosphorylated β-catenin (1:1000 dilution, UpState). Membranes were stripped (Pierce) and reprobed with appropriate antibodies to determine total protein.

Micro-CT Imaging and Analysis of Hepatocellular Carcinomas in FGF19 TG Mice

Liver tumors were identified by micro-ct imaging with Fenestra-LC, a liver specific contrast agent. Fenestra-LC is an iodinated triglyceride that mimics chylomicron remnants and exploits endogenous lipid metabolic pathways resulting in hepatocyte contrast accumulation. These agents have been previously been previously employed as means to identify hepatic liver tumors. (Lee et al., 1997; Weichert et al., 1996) At 6-months of age, FGF19 transgenic mice were injected with Fenestra LC (Advanced Research Technologies Inc. Saint-Laurent, Quebec, Canada), 20 μl/g iv, and a conscious 3-hour hepatic uptake was allowed before mice were euthanized and livers resected for gross analysis, weighing, ex-vivo micro-CT analysis (μCT 40 system; Scanco Medical, Bassersdorf, Switzerland), and histological staining. Whole livers were lightly blotted on gauze and submerged in soybean oil (Sigma-Aldrich, St. Louis, Mo.) in preparation for micro-CT imaging. For each liver, 90-minute scans were obtained at 30-μm isotropic voxel size, with 512 projections at an integration time of 300 ms, energy of 45 keV, and tube current of 177 μA. Volumetric image files were analyzed using image analysis software from AnalyzeDirect (Lenexa, Kans.). An intensity threshold of −16 Houndsfield Units (HU) was used to segment the tissue mass from the background signal (soybean oil). A second threshold (26 HU) was employed to estimate hepatic tissue volumes associated with functional hepatic tissue that accumulated the contrast agent resulting in hyper-intense regions defining normal hepatic tissue. Hepatic tissues of FGF19 transgenic mice where there was minimal attenuation due to small contrast agent concentrations, including vasculature, gall bladder and biliary ducts, and hepatocellular carcinomatous lesions, appeared less intense. An average of the total low-intensity hepatic volumes from wild-type FVB mice, which did not have hepatocellular carcinomas, was subtracted from both the FGF19 transgenic control and treated groups to obtain volumes associated only with tumors. Data are expressed as a percentage of tumor volume of total liver volume.

Statistical Analysis

Statistical significance was analyzed using the unpaired two-tailed Student's t-test. Values of P<0.05 were considered significant. Data are expressed as the mean±s.e.m.

The following materials and methods were used in Examples 13-17:

Cells

HCT116 cells (ATCC, Rockville, Md.) were routinely maintained at 37° C. and 5% $CO_2$ in RPMI 1640 containing 10% tetracycline-free fetal bovine serum and 4 mmol/L L-glutamine. Serum-starved cells were incubated with either vehicle or FGF19 (25-100 ng/ml, 10 min). In separate experiments, cells were treated with either control antibody (gp120) or FGF19 antibody (1A6, 10 μg/ml) for 3-24 hrs. To further evaluate the effects on β-catenin activation, cells were pretreated with a proteasome inhibitor, MG132 (Biomol, Plymouth Meeting, Pa.) at 1 μM concentration for 4 hr followed by anti-FGF19 mab 1A6 treatment for 24 hrs to evaluate phosphorylation of Ser33/Ser37, Ser 45 and Thr41 on β-catenin. After incubation, cells were washed in cold PBS and lysed for either protein or RNA analysis.

Immunoprecipitation and Western Blot Analysis

Cells were lysed in modified RIPA buffer (50 mM Tris-Cl, pH 7.5; 150 mM NaCl; 1% IGEPAL; 1 mM EDTA; 0.25% sodium deoxycholate; 1 mM NaF; 1 mM $Na_3VO_4$; protease inhibitors cocktail (Sigma-Aldrich, St. Louis, Mo.) and clarified by centrifugation. Protein concentrations of the lysates were determined using the BCA protein assay reagent (Pierce, Rockford, Ill.). Equal amounts of proteins were incubated with specific antibody immobilized onto protein A-Sepharose (Sigma-Aldrich) for 2 hours at 4° C. with gentle rotation. Beads were washed extensively with lysis buffer and immunecomplexes were eluted in 2× Laemmli buffer, boiled and microcentrifuged. Proteins were resolved on SDS-PAGE, transferred to nitrocellulose membrane and incubated with specific primary antibodies. After washing and incubating with secondary antibodies, immunoreactive proteins were visualized by the ECL detection system (Amersham, Arlington Ht. IL), The antibodies used for immunoprecipitation and immunoblotting were anti-β-catenin mAbs from BD Transduction (San Diego, Calif.), anti-active-β-catenin antibody directed against N-terminally dephosphorylated β-catenin, anti-phosphotyrosine (4G10) and anti-E-cadherin antibody from UpState Biotech (Charlottesville, Va.), anti-phospho-β-catenin (Ser33/Ser37 and Ser45/Thr41 specific) antibody from Cell Signaling (Danvers, Mass.), and anti-FGFR4 mAb (1G7) (Genentech, Inc.). Where indicated, the membranes were stripped (Pierce) and reprobed with another antibody. The densities of specific protein bands were analyzed using Adobe Photoshop cs2 version 9 (Adobe Systems, Mountain View, Calif.). Quantitative analyses of tyrosine and Ser/Thr phosphorylation of β-catenin and E-cadherin were performed by determining the ratio between total protein and the phosphorylation by using the data from three separate experiments.

Liquid Chromatography-Mass Spectrometry/Mass Spectrometry (LC-MS/MS)

Indirect quantification of N-terminal β-catenin phosphorylation levels was performed using linear ion trap mass spectrometry. β-catenin was immunoprecipitated from cells pretreated with MG132 followed by treatment with control (gp120) or anti-FGF19 mab 1A6, and separated using Tris-Gly SDS PAGE. Gels were Coomassie stained and the β-catenin bands were cut out and reduced in 10 mM DTT for 30 min room temperature and cysteines were alkylated with 50 mM iodoacetamide 15 min at room temperature before tryptic digestion. The peptides were digested in trypsin (10 ng/μl) in 50 mM sodium bicarbonate pH 8.0 and peptide mixtures (3 mL) were loaded onto a 0.25×30 mm trapping cartridge packed with Vydac 214MS low-TFA C4 beads. This cartridge was placed in-line with a 0.1×100 mm resolving column packed with Vydac 218MS C18 beads. The resolving column was constructed using a "picofrit" (New Objective) fused silica capillary pulled to a 15 mm metal-coated tip, which formed a micro-electrospray emitter. Peptides were eluted with 1 hour gradients of acetonitrile containing 0.1% formic acid at a rate of 0.3 mL/min. Data dependent tandem mass spectrometry was performed using a linear ion trap instrument (LTQ; Finnigan). The Sequest database searching program was used to generate cross correlation scores for each CID spectrum. Proteins matched by only a single peptide were confirmed by manual interpretation of the collision-induced dissociation spectra. Phosphorylated peptides were manually confirmed. Peak areas were then integrated to determine relative abundance of peptides.

Wnt-Target Gene Expression Analyses

Total RNA was isolated using the Qiagen RNA isolation kit (Qiagen, CA) and DNase treated (Applied Biosystems, Foster City, Calif.) following the manufacturer's protocol. RNA concentration was determined using ND-1000 spectrophotometer (Wilmington, Del.). Real-time quantitative PCR was performed to determine the relative abundance of Wnt-target gene (cyclin D1, CD44, E-cadherin, c-jun) mRNAs. Probes were labeled with FAM (5' end) and TAMRA (3' end). The primers and probe sequences were as follows:

```
human cyclin D1 Forward:
                                           (SEQ ID NO: 26)
GCT GCT CCT GGT GAA CAA GC;

Reverse:
                                           (SEQ ID NO: 27)
TGT TCA ATG AAA TCG TGC GG;

Probe:
                                           (SEQ ID NO: 28)
CAA GTG GAA CCT GGC CGC AAT GAC;

human CD44 Forward:
                                           (SEQ ID NO: 29)
GAA AAA TGG TCG CTA CAG CAT CT;

Reverse:
                                           (SEQ ID NO: 30)
GGT GCT ATT GAA AGC CTT GCA;

Probe:
                                           (SEQ ID NO: 31)
CGG ACG GAG GCC GCT GAC C;

human E-cadherin Forward:
                                           (SEQ ID NO: 32)
GAC TTG AGC CAG CTG CAC AG;

Reverse:
                                           (SEQ ID NO: 33)
GTT GGT GCA ACG TCG TTA CG;

Probe:
                                           (SEQ ID NO: 34)
CCT GGA CGC TCG GCC TGA AGT G;

human c-jun Forward:
                                           (SEQ ID NO: 35)
CGT TAA CAG TGG GTG CCA ACT;

Reverse:
                                           (SEQ ID NO: 36)
CCC GAC GGT CTC TCT TCA AA;

Probe:
                                           (SEQ ID NO: 37)
ATG CTA ACG CAG CAG TTG CAA ACA;

Human specific ribosomal protein L-19 (RPL-19):
Forward:
                                           (SEQ ID NO: 38)
AGC GGA TTC TCA TGG AAC A;

Reverse:
                                           (SEQ ID NO: 39)
CTG GTC AGC CAG GAG CTT;

Probe:
                                           (SEQ ID NO: 40)
TCC ACA AGC TGA AGG CAG ACA AGG.
```

Amplification reactions (50 μl) contained 100 ng of RNA template, 5 mmol/L of MgCl2, 1× buffer A, 1.2 mmol/L of dNTPs, 2.5 U of TaqGold polymerase, 20 U of RNase inhibitor, 12.5 U of MuLV reverse transcriptase, 2 mmol/L each forward and reverse primer, and 5 μmol/L of probe (Perkin Elmer). Thermal cycle (Perkin Elmer ABI Prism 7700 sequence detector) conditions were 48° C. for 30 minutes, 95° C. for 10 minutes, and 95° C. for 15 seconds, and 60° C. for 1 minute for 40 cycles. Analyses of data were performed using Sequence Detector 1.6.3 (PE Applied Biosystems) and results for genes of interest were normalized to the RPL19 gene.

ShRNA Studies

The pHUSH inducible vector system comprising a shRNA expression shuttle plasmid and a viral vector backbone containing a TetR-IRES-Puro cassette was used (Hoeflich, K P et al, Cancer res 66:999-1006 (2006)). FGFR4 knockdown vectors were constructed by designing custom siRNA sequences, converting them into shRNA, and testing their efficacy in transient co-transfection experiment in 293T cells. The following shRNA sequences were cloned into pShuttle-H1 and then H1-shRNA cassette was transferred into pHUSH-GW by a Gateway (Invitrogen, Carlsbad, Calif.) recombination reaction:

```
FGFR4 shRNA2 Forward:
                                           (SEQ ID NO: 41)
GAT CCC CCT CGT GAG TCT AGA TCT ATT CA AGA GAT
AGA TCT AGA CTC ACG AGG TTT TTT GGA AA;

Reverse:
                                           (SEQ ID NO: 42)
AGC TTT TCC AAA AAA CCT CGT GAG TCT AGA TCT ATC
TCT TGA ATA GAT CTA GAC TCA CGA GGG GG;

FGFR4 shRNA5 Forward:
                                           (SEQ ID NO: 43)
GAT CCC CGA ACC GCA TTG GAG CA TTA TCA AGA GAA
ATG CCT CCA ATG CGG TTC TTT TTT GGA AA;

Reverse:
                                           (SEQ ID NO: 44)
AGC TTT TCC AAA AAA GAA CCG CAT TGG AGG CAT TTC
TCT TGA TAA TGC CTC CAA TGC GGT TCG GG;
```

-continued hEGFP control Forward:
(SEQ ID NO: 45)
GAT CCC CGC AGC ACG ACT TCT TCA AGT TCA AGA GAC
TTG AAG AAG TCG TGC TGC TTT TTT GGA AA;

Reverse:
(SEQ ID NO: 46)
AGC TTT TCC AAA AAA GCA GCA CGA CTT CTT CAA GTC
TCT TGA ACT TGA AGA AGT CGT GCT GCG GG.

All constructs were verified by sequencing.

Generation of Inducible-shRNA Cell Clones

HCT116 cells were transfected using LipofectAmine 2000 plus (Invitrogen). As the puromycin resistance gene encoded in the vector is under the control of a constitutive β-actin promoter, 5 µg/mL puromycin was used to select transfected cells expressing shRNA. Stable clones were isolated, treated with 1 µg/mL doxycycline (BD Clontech, San Jose, Calif.) for 7 days to induce expression of siRNA. Functional FGFR4 protein knockdown was assessed by Western blotting.

Statistical Analysis

Student's two-tailed t test was used to compare data between two groups. One-way analysis of variance and Dunnett's test were used to compare data between three or more groups. P-value <0.05 was considered statistically significant.

Example 1

Analysis of FGF19 and FGFR4 Expression in Human Tissues

Figure 2A:
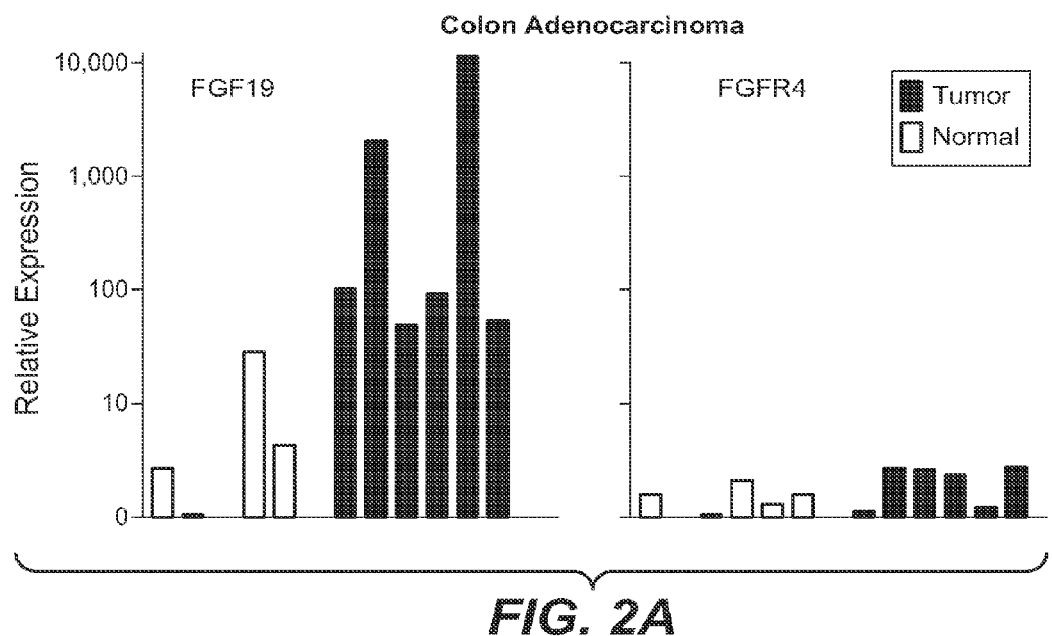
FIG. 2: FGF19 and FGFR4 mRNA expression in normal and tumor samples from colon (A) and lung (B) were evaluated by semi quantitative RT-PCR. Values were normalized using GAPDH expression and compared to the lowest expressing sample for each tissue. Representative images of bright-field (left panels) and dark-field (right panels) illumination of in situ hybridization with FGF19 and FGFR4 riboprobes and FGF19 immunohistochemistry (IHC) (lower panels) in colon adenocarcinoma (C), lung squamous cell carcinoma (D), and hepatocellular carcinoma (E). Representative images of bright-field (top left panel) and dark-field (top right panels) illumination of in situ hybridization with the FGF19 riboprobe and FGF19 IHC (lower panels) in cirrhotic liver nodules (F).
Figure 2B:
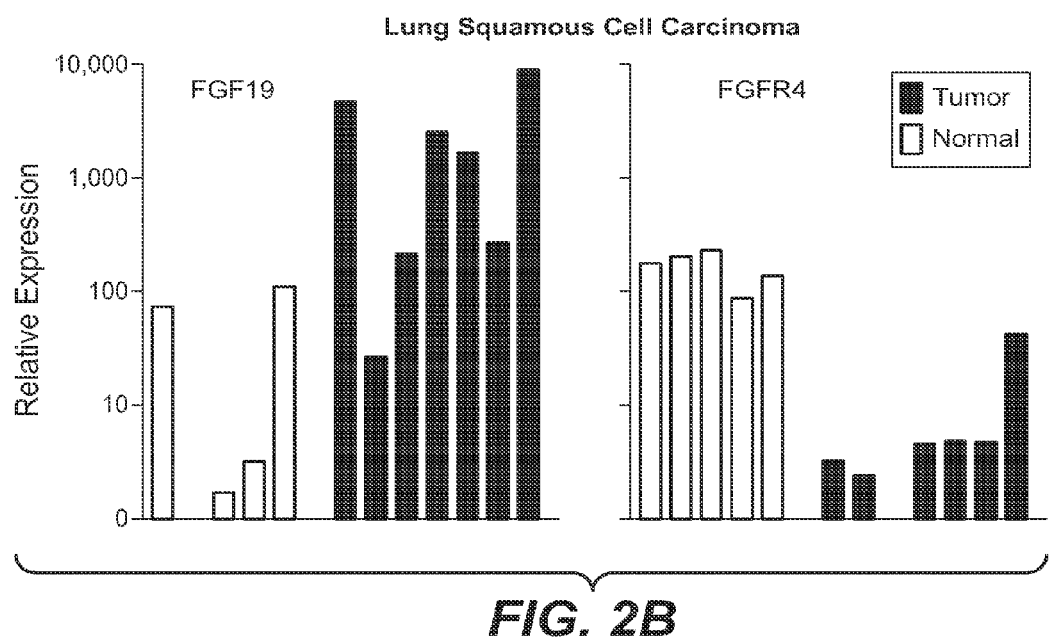

FGF19 and FGFR4 protein expression was evaluated in human colon adenocarcinomas, lung squamous cell carcinomas (SCC), and hepatocellular carcinomas (HCC). FGF19 was overexpressed in 6 out of 10 colon adenocarcinomas (FIG. 2A) and in 7 out of 10 lung SCC relative to normal tissues (FIG. 2B). Compared to normal tissues, FGFR4 expression was not significantly altered in colon tumors but appeared downregulated in SCC (FIGS. 2A and 2B).

Figures 2C, 2D:
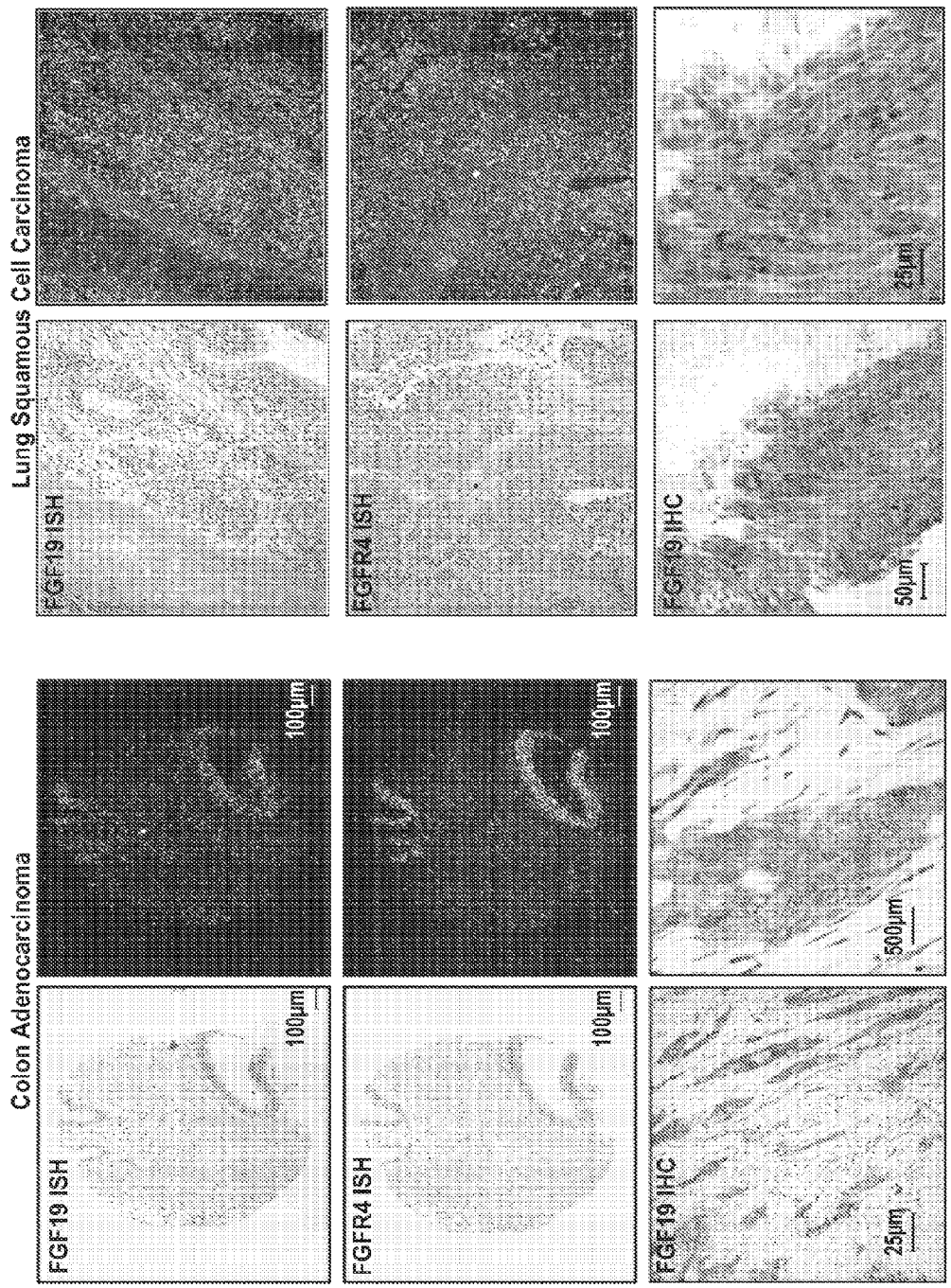

To localize FGF19 and FGFR4 mRNA expression in tumor tissues, we performed in situ hybridization. Messenger RNA for both genes was prominent in neoplastic epithelial cells in colon adenocarcinomas and lung SCC (FIGS. 2C and D). In a tissue microarray comprised of 35 colon adenocarcinoma cases, 26 (74%) had positive signal for FGF19 mRNA and 27 (77%) had positive signal for FGFR4 mRNA. Treatment with anti-FGF19 antibody targets both non-tumor-derived FGF19 and tumor-derived FGF19, and thus anti-FGF19 treatment may have clinical benefit in FGFR4-positive tumors that lack FGF19 expression. Table 3 shows the presence or absence of co-expression of FGFR4 and/or FGF19 mRNAs in the colon adenocarcinoma tissue microarray samples:

TABLE 3

| | Colon Adenocarcinoma | |
|---|---|---|
| | FGFR4+ | FGFR4− |
| FGF19+ | 21 (60%) | 5 (14%) |
| FGF19− | 6 (17%) | 3 (9%) |

Figures 2E, 2F:
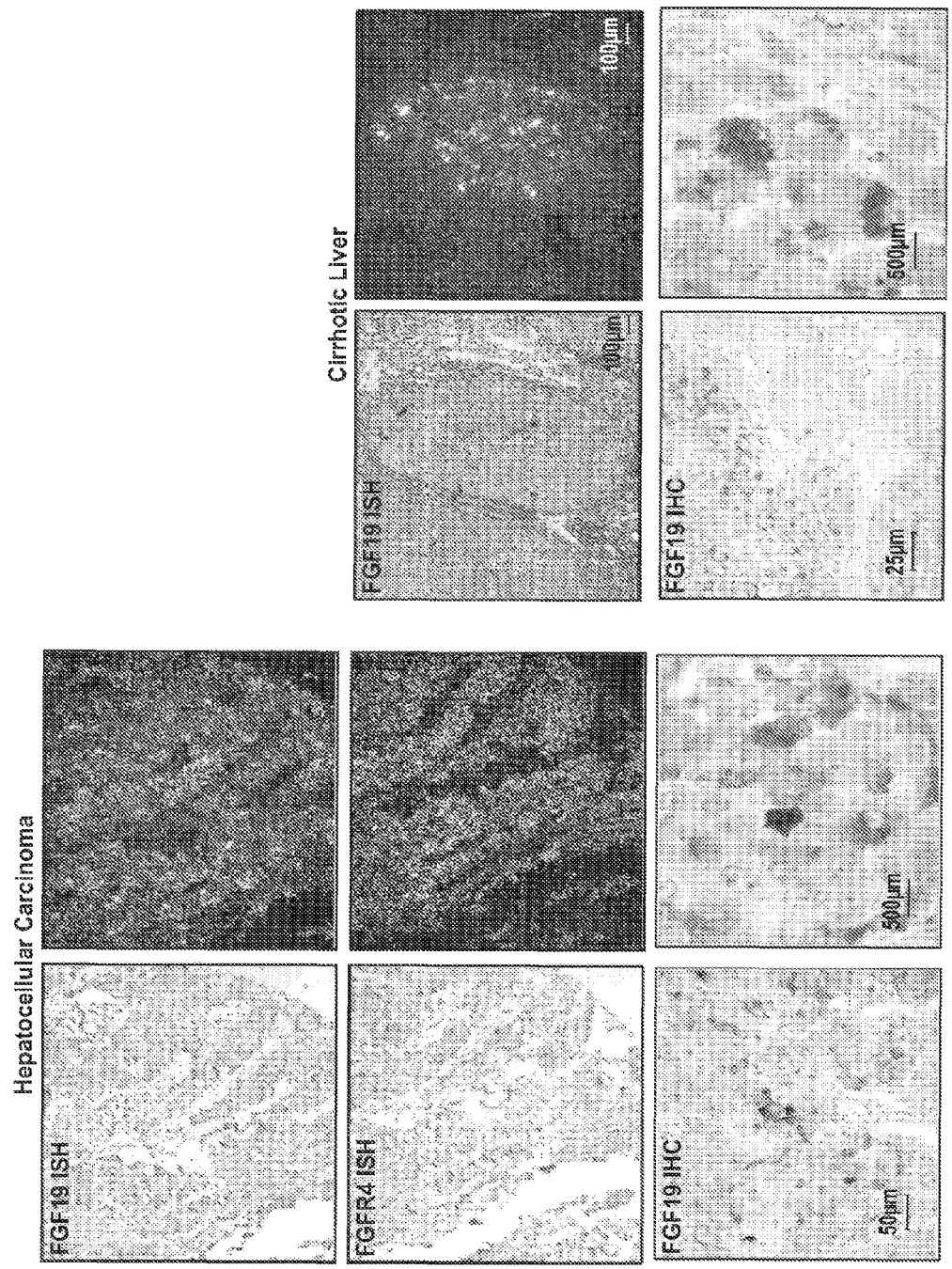

Overlap between the presence of FGF19 and FGFR4 in colon adenocarcinomas was observed in a majority of tumor samples. Of 14 lung SCC cases, 14 (100%) had positive signal for FGF19 mRNA and 13 (93%) had positive signal for FGFR4 mRNA. In addition, neoplastic epithelial cells showed strong FGF19 protein staining by immunohistochemistry in both colon adenocarcinomas (FIG. 2C) and lung SCC (FIG. 2D). These relatively high expression frequencies suggested a significant overlap between the presence of FGF19 and FGFR4 in lung SCCs. Because systemic FGF19 expression in transgenic mice promotes hepatocellular carcinomas (HCC) (Nicholes et al., 2002), we also evaluated FGF19 and FGFR4 mRNA expression in liver samples. Of 50 cases of hepatocellular carcinoma, 23 (46%) demonstrated positive signal for FGF19 mRNA and 30 (60%) for FGFR4 mRNA. Both genes were expressed in the neoplastic hepatocytes (representative examples shown in FIG. 2E). The neoplastic hepatocytes also showed strong FGF19 protein staining by immunohistochemistry (FIG. 2E). Table 4 shows the presence or absence of co-expression of FGFR4 and/or FGF19 mRNAs in the colon adenocarcinoma tissue microarray samples:

TABLE 4

| | HCC | |
|---|---|---|
| | FGFR4+ | FGFR4− |
| FGF19+ | 21 (41%) | 4 (8%) |
| FGF19− | 11 (22%) | 15 (29%) |

Overlap between FGFR4 and FGF19 expression was observed in a large percentage of samples.

These results showed that FGF19 and FGFR4 are expressed in several types of human cancers.

Because cirrhosis often precedes hepatocellular carcinoma, FGF19 mRNA expression was evaluated in cirrhotic liver. These samples showed strong FGF19 mRNA and protein signals in regenerative nodule hepatocytes (FIG. 2F), suggesting that FGF19 expression occurs early during liver neoplastic progression.

FGF19 mRNA expression was also evaluated in several types of primary epithelial tumors by in situ hybridization. FGF19 mRNA expression was detected in 16/38 (42%) cases of breast adenocarcinoma, 39/70 (56%) cases of ovarian adenocarcinoma, and 8/79 (10%) cases of pancreatic adenocarcinoma. These results showed that FGF19 mRNA was expressed in several types of primary tumor. In addition, a panel of colon adenocarcinoma was screened for expression of FRFR4 protein using immunohistochemistry, and 18/20 samples were positive for FGFR4 expression.

Example 2

FGF19 and FGFR4 are Expressed in Human Tumor Cell Lines and Xenograft Tissues

Figure 3A:
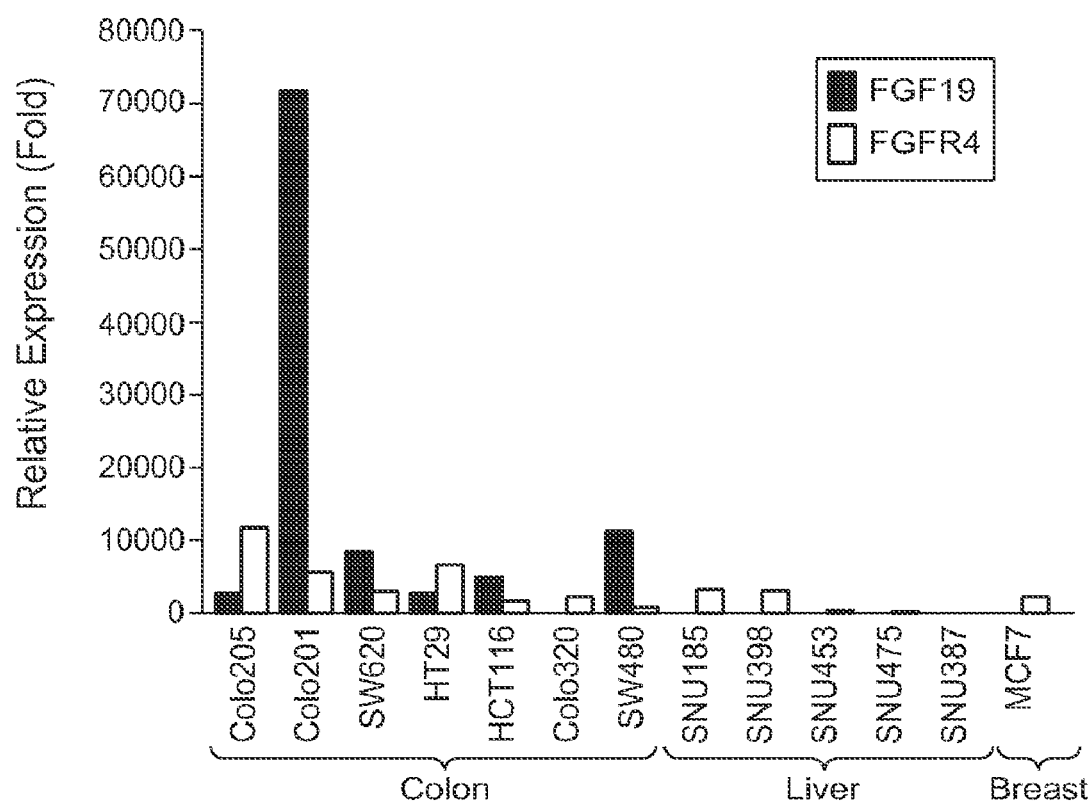
FIG. 3: FGF19 and FGFR4 mRNA and protein expression in tumor cell lines and xenograft tissue. (A) FGF19 and FGFR4 mRNA had high relative expression in colon tumor cell lines, Colo205, SW620, and HCT116. FGF19 and FGFR4 mRNA expression were evaluated using semi-quantitative RT-PCR. Values were normalized using GAPDH expression and compared to the lowest expressing cell line for each gene. (B) Western blot of FGF19 and FGFR4 protein expressed in a panel of colon cancer cell lines. FGF19 protein expression was confirmed in colon cancer cell lines by immunoprecipitation and western blot analysis. (C), (D) A subset of colon cancer cell lines was inoculated subcutaneously in nude mice. After 3 weeks, tumors were excised and processed for FGF19 immunostaining. Pictures of representative fields at 400× (C) and 400× with an inset of 600× (bar=25 µm) (D) are shown.
Figure 3B:
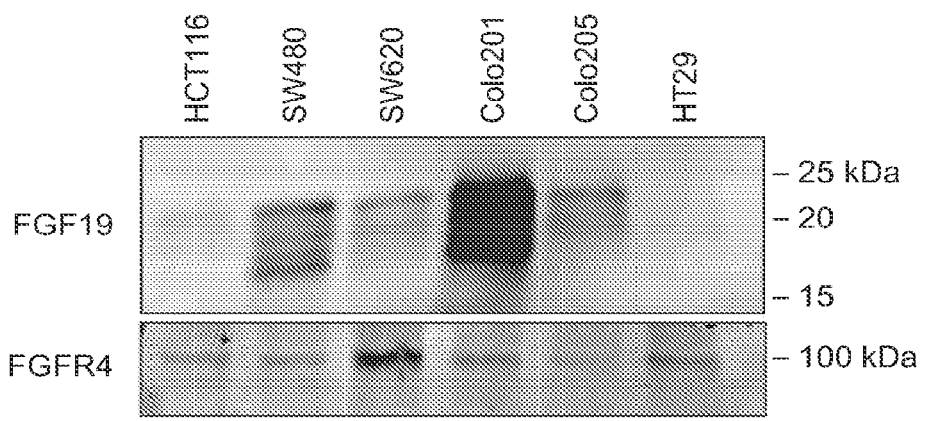

FGF19 and FGFR4 mRNA and protein expression was analyzed in a panel of colon, breast, and liver tumor cell lines. We found FGF19 mRNA expression in a subset of colon cancer cell lines, including Colo201, Colo205, SW620, SW480, and HCT116 (FIG. 3A). SNU185, SNU398, MCF7 and all colon cancer cell lines tested expressed FGFR4 mRNA. FGF19 and FGFR$ protein expression was determined in a panel of cancer cell lines using western blot analysis. With the exception of HT29, which did not express FGF19 protein, the FGF19 and FGFR4 protein levels agreed with their mRNA expression in these cell lines (FIG. 3B). The electrophoretic mobility of the FGF19 secreted by the cell lines was consistent with the expected molecular mass of 24 kDa. However, additional lower molecular mass bands were also detected, possible representing truncated protein.

Figure 3C:
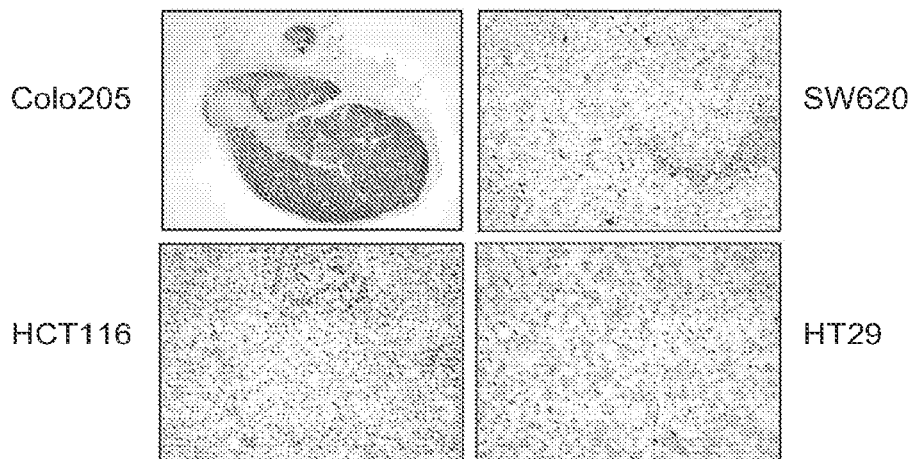
Figure 3D:
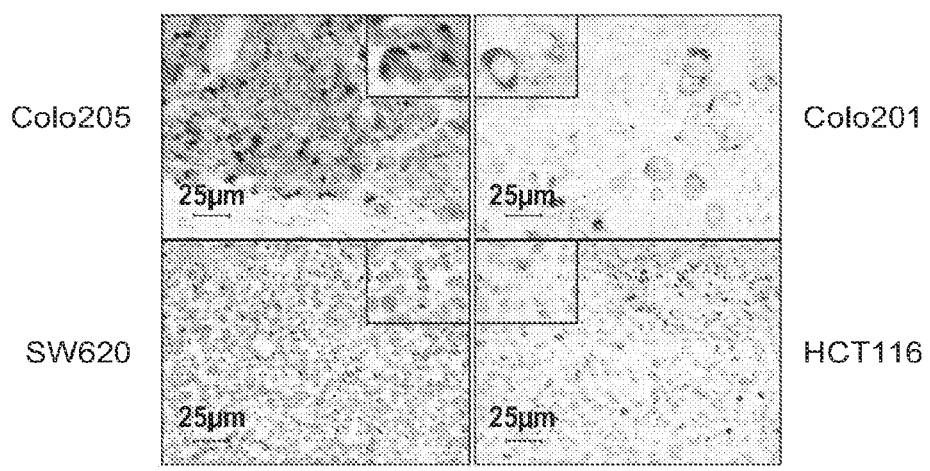

To verify that FGF19 protein expression is maintained in vivo, colon cancer cell line-derived tumor xenografts were evaluated by immunohistochemistry (FIGS. 3C and 3D). Colo205 xenograft tumor tissue had strong FGF19 expression in all neoplastic epithelial cells throughout the tumor, but not in the associated mouse stroma or adjacent normal tissue. SW620 and HCT116 xenografts showed positive immunoreactivity in scattered neoplastic cells. Immunohistochemistry of the FGF19 negative HT29 cell line xenograft did not show any staining. These results suggested that colon cancer cell lines express FGF19 upon growing in vitro in culture dishes as well as in vivo in a subcutaneous xenograft setting.

Example 3

FGF19 is not a Heparin-binding Factor

Figure 4A:
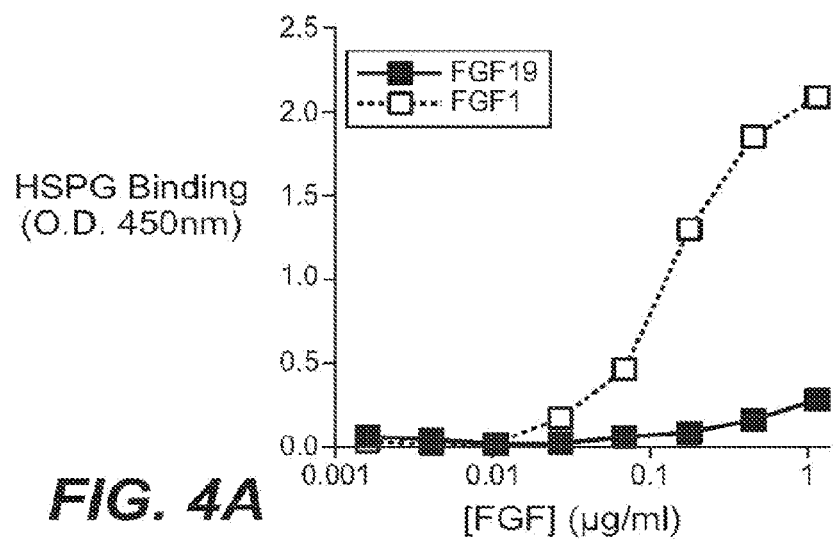
FIG. 4: FGF19 bound to components of the FGFR4 complex. (A) FGF19 and FGFR4 protein were incubated with microwell adsorbed heparin sulfate proteoglycan. The binding was detected with biotinylated specific antibodies followed by horseradish peroxydase conjugated streptavidine and colorimetric substrate. (B) FGF19 and FGF 1 protein were incubated with heparin-agarose and the gel slurry was washed with 1 ml binding buffer containing various NaCl concentrations. The remaining heparin-agarose bound proteins were eluted with SDS PAGE sample buffer and analyzed by Western blot. The control lane (Cont.) represented the original amount of protein directly loaded on the gel. FGF19 protein had a unique binding specificity for FGFR4 captured to a solid phase (C) or in solution (D). (E) FGF19 protein binding to solid phase captured FGFR4-Fc protein in the presence of by various glycosaminoglycans (Hep Sulf: heparin sulfate; CS B: condtroitin sulfate B; CS A: chondroitin sulfate A; CS b: chondroitin sulfate C). (F) FGF19 protein binding to solid phase captured FGFR4 IgG protein in the presence of heparin fragments of various lengths. (G) Scatchard analysis of $^{125}$I-FGF19 protein binding to solid phase captured FGFR4-Fc protein.
Figure 4B:
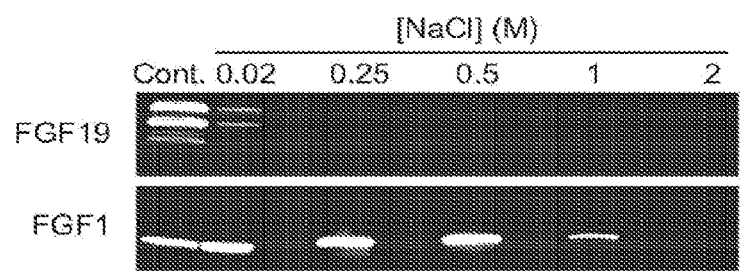

Glycosaminoglycan binding assays were performed to directly assess whether FGF19 protein and heparin interact. In a solid phase binding assay, FGF1 demonstrated a dose dependent binding to the surface-adsorbed purified heparan sulfate proteoglycan (FIG. 4A). By contrast, FGF19 did not bind the coated material. In a pull-down assay, FGF1 strongly bound to heparin-agarose affinity matrix. As previously reported FGF1 was desorbed only with buffers containing NaCl concentrations higher than 1M. By contrast, FGF19 did not significantly bind to heparin agarose at the lowest concentration of NaCl tested (20 mM), and no protein could be detected after washes with higher NaCl concentrations (FIG. 4B). Together, these results indicate that FGF19 did not bind significantly to glycosaminoglycan and therefore can not be considered a heparin binding factor.

Example 4

FGF19 Specifically Binds to FGFR4

Figure 4C:
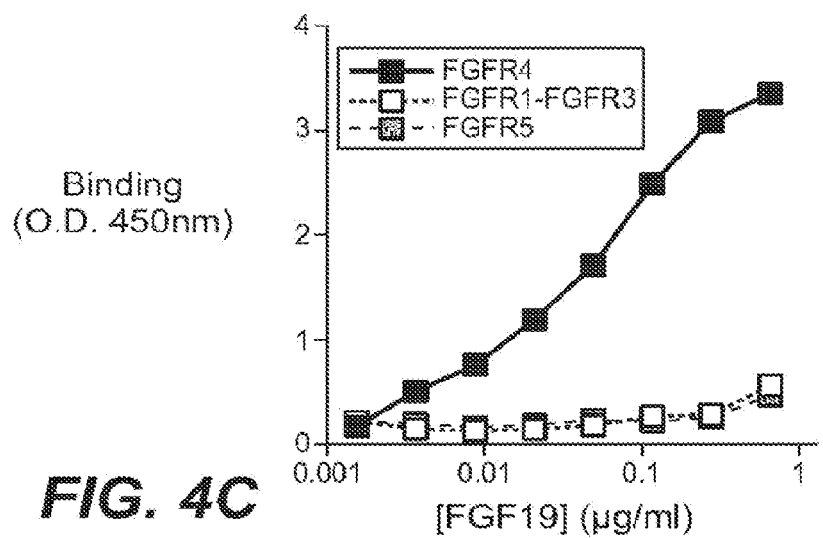
Figure 4D:
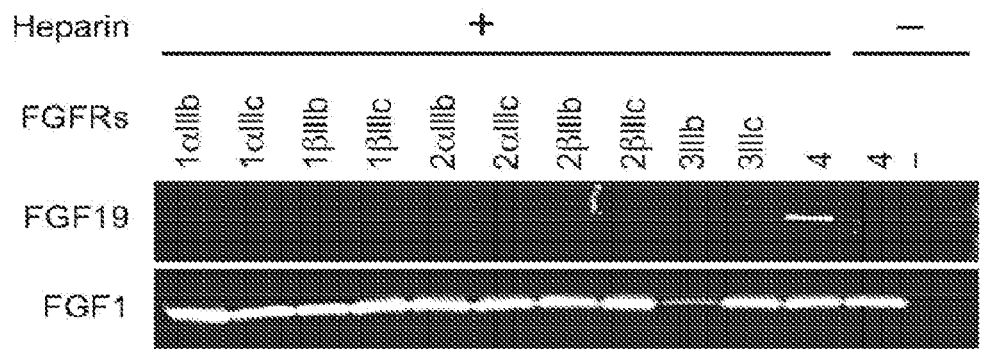

Previous co-immunoprecipitation studies suggest that the receptor binding specificity of FGF19 is restricted to FGFR4 (Xie et al., 1999). To examine FGF19's binding specificity more completely we assessed its interaction with all known human FGFRs in their different alternatively spliced forms including the recently identified FGFR5 (FGFR1L) (Sleeman et al., 2001). In a solid phase assay FGF19 dose dependent binding was restricted to FGFR4 (FIG. 4C). In a receptor pull down assay FGF1 bound to all FGFRs whereas FGF19 interaction was limited to FGFR4 (FIG. 4D). These results are consistent with previous findings (Ornitz et al., 1996; Xie et al., 1999) and further emphasize the unique binding specificity of FGF19 for FGFR4.

Example 5

FGF19 Binding to FGFR4 is Modulated by Glycosaminoglycan

Figure 4E:
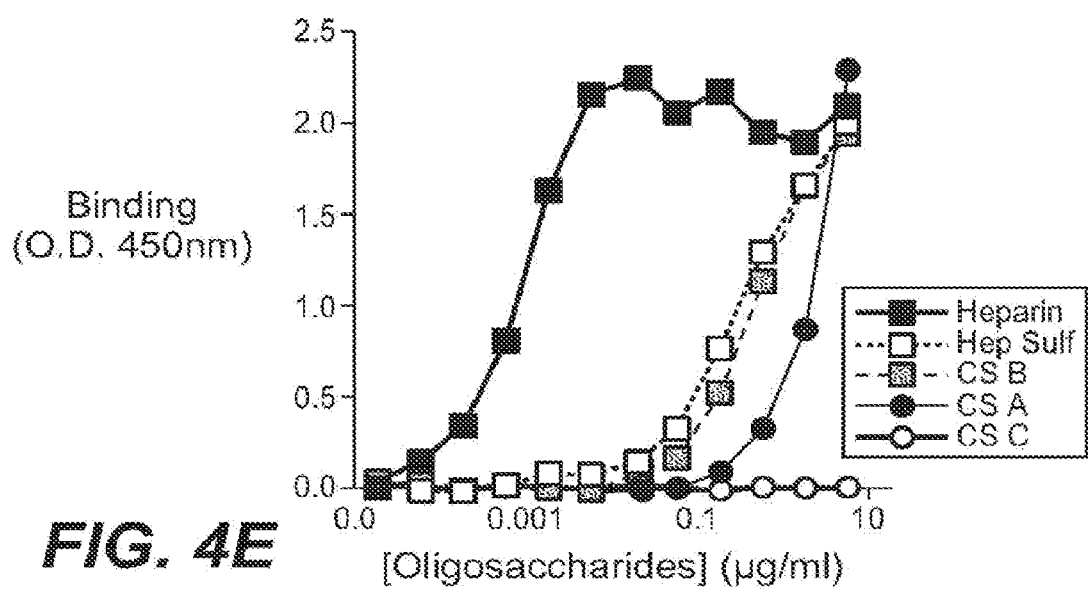

The specificity of the glycosaminoglycan requirement for FGF19 binding to FGFR4 was analyzed using a solid phase receptor binding assay. As seen in FIG. 4E, heparin constituted the most potent promoter of FGF19 interaction with FGFR4 ($EC_{50}$=0.0025 μg/ml), followed by heparan sulfate ($EC_{50}$=0.9 μg/ml), chondroitin sulfate B ($EC_{50}$=1 μg/ml) and chondroitin sulfate A ($EC_{50}$=4 μg/ml). Chondroitin sulfate C did not promote FGF19 binding to FGFR4.

Figure 4F:
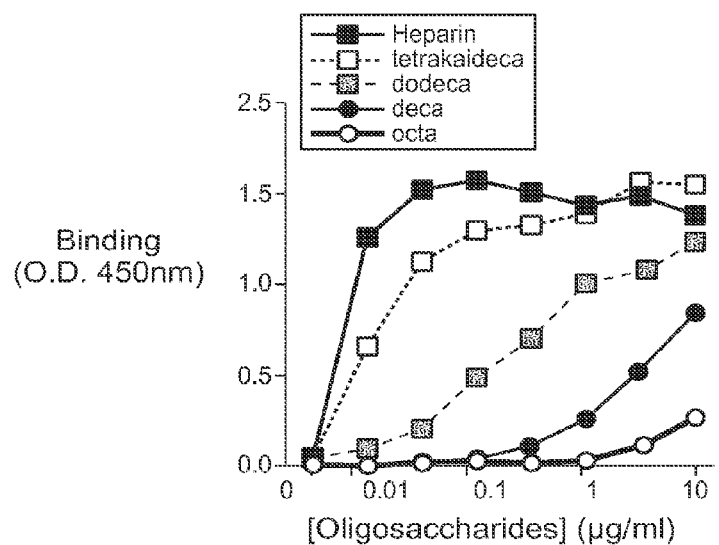

The effect of various lengths of heparin polysaccharide on FGFR4 binding promotion was also analyzed. The heparin octasaccharide showed only a minimal effect on FGFR4 binding at the highest concentration (10 μg/ml) (FIG. 4F). The dose dependent promotion of FGF19 binding to FGFR4 was seen with heparin decasaccharide and longer fragments and this effect was proportional to the heparin molecular weight. Taken together, these results showed that heparin constituted the most potent glycosaminoglycan supporting FGF19 binding to FGFR4, and that heparin's activity was proportional to its molecular weight.

Example 6

FGF19 Binds to FGFR4 with High Affinity

Figure 4G:
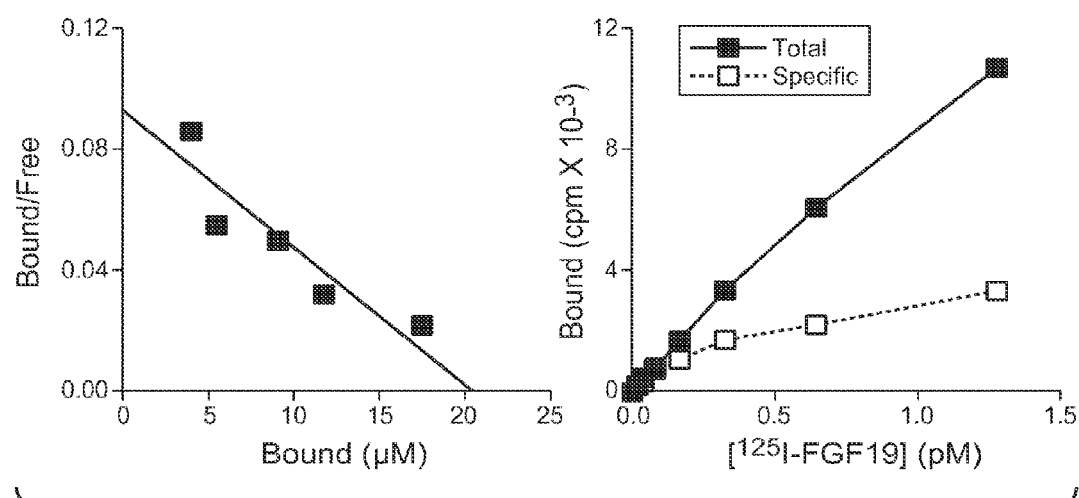

FGF19 binding affinity to FGFR4 was assessed by incubating increasing concentration of [$^{125}$I]FGF19 with immobilized FGFR4 and heparin in the presence or the absence of an excess of unlabeled ligand. FGF19 demonstrated a dose-dependent and saturable binding to FGFR4 (FIG. 4G, inset). A $K_D$ of 0.25 nM for the FGF19 binding to FGFR4 was determined using Scatchard analysis, confirming that the ligand and receptor interact with high affinity.

Example 7

Generation of Anti-FGF19 Monoclonal Antibody

Figures 1, 8A:
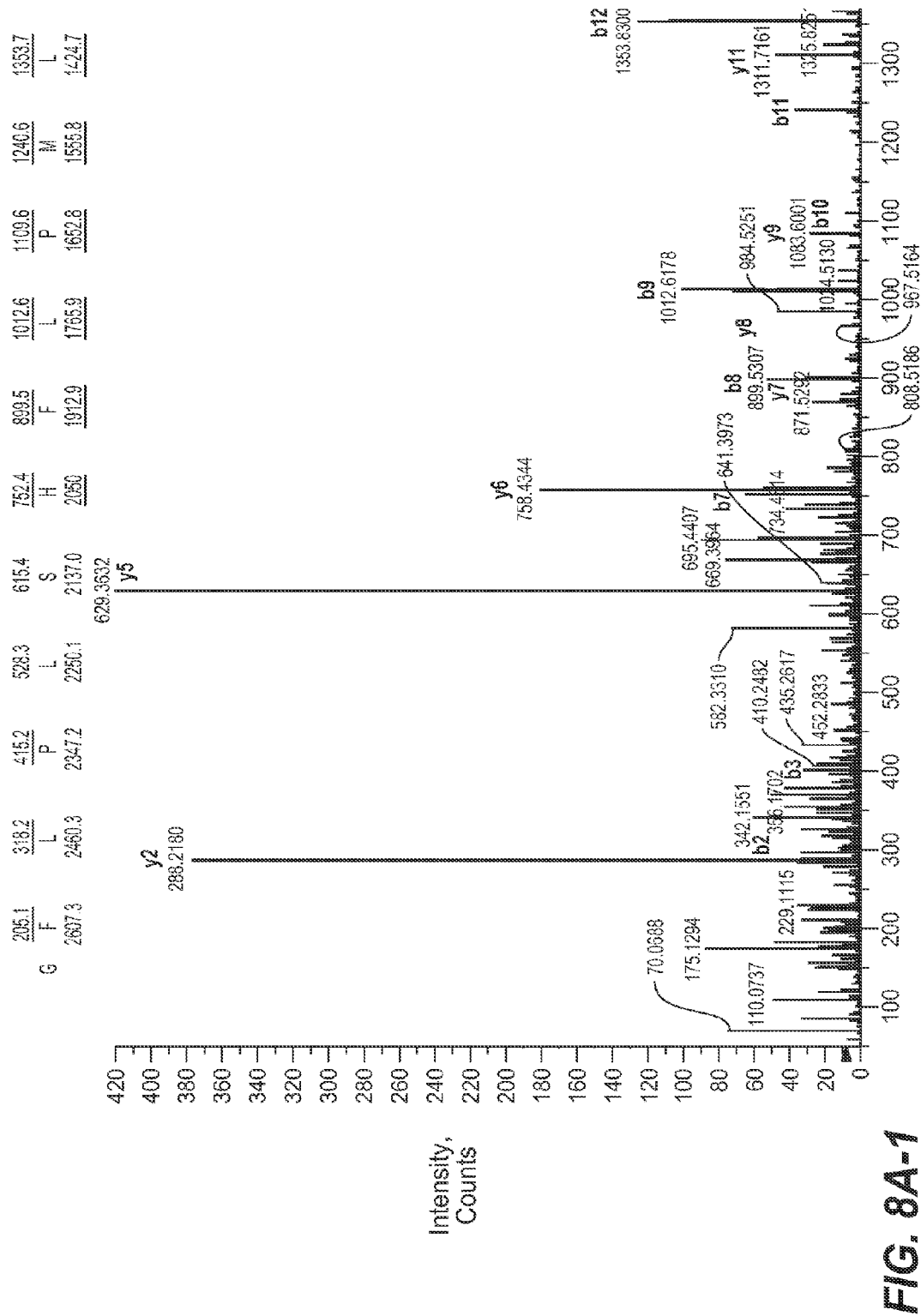
FIG. 8: Antibody epitope sequencing. Collision induced dissociation and manual sequencing of peptides isolated using an epitope excision procedure. (A) Sequence of a peptide comprising an epitope of anti-FGF19 mab 1A6 (SEQ ID NO:9). (B) Sequence of a peptide comprising an epitope of anti-FGF19 mab 1A1 (SEQ ID NO:10).

A panel of anti-FGF19 mouse monoclonal antibodies was generated as described above. The polynucleotide sequence of the inserts was determined using routine sequencing methods. The anti-FGF19 mab 1A6 VL and VH amino acid sequences are shown in FIG. 1.

Example 8

Analysis of Anti-FGF19 Monoclonal Antibody Binding Affinity Using Surface Plasmon Resonance and Enzyme-linked Immunosorbent Assays To determine the binding affinity of mouse anti-FGF19 Mabs, surface plasmon resonance (SRP) measurement was performed with a BIAcore™-3000 was used (BIAcore, Inc., Piscataway, N.J.) as described above. The results of this analysis are shown in Table 5.

TABLE 5

| Antibody | Kd | Kon | Koff |
|---|---|---|---|
| 1A6 (anti-FGF19) | <9 pM | $5.6 \times 10^5$ ($M^{-1}s^{-1}$) | $<5 \times 10^{-6}$ ($s^{-1}$) |
| 1D1 (anti-FGF19) | 32 nM | $2.4 \times 10^4$ ($M^{-1}s^{-1}$) | $7.7 \times 10^{-4}$ ($s^{-1}$) |
| 1A1 (anti-FGF19) | ~300 nM | $1 \times 10^6$ ($M^{-1}s^{-1}$) | $3 \times 10^{-2}$ ($s^{-1}$) |

Figure 5A:
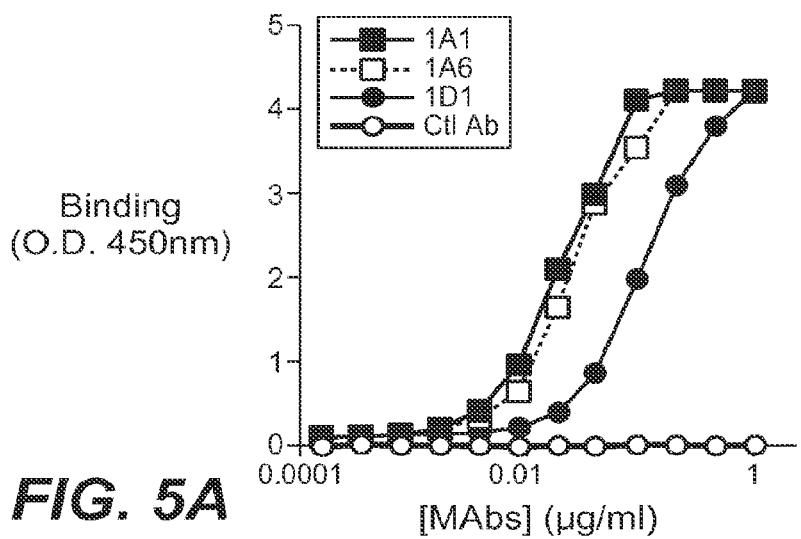
FIG. 5: Anti-FGF19 monoclonal antibody 1A6 inhibited FGF19 biological activities in vitro. (A) Binding of monoclonal antibodies to solid phase captured FGF19 protein. (B) Binding of FGF19 protein to solid phase captured FGFR4-Fc protein in the presence of anti-FGF19 monoclonal antibodies ("mabs"). (C) Treatment with anti-FGF19 mab 1A6 inhibited FGF19 activation of a FGF signaling pathway. (D) Treatment with anti-FGF19 mab 1A6 inhibited FGF19-induced CYP7α1 repression. HEPG2 cells incubated overnight in serum free medium were treated with FGF19 protein in the presence or absence of antibodies. CYP7α1 expression was evaluated by semi-quantitative RT-PCR using gene specific primers and probes and normalized to GAPDH expression. (E) Treatment with anti-FGF19 mab 1A6 inhibited FGF19-promoted HCT116 cell migration. The surface of 8 µm porosity 24-well modified Boyden chambers was coated with type 1 collagen. Cells in serum free medium were added to the upper chamber. Cells that migrated to the lower chamber following addition of the same media containing FGF19 and various concentrations of anti-FGF19 mab 1A6 were stained and counted. Triplicate sets of data were averaged for each condition.
Figure 5B:
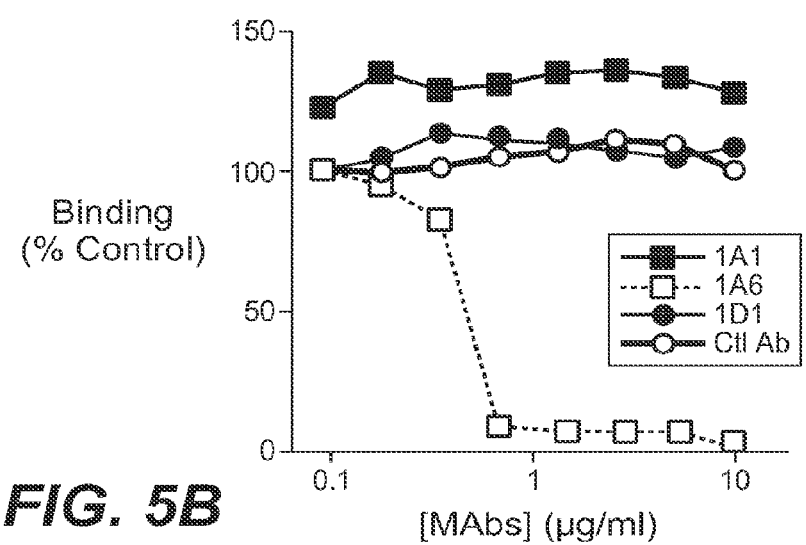

In enzyme-linked immunosorbent assays, anti-FGF19 mabs 1A1 and 1A6 bound to FGF19 with a comparable EC50 of 40 pM whereas anti-FGF19 mab 1D1 bound with an EC50 of 400 pM (FIG. 5A). In a solid phase receptor binding assay, 1A6 blocked FGF19 binding to FGFR4 with an IC50 of 3 nM (FIG. 5B). 1A1, 1D1 and an irrelevant control antibody did not inhibit this interaction.

Example 9

Anti-FGF19 Antibody Blocked FGF19 Signaling in a Cell-based Assay

Several cell-based assays were performed in order to determine whether the anti-FGF19 antibodies blocked the interaction of FGF19 and FGFR4.

Figure 5C:
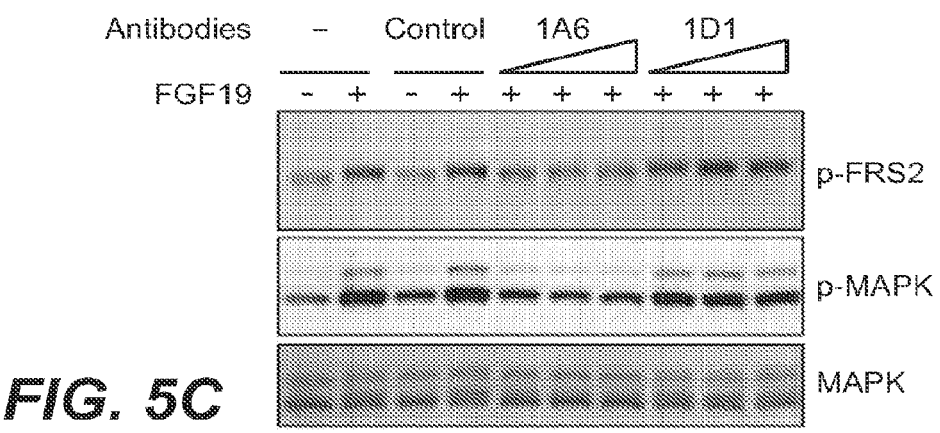
Figure 5D:
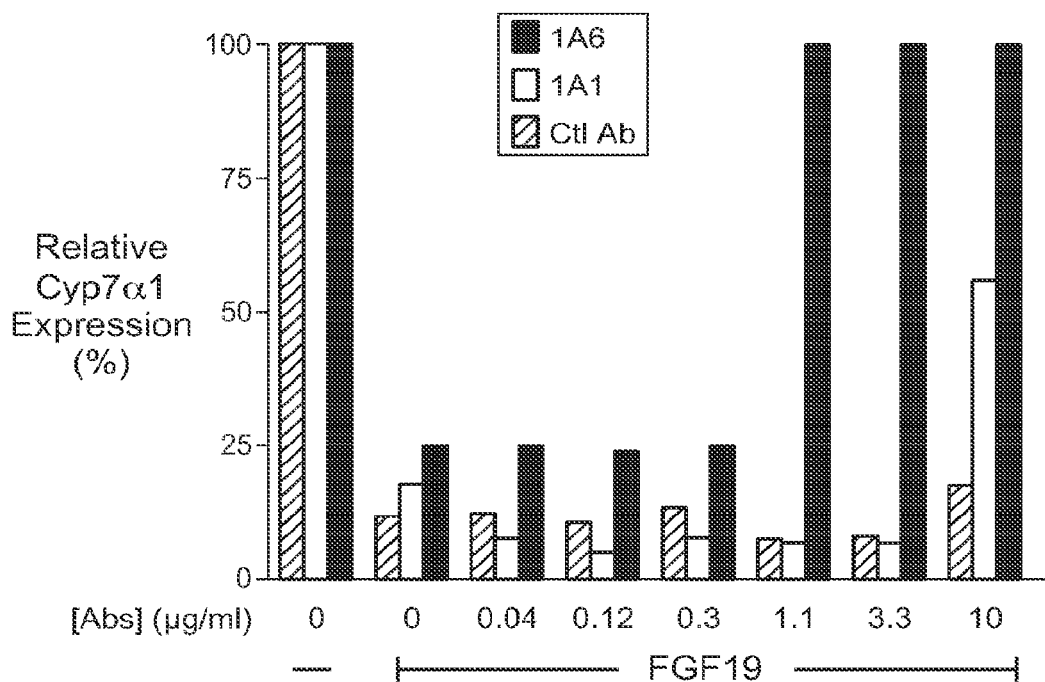

FGF19 plays a role in cholesterol homeostasis by repressing hepatic expression of cholesterol-7-α-hydroxylase 1 (Cyp7α1), the rate-limiting enzyme for cholesterol and bile acid synthesis (Gutierrez et al (2006) Arterioscler Thromb Vasc Biol 26, 301-306; Yu et al (2000) J Biol Chem 275, 15482-15489). The ability of anti-FGF19 antibodies 1A1 and 1A6, or isotype-matched negative control antibody (at concentrations ranging from 10 ug/ml to 0.04 ug/ml) to block FGF19-induced downregulation of cyp7α1 was assessed using hepatocellular carcinoma HEP3B cells (Schlessinger, Science 306:1506-1507 (2004)) as described above. In the absence of anti-FGF19 antibody, FGF19 treatment reduced cyp7α1 expression by 75% (FIG. 5D). Treatment with 1.1 µg/ml mouse anti-FGF19 Mab 1A6 abolished FGF19-induced repression of cyp7α1 expression. By contrast, treatment with mouse anti-FGF19 Mab clone 1A1 only reduced the repression by 50% at the highest concentration tested (10 µg/ml), but not at lower antibody concentrations. The presence of a control antibody did not affect FGF19 activity. The IC50 for anti-FGF19 antibody 1A6 inhibition of FGF19-induced downregulation of cyp7α1 gene expression was about 0.4 ug/ml. The IC50 for anti-FGF19 antibody 1A1 inhibition of FGF19-induced downregulation of cyp7α1 gene expression was about 10 ug/ml.

Anti-FGF19 mab 1A6 was also tested for its ability to block the FGF19-induced FGF pathway activation in hepatocellular carcinoma Hep3B cells (Eswarakumar et al (2005) Cytokine Growth Factor Rev 16:139-149; Schlessinger, J (2004) Science 306:1506-1507). Serum starved hepatocellular carcinoma Hep3B cells were treated with FGF19 in the absence or the presence of a negative control antibody or with various concentrations of anti-FGF19 monoclonal antibodies 1A6 or 1D1 (at 30, 10 and 3.3 ng/ml), and FRS2 and MAPK phosphorylation determined as described above. Treatment with anti-FGF19 Mab 1A6 significantly blocked FGF19-induced FRS2 and MAPK phosphorylation at all doses tested (FIG. 5C). By contrast, treatment with the control antibody and anti-FGF19 mab 1D1 did not show significant inhibitory activity.

Figure 5E:
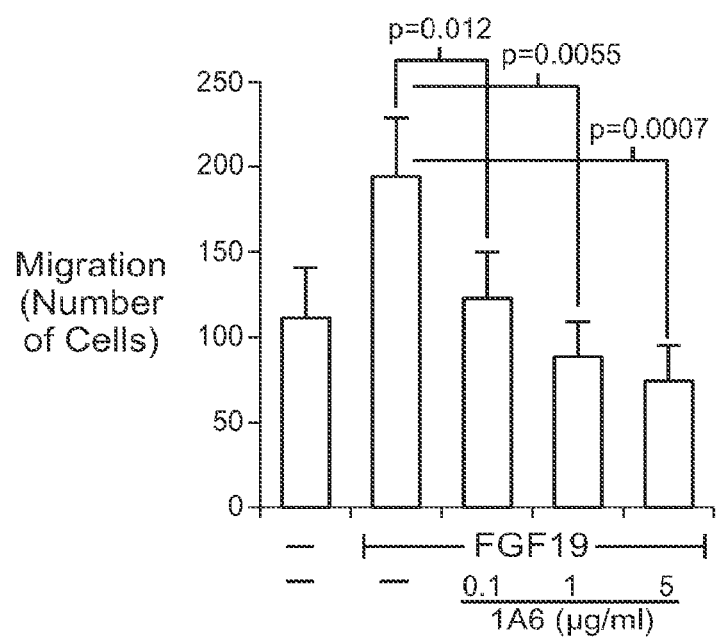
Figure 10:
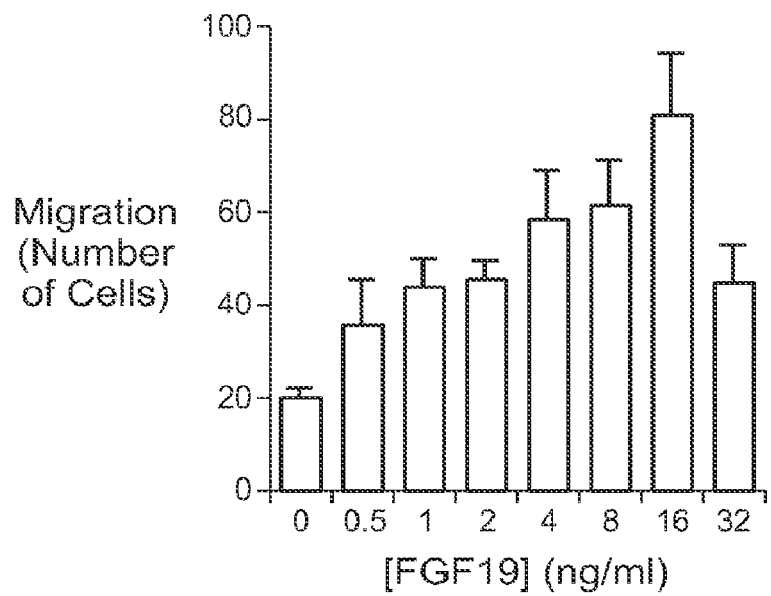
FIG. 10: Treatment with FGF19 protein promoted HCT116 cell migration. The surface of 8 μm porosity 24-well modified Boyden chambers was coated type 1 collagen. HCT116 cells in serum free medium were added to the upper chamber. The lower chamber was filled with the same media containing various concentrations of FGF19 and the plates were incubated at 37° C. The next day the cells that migrated to the lower side of the insert were stained and counted under a microscope. Triplicate sets of data were averaged for each condition.

Because FGFR4 plays a role in cell migration, we evaluated the chemotactic activity of FGF19 (Wang et al (2005) Clin Cancer Res 10:6169-6178). In a modified Boyden chamber assay, FGF19 promoted HCT116 cell migration in a dose dependent fashion, reaching a maximum at 16 ng/ml (FIG. 10). The anti-FGF19 mabs were tested for the ability to inhibit FGF19-promoted cell migration. At 0.1 µg/ml, treatment with anti-FGF19 mab 1A6 inhibited FGF19-induced cell migration (FIG. 5E). Treatment with higher concentrations of 1A6 reduced cell migration to below the basal HCT116 cell migration level, likely by inhibiting both exogenously added and endogenously produced FGF19.

These results demonstrated that anti-FGF19 antibody 1A6 was a potent inhibitor of FGF19 activity in vitro.

Example 10

Antibody 1A6 Binding Determinant is Localized in the FGF19 Binding Interface with FGFR4

Figure 6A:
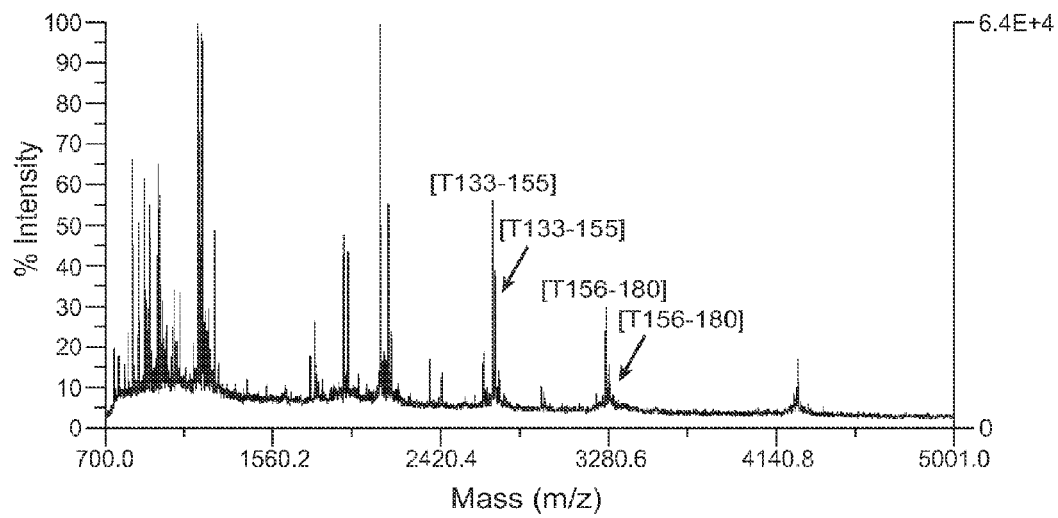
FIG. 6: Identification of epitopes recognized by anti-FGF19 antibodies. FGF19 protein was incubated for 2 h with agarose coupled antibody. The resin was washed and digested with trypsin overnight at 37 C. The gel slurry was washed and the bound peptides were eluted and analyzed by MALDI-TOF-MS. (A) Mass spectroscopic analysis of soluble fraction of trypsin digested FGF19 bound to agarose coupled mab 1A6. (B) Mass spectroscopic analysis of FGF19 tryptic peptide eluted from agarose coupled 1A6 antibody. (C) Mass spectroscopic analysis of FGF19 tryptic peptide eluted from agarose coupled 1A 1 antibody. (D) Peptide competition of anti-FGF19 mab 1D1 binding to solid phase-captured FGF19. Anti-FGF19 mab 1D1 was incubated with FGF19-His captured to nickel coated plates in the presence of peptides representing various portions of FGF19 protein. The antibody binding was detected with a HRP-conjugated anti-mouse IgG and chromogenic substrate. (E) Mapping of 1A6 epitope (indicated with an arrow) onto the FGF19-FGFR4 interaction model. FGFR4 surface is represented as a globular form whereas FGF19 is represented as a ribbon.
Figure 6B:
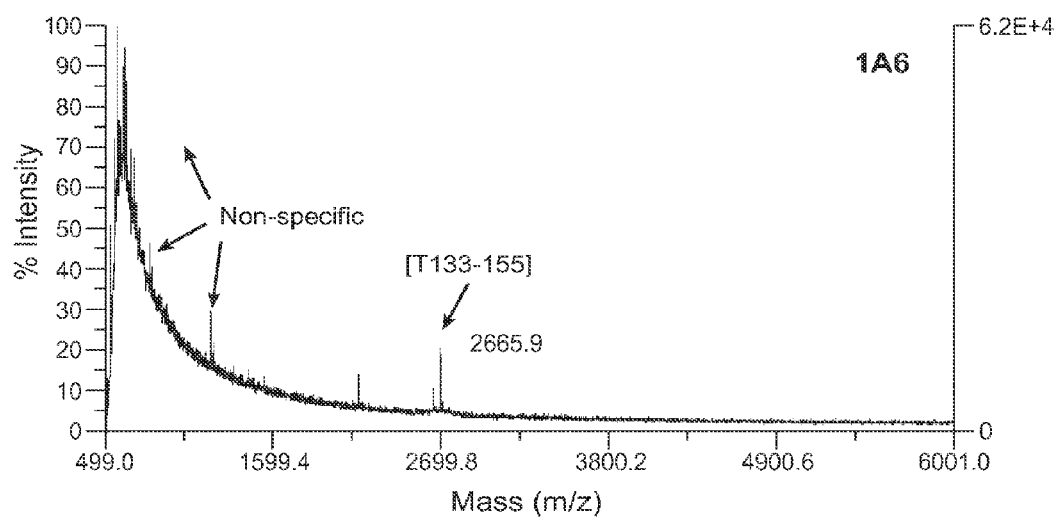
Figure 6C:
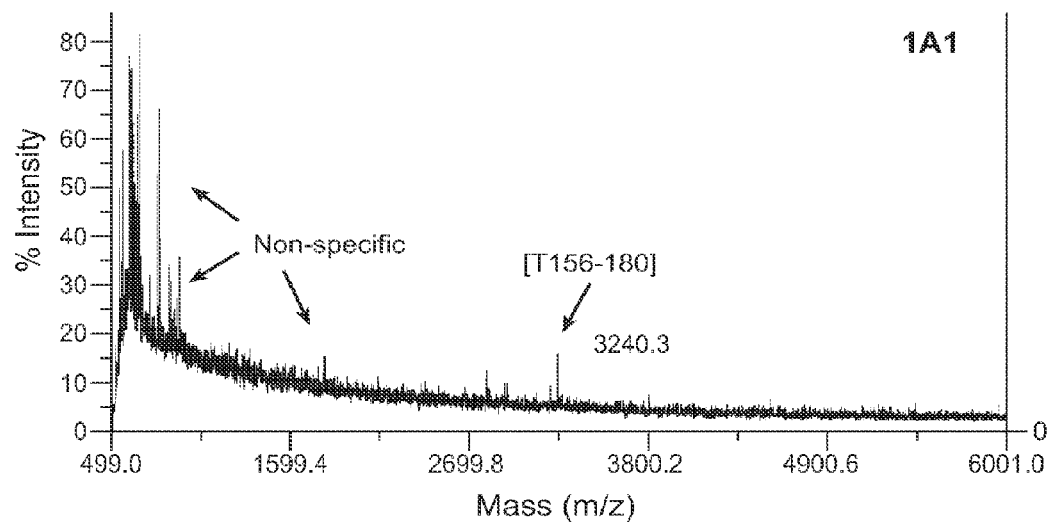

A mass spectrometric approach was used to localize the epitopes of anti-FGF19 Mab 1A6 and 1A1 and to evaluate whether FGF19 conformational components contributed to their binding. We first attempted to isolate an epitope containing peptide from an FGF19 tryptic digest using an agarose-coupled 1A6 affinity matrix. This approach was unsuccessful possibly because the FGF19 fragmentation compromised the conformational integrity of 1A6 epitope. To test this hypothesis, we modified the procedure and FGF19 was incubated with the agarose-coupled antibodies and the adsorbed protein was then digested with trypsin. The analysis of the total digest demonstrated a complete fragmentation of the adsorbed FGF19, without 1A6 masking of any trypsin cleavage sites (FIG. 6A). The matrix was washed extensively and the bound peptides were eluted and identified by mass spectrometry. The non-specifically adsorbed peptides were identified using an irrelevant control antibody coupled to agarose in a parallel experiment.

Figures 1, 8B:
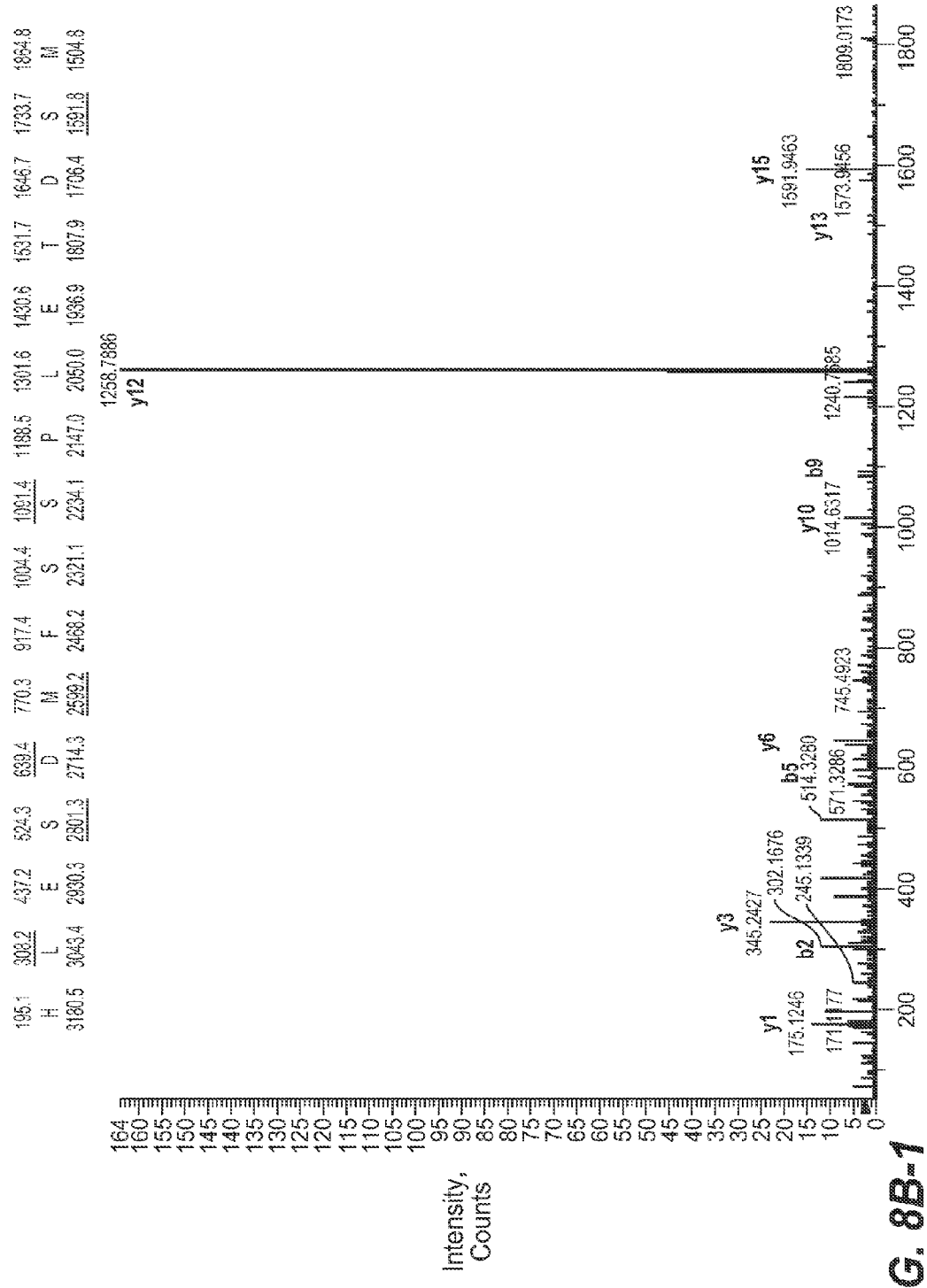

The results of this analysis are shown in FIG. 6. The agarose coupled anti-FGF19 mab 1A6 specifically recognized the FGF19 peptide G133-R155 (FIGS. 6B and 8A). Agarose-coupled anti-FGF19 mab 1A1 specifically recognized the peptide G156-R180 (FIGS. 6C and 8B).

Figure 6D:
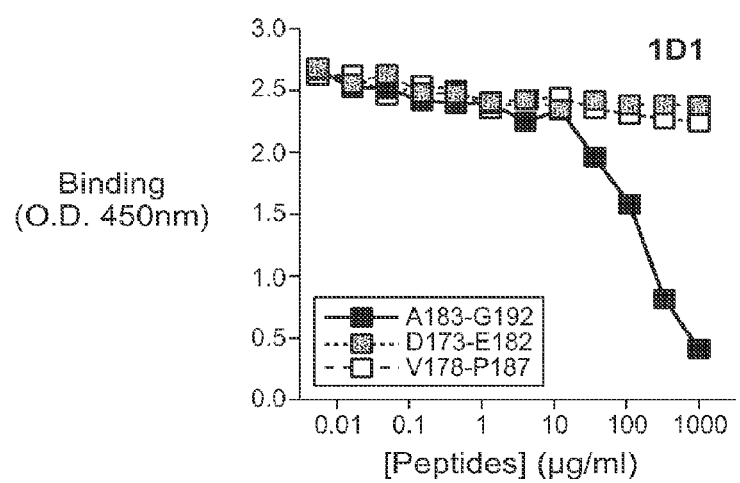

Because conjugation of anti-FGF19 mab 1D1 to agarose abolished its binding to FGF19, a peptide competition binding assay was used to identify its epitope. Only FGF19 amino acids A183-G192 competed with mab 1D1 binding (FIG. 6D). This peptide did not compete the binding of mab 1A1 to FGF19. Because overlapping peptides were used in this competition assay, we surmise that the mab 1D1 epitope is located in the last 4 distal FGF19 amino acids (SFEK).

Figure 6E:
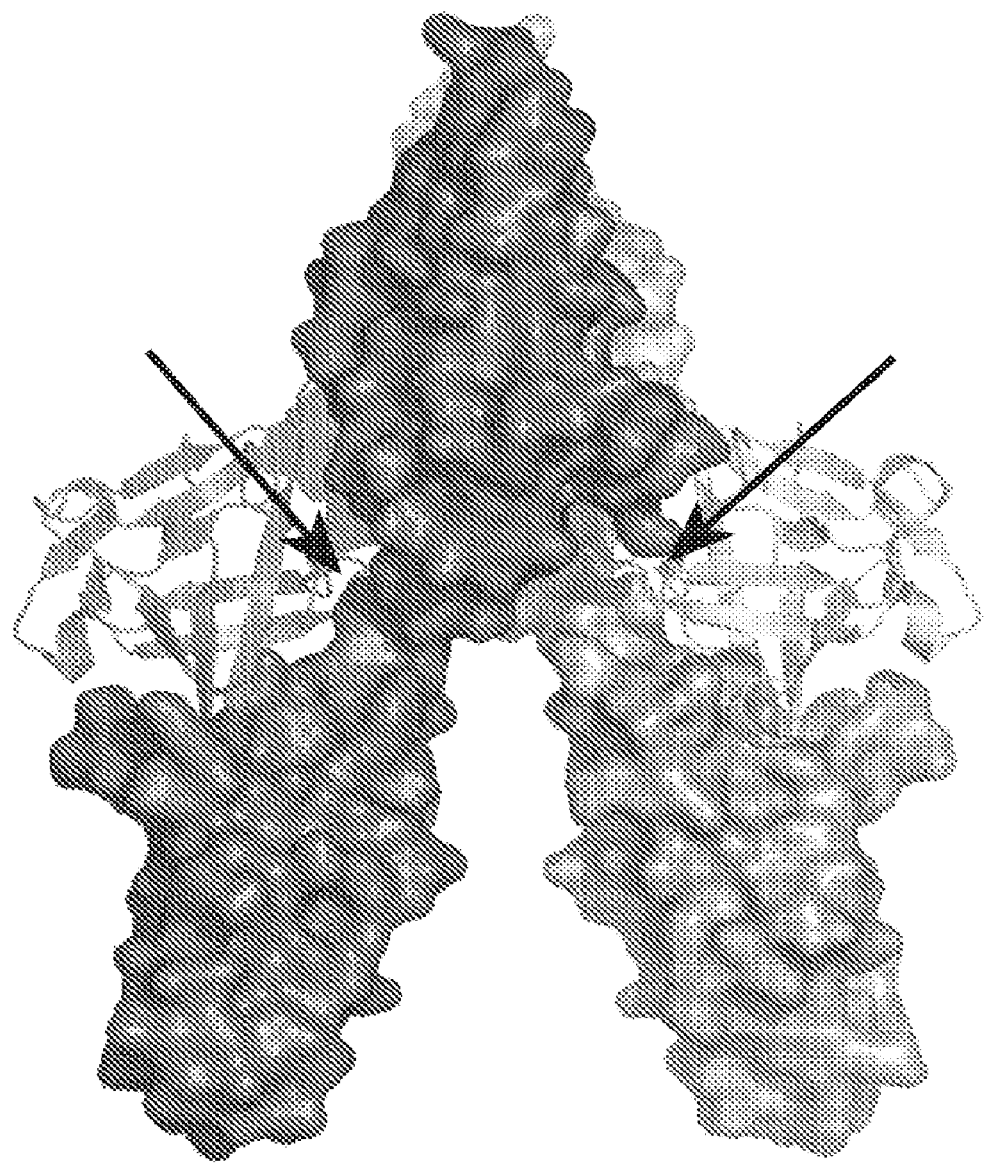

The epitopes of mabs 1A1, 1D1 and 1A6 were mapped onto the previously described structural model of FGF19 interaction with FGFR4 (Harmer et al (2004) Biochemistry 43, 629-640). The epitopes of 1A1 and 1D1 are located in a distal portion of FGF19 that is not represented on this model due to its lack of ordered structure. However, the 1A6 epitope is localized in the FGF19 binding interface with FGFR4 (FIG. 6E). These results suggest that anti-FGF19 Mab 1A6 directly occludes the receptor-binding site of FGF19.

Example 11

Treatment with Anti-FGF19 Monoclonal Antibodies Inhibited Tumor Growth in vivo

To determine whether FGF19 neutralization could inhibit tumor growth in vivo, anti-FGF19 antibodies were tested in two tumor xenograph models as described above. The colon cancer cell lines HCT116 and colo201 were selected because they expressed both FGF19 and FGFR4 (FIG. 3A) and form tumors in vivo. In addition, anti-FGF19 antibody 1A6 showed a blocking activity on the FGF19-induced HCT116 cells migration in vitro.

Figure 7A:
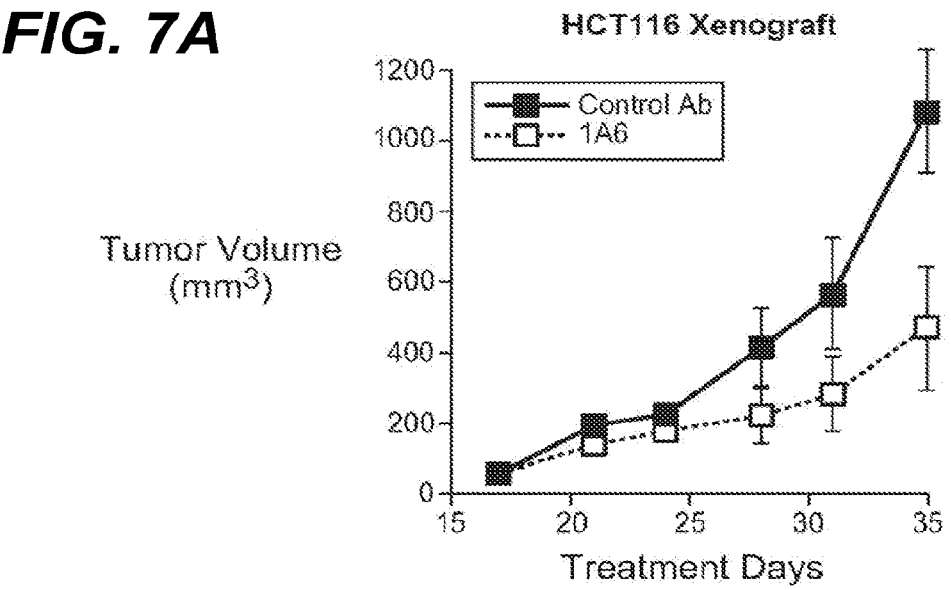
FIG. 7: Treatment with anti-FGF19 mouse monoclonal antibody 1A6 inhibited colon tumor growth in vivo. Athymic mice were subcutaneously inoculated with $5\times10^6$ HCT1126 or Colo201 cells. Mice bearing established tumors of equivalent volume (~100 mm$^3$) were randomized into groups and treated intraperitoneally twice weekly with anti-FGF19 mab 1A6 or a control antibody. Results are given as mean tumor volume+/−sem. At the end of the studies, HCT116 xenograft tumors and Colo201 xenograft tumors from anti-FGF19 mab 1A6-treated or control antibody-treated mice were excised, homogenized and analyzed for FGFR4, FRS2, ERK and β-catenin activation by Western blot. (A) Growth of HCT116 colon tumor xenografts was inhibited by treatment with anti-FGF19 mab 1A6 compared to treatment with control antibody. (B) Phosphorylation of FGFR4, FRS2, and ERK, and β-catenin activation was inhibited in anti-FGF19 mab 1A6-treated HCT116 xenograft tumors. (C) Growth of Colo201 colon tumor xenografts was inhibited by treatment with anti-FGF19 mab 1A6 compared to treatment of control antibody. (D) Phosphorylation of FGFR4, FRS2, and ERK, and β-catenin activation was inhibited in anti-FGF19 mab 1A6-treated Colo201 xenograft tumors. For (A) and (C), arrows indicate administration of treatment. Results are given as mean tumor volume±SE.

Mice with established HCT116 xenograft tumors were treated twice weekly with 5 mg/kg of either anti-FGF19 mab 1A6 or a control antibody. At day 35, treatment with anti-FGF19 mab 1A6 significantly suppressed tumor growth by 57% (p=0.07, n=5) compared to the control antibody treated group (FIG. 7A). This study was repeated using a higher dose of antibody 1A6 (15 mg/kg; 2× week) and a statistically significant suppression of tumor growth was observed (60% growth inhibition, p=0.01, n=5).

Figure 7B:
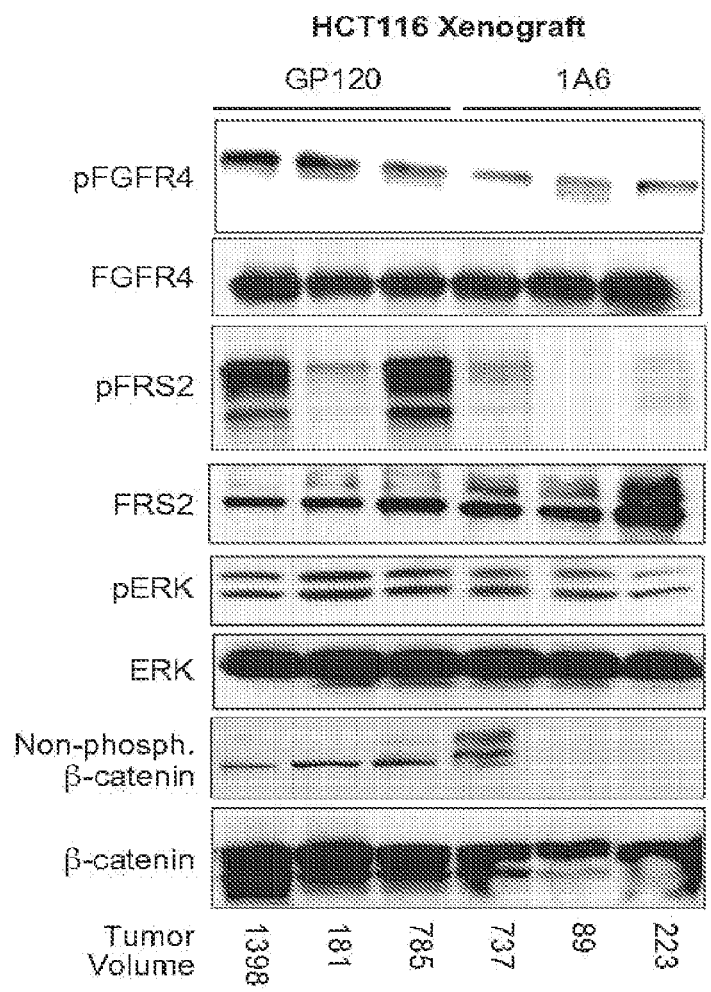

To verify that anti-FGF19 mab 1A6 inhibited tumor growth by blocking FGF19 activity, tumors were examined at the end of the study for markers of FGFR4 signaling. Activation of FGFR4, FRS2, ERK and β-catenin was significantly decreased in tumors from animals treated with anti-FGF19 mab 1A6 compared to animals treated with the control antibody (FIG. 7B).

Figure 7C:
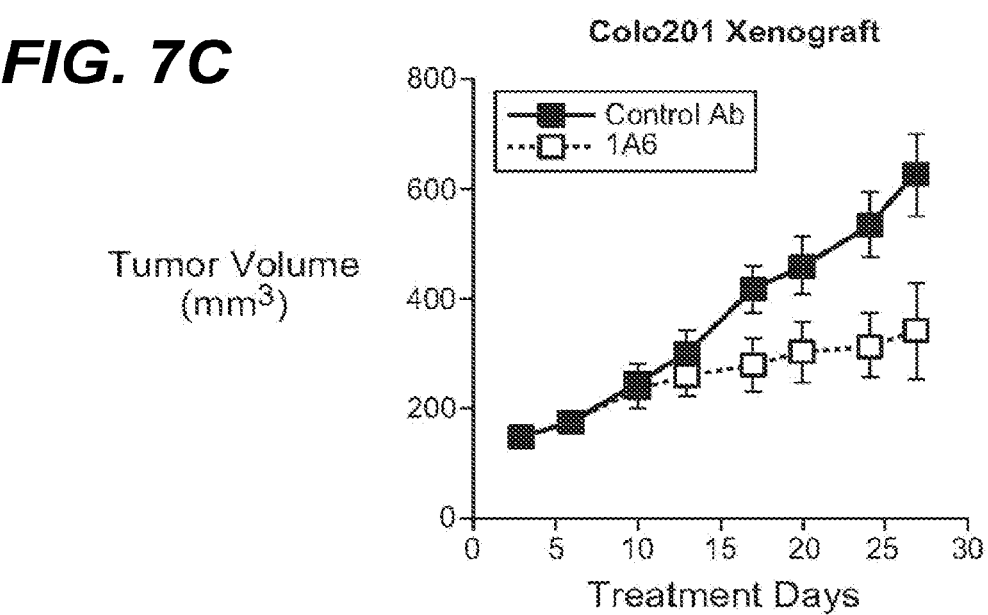
Figure 7D:
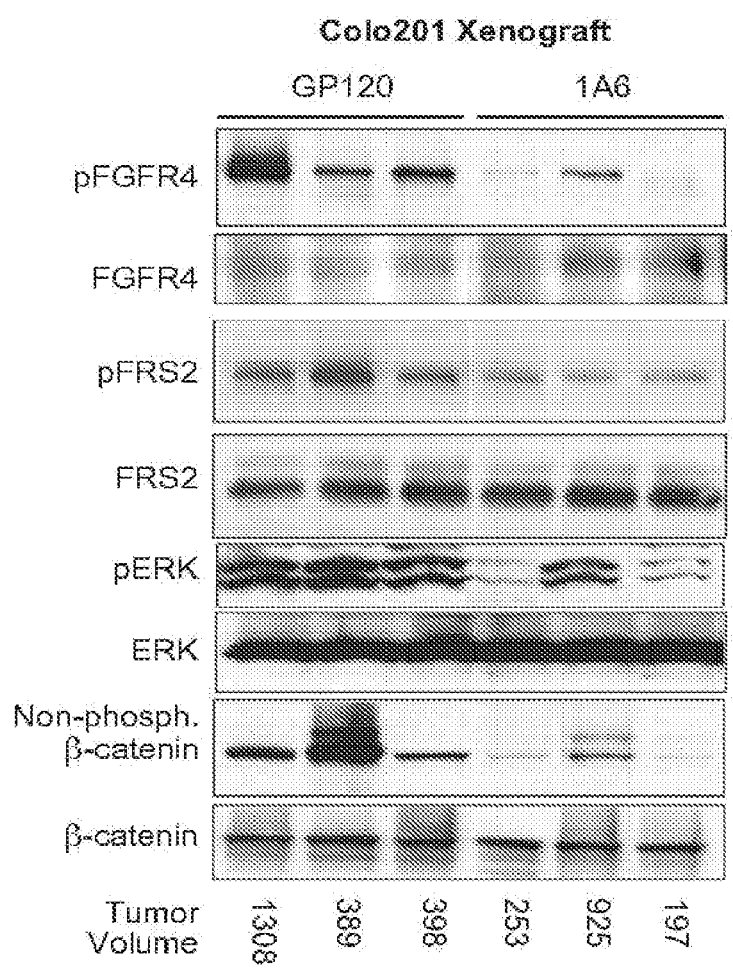

Next, we used xenografts of Colo201, a colon cancer cell line expressing higher FGF19 levels than HCT116 (FIG. 1A). Treatment (30 mg/kg; 2×/week) with anti-FGF19 mab 1A6 significantly suppressed the growth of established colo201 tumors (at day 27, 64% growth inhibition, p=0.03, n=5) compared to the control antibody (FIG. 7C). Analysis of the excised tumors showed that treatment with anti-FGF19 mab 1A6 significantly decreased FGFR4, FRS2, ERK and β-catenin activation in xenograft tumors compared to the control antibody treatment (FIG. 7D). These results demonstrated efficacy of anti-FGF19 mab 1A6 in colon cancer models and demonstrated its activity with inhibition of FGF19 dependent FGFR4, FRS2, ERK and β-catenin activation.

Example 12

Figure 9A:
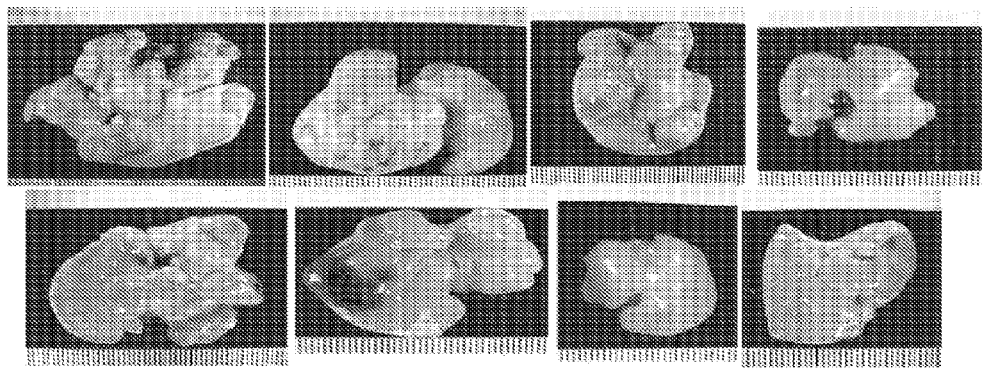
FIG. 9: Treatment with anti-FGF19 mouse monoclonal antibody 1A6 inhibited hepatocellular carcinoma in vivo in a FGF19-transgenic hepatocellular carcinoma animal model. FGF19 transgenic mice were treated with either a control antibody or anti-FGF19 mab 1A6, and liver was collected for gross evaluation (A). MicroCT analysis using an iodinated triglyceride for enhancement of normal hepatocytes demonstrated increased unenhanced tumor volume in control treated versus anti-FGF19 mab 1A6-treated liver (B).
Figure 9A:
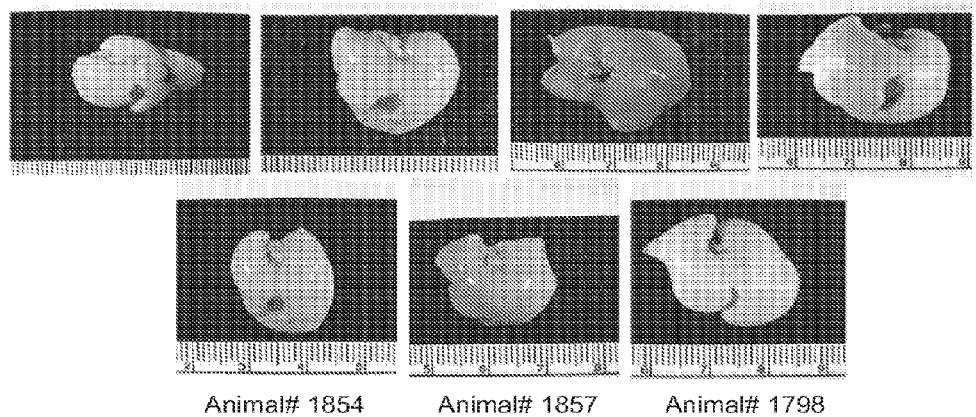
Figure 9B:
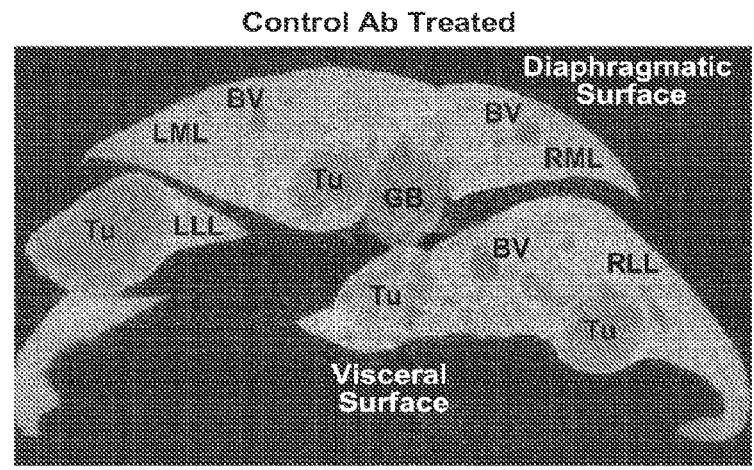
Figure 9B:
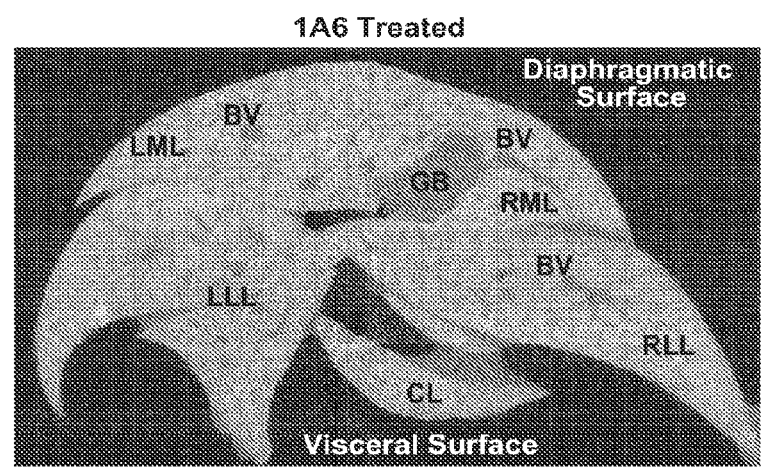
Figure 9B:
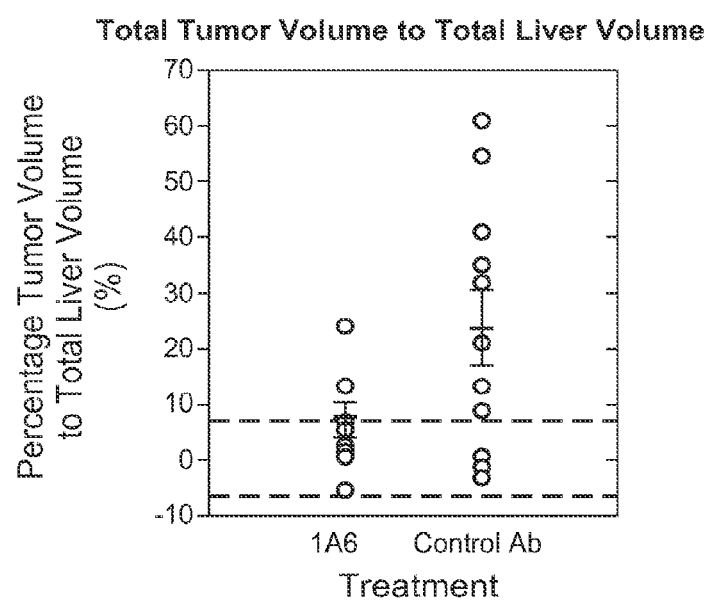

Treatment with Anti-FGF19 Monoclonal Antibodies Prevented Hepatocellular Carcinomas and Weight Loss in FGF19 Transgenic Mice Over-expression of FGF19 in the skeletal muscle of transgenic mice resulted in development of hepatocellular carcinomas by 10-12 months of age (Nicholes et al., Am J Pathol. 160:2295-2307, 2002). To confirm that FGF19 is acting as a tumor promoter in this model, we treated the FGF19 transgenic mice with a tumor initiator, diethylnitrosamine (DEN), which accelerated tumor formation by 50%. To determine whether anti-FGF19 mab 1A6 could prevent hepatocellular carcinomas, DEN-accelerated FGF19 transgenic mice were treated with either 1A6 or control antibody (anti-gp120) for 6 months. At the end of the treatment, all of the control-treated mice had grossly evident multifocal, large hepatocellular carcinomas throughout the liver lobes whereas anti-FGF19 mab 1A6-treated animals had either no liver tumors or, in one case (#1862), a single small tumor present on the diaphragmatic surface of the median lobe (FIG. 9A). Liver weights from anti-FGF19 Mab 1A6-treated mice (mean=1.71±0.05 grams) were significantly lower than liver weights from control treated mice (mean=3.15±0.58 grams; p=0.014), but were not significantly different from those of normal FVB wild-type mice (mean=1.56±0.08 grams; p=0.82). In addition, tumor volume was determined by micro-CT image analysis, corrected for tumor volume with normal FVB liver, and graphed as a percent of total liver volume (FIG. 9B). Percent tumor volume of anti-FGF19 Mab 1A6-treated mice (mean=7.5±3.2%) was significantly lower than control gp120-treated mice (mean=23.8±6.8%; p=0.05). Furthermore, tumor weights strongly correlated with percent tumor volume ($r^2$=0.993702). These data clearly demonstrated that anti-FGF19 Mab 1A6 effectively neutralized circulating FGF19 to prevent tumor formation in FGF19 transgenic mice.

Because FGF19 causes weight loss when overexpressed as a transgene in mice (Tomlinson et al. Endocrinology. 2002 May; 143(5): 1741-7), we evaluated body weights of mice in the two treatment groups. Mice were weighed weekly and body weights were compared between treatment groups. At 3 months of age, control treated mice (mean weight 27.98 g±0.8351; N=5) weighed significantly less than anti-FGF19 mab 1A6 treated (mean weight21.32±0.5036; N=6) (p<0.0001). Weights of 1A6-treated FGF19 TG mice were similar to weights of normal FVB wild-type mice that were evaluated in a different experiment (mean weight 33.22±1.838 N=6). These data demonstrated that treatment with anti-FGF19 mab 1A6 effectively abrogated FGF19-induced weight loss in FGF19 transgenic mice.

Example 13

FGF19 Treatment Induced Tyrosine Phosphorylation of β-Catenin and Caused Loss of E-cadherin Binding to Beta-catenin in HCT116 Cells Hepatocellular carcinomas found in FGF19-expressing transgenic mice have neoplastic cell that show immunoreactivity with beta-cadherin (β-catenin or b-cat) antibodies (Nicoles et al., supra). Furthermore, it has been suggested that Wnt signaling can initiate or promote FGF signaling in various cell types and organs during a variety of cellular processes, including human colorectal carcinogenesis, and that co-activation of Wnt and FGF signaling pathways in tumors leads to more malignant phenotypes (see refs 7-12 in Cancer Biol & Therapy 5:9, 1059-64, 2006). Thus, the effect of FGF19 or inhibition of FGF19 signaling on the Wnt signaling pathway was tested using treatment with FGF19, treatment with anti-FGF19 monoclonal antibody 1A6, or FGFR4-directed shRNA knockdown in human colon cancer (HCT116) cells. β-catenin tyrosine phosphorylation, β-catenin-E-cadherin binding and active-β-catenin levels were assessed in treated cells using immunoprecipitation and immunoblot analysis.

Figure 11:
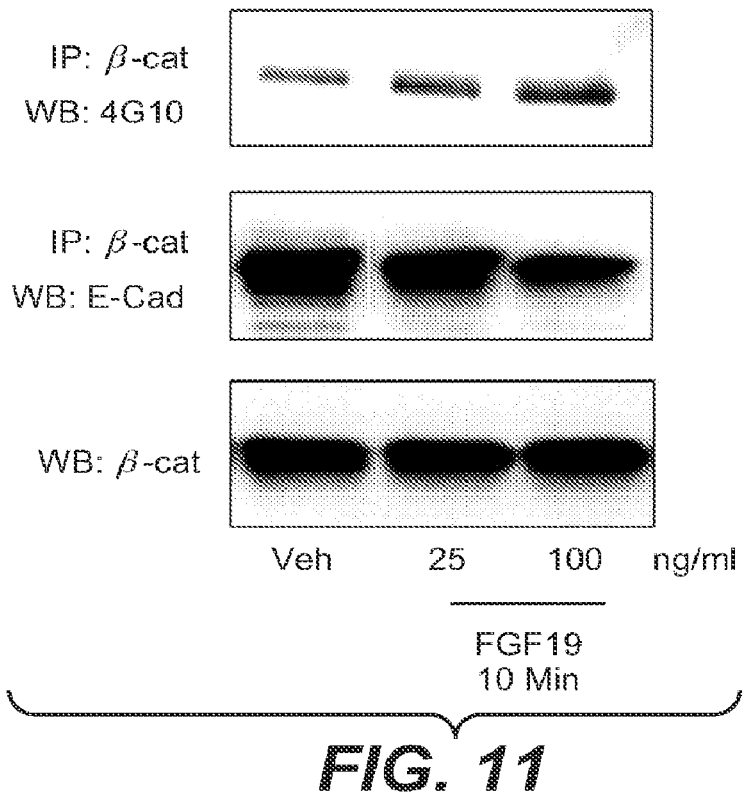
FIG. 11: Treatment with FGF19 induced tyrosine phosphorylation of β-catenin and caused loss of E-cadherin binding to β-catenin in colon cancer cell line HCT116. Serum-starved colon cancer cells were treated with either vehicle ("veh") (control) or FGF19 at 25 and 100 ng/ml for 10 minutes. Tyrosine phosphorylation of β-catenin was determined by immunoprecipitation ("IP") and immunoblotting ("WB"). The same blot was stripped and reprobed using an anti-E-cadherin antibody and subsequently reprobed for total β-catenin using an anti-β-catenin antibody. Representative blots from three separate experiments are shown. Quantitative analysis of β-catenin phosphorylation and β-catenin bound to E-cadherin was determined by calculating the ratio between the phosphorylated E-cadherin and total β-catenin levels from three separate experiments (mean values±SE).

Treatment of colon cancer cells (HCT116) with FGF19 (25-100 ng/ml) resulted in a significant increase in tyrosine phosphorylation of β-catenin as early as 10 min (FIG. 11) when compared with vehicle treated controls. β-catenin binding to cadherins to form stable cell-cell adhesions has been shown to be regulated by tyrosine phosphorylation of β-catenin. Therefore, we evaluated E-cadherin levels in cells treated with FGF19 by stripping and reprobing the tyrosine phosphorylation blot using anti-E-cadherin antibody. The results showed a substantial loss of E-cadherin binding to β-catenin in FGF19-treated cells. Similar results were obtained when E-cadherin was immunoprecipitated and immunoblot analysis was performed using anti-β-catenin antibody. The reduction in E-cadherin binding was inversely proportional to the increased tyrosine phosphorylation levels observed in FGF19-treated cells.

Example 14

Figure 12A:
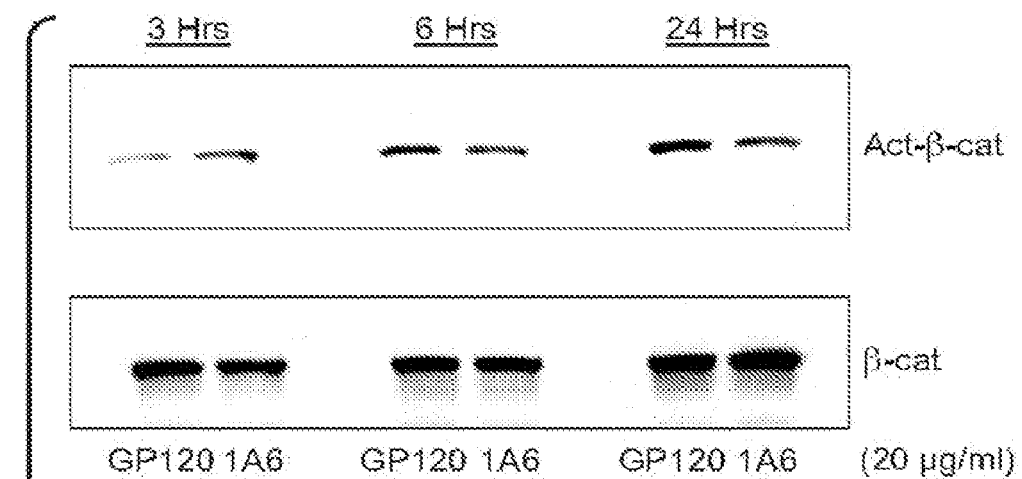
FIGS. 12A and B: Treatment with anti-FGF19 antibody reduced active-β-catenin levels in HCT116 cells. Cells were grown in the presence of serum and treated with either control (gp120) or anti-FGF19 mab 1A6 (both at 20 μg/ml) for varying time intervals. (A) Active-β-catenin ("act-β-cat") levels (N-terminally dephosphorylated β-catenin) were determined by immunoblotting. The same blot was stripped and reprobed for total β-catenin ("β-cat") levels. Representative blots from three separate experiments are shown. (B) Quantitative analysis of active-β-catenin levels at 24 hrs post-treatment as determined by calculating the ratio between the active-β-catenin and total β-catenin levels from three separate experiments (mean values±SE). β-actin levels were determined as a control.
Figure 12B:
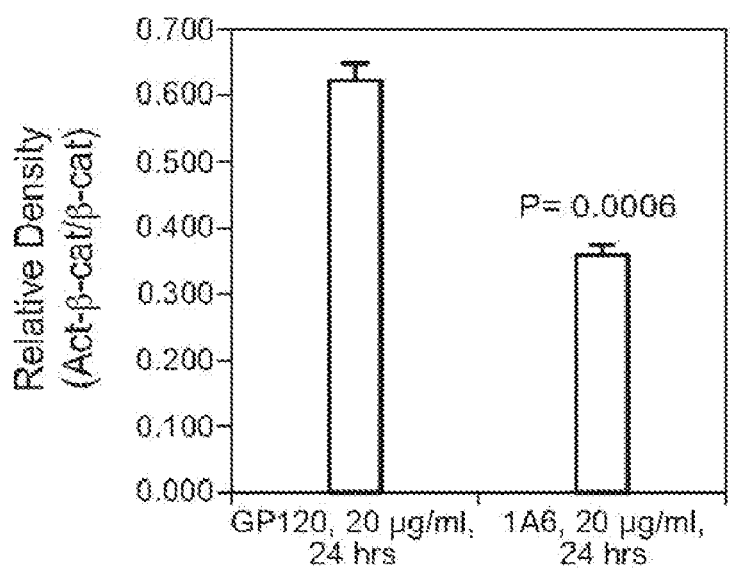

Inhibition of FGF19 Using Anti-FGF19 Antibody 1A6 Reduced Active-β-catenin Levels in HCT116 Cells Previous studies have established that Wnt regulated β-catenin degradation is essential for carcinogenesis (Polakis et al., Genes Dev 14:1837-51, 2000) and that Wnt signals are transmitted through N-terminally dephosphorylated β-catenin (Staal F J T et al, EMBO Reports 3:63-68, 2002). Using a specific antibody specific for β-catenin dephosphorylated at residues Ser37 and Thr41, we examined whether FGF19 or inhibition of FGF19 affects Wnt-signaling in HCT116 cells. Treatment of HCT116 cells with FGF19 did not affect active-β-catenin levels at any dose or time point, indicating that endogenous FGF19 activated β-catenin at saturated levels in an autocrine fashion. However, treatment of HCT116 cells with anti-FGF19 antibody 1A6 significantly reduced active-β-catenin levels at timepoints as early as 3 hrs following treatment, and sustained decreased active-β-catenin levels for up to 24 hrs (71.8±1.5% decrease vs gp120, p<0.001.) when compared with control antibody (gp120) treated cells (FIG. 12).

Example 15

Figure 13:
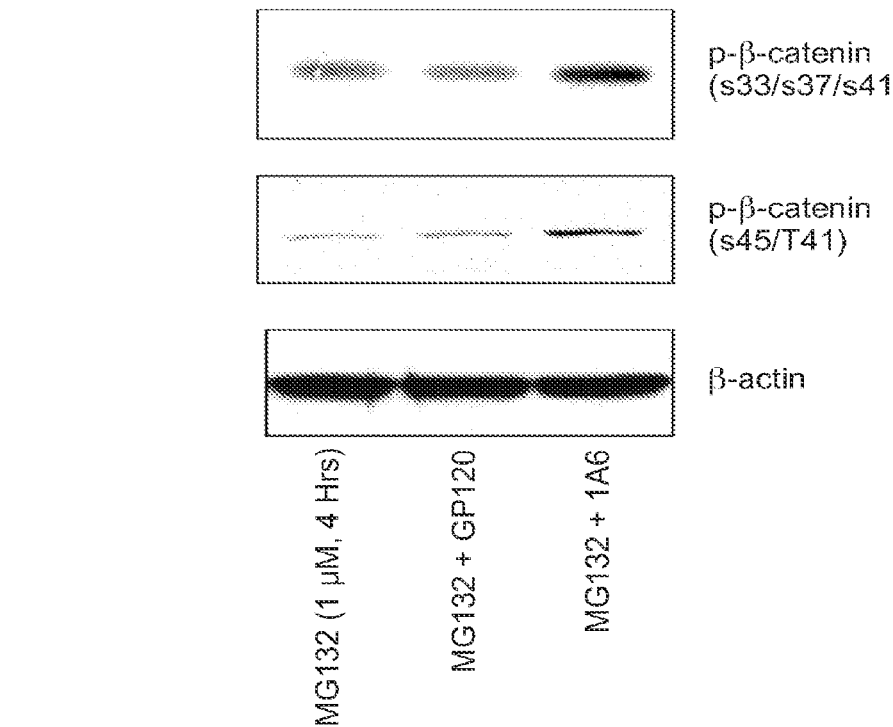
FIG. 13: Treatment with anti-FGF19 antibody induced phosphorylation on β-catenin amino acid residues Ser33/Ser37/Ser45 and Thr41 in HCT116 cells. Cells were grown in the presence of serum and treated with MG132 (1 μM) for 4 hrs followed by treatment with either control (gp120) or anti-FGF19 (1A6) antibody (both 20 μg/ml) for 24 hrs. β-catenin phosphorylation on Ser33/S37/S45 and Thr41 was analyzed by immunoblotting. The same blot was stripped and reprobed for total β-catenin. Representative blots from three separate experiments are shown. β-actin levels were determined as a control.

Treatment with Anti-FGF19 Antibody Induced Ser33/Ser37/Ser45 and Thr41 Phosphorylation Since FGF19 inhibition reduced active-β-catenin levels in HCT116 cells, we next evaluated whether treatment with anti-FGF19 antibody resulted in increased N-terminal Ser-Thr phosphorylation of β-catenin and thus targeted β-catenin for ubiquitination and proteasomic degradation. HCT116 cells pretreated with a proteasome inhibitor (MG132, 1 µM) for 4 hrs followed by treatment with anti-FGF19 monoclonal antibody 1A6 showed a significant increase in Ser33/Ser37 and Ser45/Thr41 phosphorylation when compared with proteasome inhibitor plus control antibody (gp120) treated cells (FIG. 13). Quantification of Ser33/37 phosphorylation (as determined by calculating the ratio between the total β-catenin protein and phosphorylated protein level) showed a 123.4±7% increase (p<0.05) in anti-FGF19 antibody 1A6-treated cells vs control anti-gp120 antibody-treated cells. Similarly Ser45/T41 phosphorylation was increased by 166.8±11% in anti-FGF19 monoclonal antibody 1A6-treated cells vs control anti-gp120 antibody treated cells (p<0.05).

Figure 14:
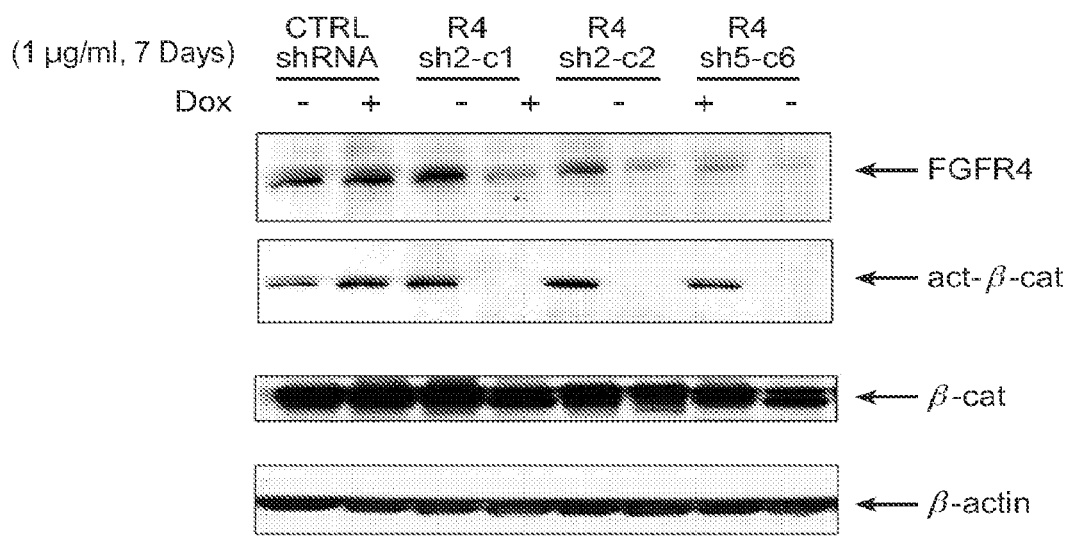
FIG. 14: Treatment with FGFR4-directed shRNA suppressed expression of FGFR4 protein and active-β-catenin in HCT116 cells. FGFR4 knockdown vectors were constructed by designing and cloning shRNA sequences into an retroviral inducible expression vector system. The cDNAs were transfected and stable cell lines expressing siRNA were generated in HCT116 cells using puromycin selection. Stable cell lines comprising control shRNA and FGFR4-directed shRNA were treated with or without doxycycline (Dox) and FGFR4 protein and active-β-catenin levels were determined by immunoprecipitation and immunoblotting. Representative blots from three separate experiments are shown.

Ser-Thr phosphorylation in the N-terminus of β-catenin was further analyzed using linear ion trap mass spectrometry. Signal intensities of non-phosphorylated β-catenin peptide were determined using linear ion trap mass spectrometry in cells pretreated with a proteasome inhibitor followed by treatment with either anti-FGF19 antibody 1A6 or control anti-gp20 antibody. The data was normalized to non-related peptides (containing all 4 phosphorylation sites) that showed no difference in signal intensities from the treated and untreated samples. The β-catenin peptide isolated from anti-FGF19 antibody 1A6-treated cells showed lower signal intensity when compared with β-catenin peptide isolated from control anti-gp120 antibody-treated cells (FIG. 14), clearly indicating increased phosphorylation on the N-terminus of β-catenin in anti-FGF19 monoclonal antibody 1A6-treated cells.

Example 16

Figure 15:
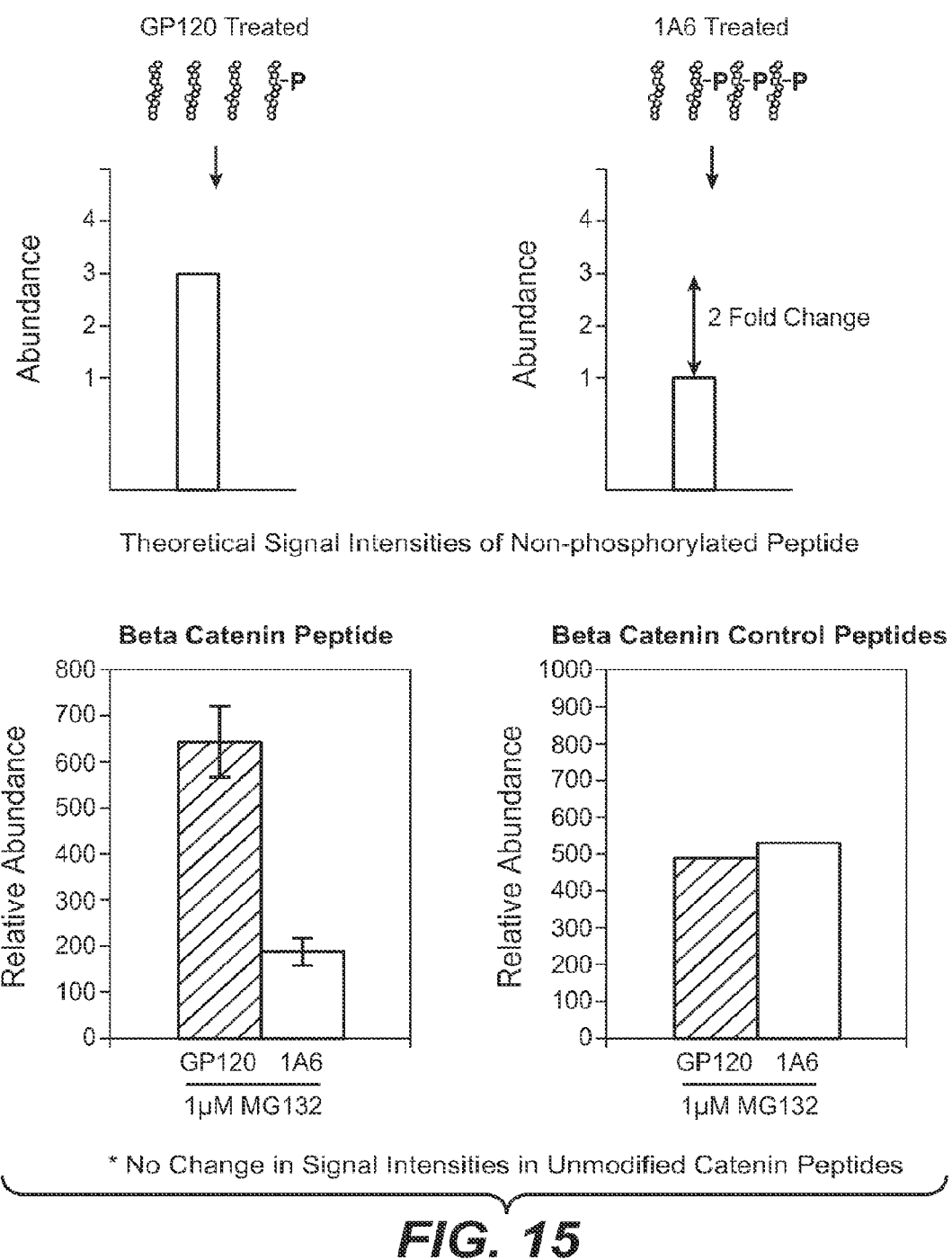
FIG. 15: Indirect quantification of N-terminal β-catenin phosphorylation levels using linear ion trap mass spectrometry. Data dependent tandem mass spectrometry on N-terminal peptide from immunoprecipitated β-catenin from cells treated with MG132 followed by control (gp120) or anti-FGF19 mab 1A6 was performed using a linear ion trap instrument as described in the Examples. Cross-correlation scores for each CID spectrum were generated and the relative abundance of peptides was determined. The data were normalized to the signal intensities of other non-related peptides that showed no difference in signal intensities from the treated and untreated samples.

Reduction of FGFR4 Expression Using shRNA Resulted in Reduced Active-β-catenin Levels To determine whether inhibition of the FGFR4 receptor would mimic the effect of FGF19 inhibition resulting from treatment with anti-FGF19 antibodies, stable cell lines expressing FGFR4-directed shRNA and control EGFP-directed shRNA were generated as described above. The stable cell line expressing FGFR4-directed shRNA showed effective knock-down of FGFR4 protein expression. Immunoblot analysis of cell lysates from a stable cell line expression FGFR4-directed shRNA showed almost complete reduction of active-β-catenin levels when compared with a control stable cell line expressing shRNA directed to EGFP (FIG. 15).

Example 17

Figure 16:
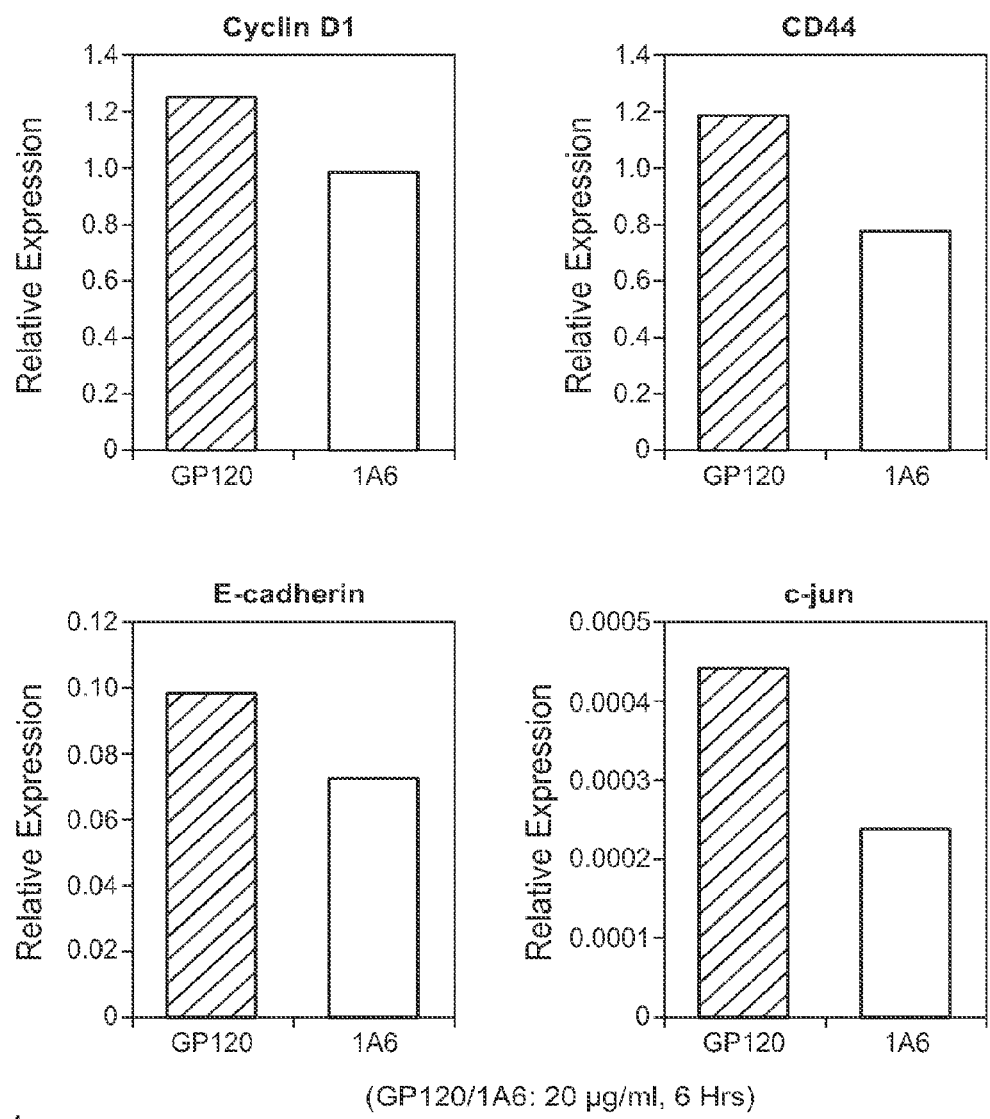
FIG. 16: Treatment with anti-FGF19 antibody reduced Wnt-target gene transcription levels in colon cancer cells. HCT116 cell were grown in the presence of serum and treated with either control (gp120) or 1A6 antibody (20 μm') for 6 hrs. β-catenin target gene (cyclin D1, CD44, E-cadherin, and c-jun) expression levels were analyzed by Taqman analysis. Analyses of data were performed using Sequence Detector 1.6.3 (PE Applied Biosystems) and results were normalized to RPL19 gene expression level.

Treatment with Anti-FGF19 Antibody Reduced Wnt-target Gene Transcription Levels in Colon Cancer Cells Wnt-target gene (cyclin D1, CD44, E-cad, c-jun) expression levels were determined using real-time PCR in anti-FGF19 antibody 1A6-treated HCT116 cells. As shown in FIG. 16, treatment with anti-FGF19 antibody 1A6 reduced cyclin D1, CD44, E-cad and c-jun mRNA expression levels at 6 hrs when compared with expression of those genes in control antibody (anti-gp120)-treated cells.

Partial Reference List

Anthony, P. P. (1979). J Toxicol Environ Health., 5, 301-13.
Bange, J., Prechtl, D., Cheburkin, Y., Specht, K., Harbeck, N., Schmitt, M., Knyazeva, T., Muller, S., Gartner, S., Sures, I., Wang, H., Imyanitov, E., Haring, H. U., Knayzev, P., Iacobelli, S., Holler, H. & Ullrich, A. (2002). Cancer Res, 62, 840-7.
Burgess, W. H. & Maciag, T. (1989). Annu Rev Biochem., 58, 575-606.
Cappellen, D., De Oliveira, C., Ricol, D., de Medina, S., Bourdin, J., Sastre-Garau, X., Chopin, D., Thiery, J. P. & Radvanyi, F. (1999). Nat Genet, 23, 18-20.
Chesi, M., Brents, L. A., Ely, S. A., Bais, C., Robbiani, D. F., Mesri, E. A., Kuehl, W. M. & Bergsagel, P. L. (2001). Blood, 97, 729-36.
Chesi, M., Nardini, E., Brents, L. A., Schrock, E., Ried, T., Kuehl, W. M. & Bergsagel, P. L. (1997). Nat. Genet., 16, 260-4.
Dorkin, T. J., Robinson, M. C., Marsh, C., Bjartell, A., Neal, D. E. & Leung, H. Y. (1999). Oncogene, 18, 2755-61.
Eswarakumar, V. P., Lax, I. & Schlessinger, J. (2005). Cytokine Growth Factor Rev., 16, 139-49. Epub 2005 Feb. 1.
Gowardhan, B., Douglas, D. A., Mathers, M. E., McKie, A. B., McCracken, S. R., Robson, C. N. & Leung, H. Y. (2005). Br J Cancer, 92, 320-7.
Harmer, N. J., Pellegrini, L., Chirgadze, D., Fernandez-Recio, J. & Blundell, T. L. (2004). Biochemistry, 43, 629-40.
Holcomb, I. N., Kabakoff, R. C., Chan, B., Baker, T. W., Gurney, A., Henzel, W., Nelson, C., Lowman, H. B., Wright, B. D., Skelton, N. J., Frantz, G. D., Tumas, D. B., Peale, F. V., Jr., Shelton, D. L. & Hebert, C.C. (2000). Embo J, 19, 4046-55.
Holt, J. A., Luo, G., Billin, A. N., Bisi, L, McNeill, Y. Y., Kozarsky, K. F., Donahee, M., Wang da, Y., Mansfield, T. A., Kliewer, S. A., Goodwin, B. & Jones, S. A. (2003). Genes Dev., 17, 1581-91. Epub 2003 Jun. 18.
Holzmann, K., Kohlhammer, H., Schwaenen, C., Wessendorf, S., Kestler, H. A., Schwoerer, A., Rau, B., Radlwimmer, B., Dohner, H., Lichter, P., Gress, T. & Bentz, M. (2004). Cancer Res, 64, 4428-33.
Huang, Y. Q., Li, J. J., Nicolaides, A., Zhang, W. G. & Friedman-Kien, A. E. (1993). Anticancer Res., 13, 887-90.
Jaakkola, S., Salmikangas, P., Nylund, S., Partanen, J., Armstrong, E., Pyrhonen, S., Lehtovirta, P. & Nevanlinna, H. (1993). Int J Cancer., 54, 378-82.
Jang, J. H., Shin, K. H. & Park, J. G. (2001). Cancer Res, 61, 3541-3.
Jang, J. H., Shin, K. H., Park, Y. J., Lee, R. J., McKeehan, W. L. & Park, J. G. (2000). Cancer Res, 60, 4049-52.
Jeffers, M., LaRochelle, W. J. & Lichenstein, H. S. (2002). Expert Opin Ther Targets, 6, 469-82.
Kan, M., Wu, X., Wang, F. & McKeehan, W. L. (1999). J Biol Chem, 274, 15947-52.
Kiuru-Kuhlefelt, S., Sarlomo-Rikala, M., Larramendy, M. L., Soderlund, M., Hedman, K., Miettinen, M. & Knuutila, S. (2000). Mod Pathol., 13, 433-7.
Kobayashi, M., Ikeda, K., Hosaka, T., Sezaki, H., Someya, T., Akuta, N., Suzuki, F., Suzuki, Y., Saitoh, S., Arase, Y. & Kumada, H. (2006). Cancer., 106, 636-47.
Krejci, P., Dvorakova, D., Krahulcova, E., Pachernik, J., Mayer, J., Hampl, A. & Dvorak, P. (2001). Leukemia, 15, 228-37.
Lee, F. T., Jr., Chosy, S. G., Naidu, S. G., Goldfarb, S., Weichert, J. P., Bakan, D. A., Kuhlman, J. E., Tambeaux, R. H. & Sproat, I. A. (1997). Radiology., 203, 465-70.
Liscia, D. S., Merlo, G. R., Garrett, C., French, D., Mariani-Costantini, R. & Callahan, R. (1989). Oncogene, 4, 1219-24.
Marsh, S. K., Bansal, G. S., Zammit, C., Barnard, R., Coope, R., Roberts-Clarke, D., Gomm, J. J., Coombes, R. C. & Johnston, C. L. (1999). Oncogene, 18, 1053-60.

Mattila, M. M., Ruohola, J. K., Valve, E. M., Tasanen, M. J., Seppanen, J. A. & Harkonen, P. L. (2001). Oncogene, 20, 2791-804.

Mauad, T. H., van Nieuwkerk, C. M., Dingemans, K. P., Smit, J. J., Schinkel, A. H., Notenboom, R. G., van den Bergh Weerman, M. A., Verkruisen, R. P., Groen, A. K., Oude Elferink, R. P. & et al. (1994). Am J Pathol, 145, 1237-45.

Morimoto, Y., Ozaki, T., Ouchida, M., Umehara, N., Ohata, N., Yoshida, A., Shimizu, K. & Inoue, H. (2003). Cancer, 98, 2245-50.

Nicholes, K., Guillet, S., Tomlinson, E., Hillan, K., Wright, B., Frantz, G. D., Pham, T. A., Dillard-Telm, L., Tsai, S. P., Stephan, J. P., Stinson, J., Stewart, T. & French, D. M. (2002). Am J Pathol, 160, 2295-307.

Ornitz, D. M. & Itoh, N. (2001). Genome Biol, 2, REVIEWS3005.

Ornitz, D. M., Xu, J., Colvin, J. S., McEwen, D. G., MacArthur, C. A., Coulier, F., Gao, G. & Goldfarb, M. (1996). J Biol. Chem., 271, 15292-7.

Plotnikov, A. N., Schlessinger, J., Hubbard, S. R. & Mohammadi, M. (1999). Cell., 98, 641-50.

Popovici, C., Zhang, B., Gregoire, M. J., Jonveaux, P., Lafage-Pochitaloff, M., Birnbaum, D. & Pebusque, M. J. (1999). Blood., 93, 1381-9.

Powers, C. J., McLeskey, S. W. & Wellstein, A. (2000). Endocr Relat Cancer, 7, 165-97.

Qian, Z. R., Sano, T., Asa, S. L., Yamada, S., Horiguchi, H., Tashiro, T., Li, C. C., Hirokawa, M., Kovacs, K. & Ezzat, S. (2004). J Clin Endocrinol Metab., 89, 1904-11.

Richelda, R., Ronchetti, D., Baldini, L., Cro, L., Viggiano, L., Marzella, R., Rocchi, M., Otsuki, T., Lombardi, L., Maiolo, A. T. & Neri, A. (1997). Blood., 90, 4062-70.

Ruohola, J. K., Viitanen, T. P., Valve, E. M., Seppanen, J. A., Loponen, N. T., Keskitalo, J. J., Lakkakorpi, P. T. & Harkonen, P. L. (2001). Cancer Res, 61, 4229-37.

Schlessinger, J. (2004). Science., 306, 1506-7.

Shimokawa, T., Furukawa, Y., Sakai, M., Li, M., Miwa, N., Lin, Y. M. & Nakamura, Y. (2003). Cancer Res, 63, 6116-20.

Sleeman, M., Fraser, J., McDonald, M., Yuan, S., White, D., Grandison, P., Kumble, K., Watson, J. D. & Murison, J. G. (2001). Gene., 271, 171-82.

Streit, S., Bange, J., Fichtner, A., Ihrler, S., Issing, W. & Ullrich, A. (2004). Int J Cancer, 111, 213-7.

Wang, J., Stockton, D. W. & Ittmann, M. (2004). Clin Cancer Res., 10, 6169-78.

Weichert, J. P., Longino, M. A., Spigarelli, M. G., Lee, F. T., Jr., Schwendner, S. W. & Counsell, R. E. (1996). Acad Radiol., 3, 412-7.

Xiao, S., Nalabolu, S. R., Aster, J. C., Ma, J., Abruzzo, L., Jaffe, E. S., Stone, R., Weissman, S. M., Hudson, T. J. & Fletcher, J. A. (1998). Nat. Genet., 18, 84-7.

Xie, M. H., Holcomb, I., Deuel, B., Dowd, P., Huang, A., Vagts, A., Foster, J., Liang, J., Brush, J., Gu, Q., Hillan, K., Goddard, A. & Gurney, A. L. (1999). Cytokine, 11, 729-35.

Yamada, S. M., Yamada, S., Hayashi, Y., Takahashi, H., Teramoto, A. & Matsumoto, K. (2002). Neurol Res., 24, 244-8.

Yu, C., Wang, F., Jin, C., Huang, X. & McKeehan, W. L. (2005). J Biol. Chem., 280, 17707-14. Epub 2005 Mar. 4.

Zaharieva, B. M., Simon, R., Diener, P. A., Ackermann, D., Maurer, R., Alund, G., Knonagel, H., Rist, M., Wilber, K., Hering, F., Schonenberger, A., Flury, R., Jager, P., Fehr, J. L., Mihatsch, M. J., Gasser, T., Sauter, G. & Toncheva, D. I. (2003). J Pathol, 201, 603-8.

Although the foregoing invention has been described in some detail by way of illustration and example for purposes of clarity of understanding, the descriptions and examples should not be construed as limiting the scope of the invention.

What is claimed is:

1. A method of inhibiting relapse tumor growth, the method comprising administering an effective amount of an anti-FGF19 antibody to an individual in need of such treatment, wherein the antibody comprises:
   (a) a light chain comprising (i) HVR (hypervariable region)-L1 comprising SEQ ID NO:1; (ii) HVR-L2 comprising amino acids 50-56 of SEQ ID NO:4; and (iii) HVR-L3 comprising SEQ ID NO:3; and
   (b) a heavy chain comprising (i) HVR-H1 comprising SEQ ID NO:5; (ii) HVR-H2 comprising-SEQ ID NO:6; and (iii) HVR-H3 comprising SEQ ID NO:7;
   wherein the relapse tumor growth is a hepatocellular carcinoma tumor growth or colorectal cancer tumor growth.

2. A method of inhibiting relapse tumor growth, the method comprising administering an effective amount of an anti-FGF19 antibody to an individual in need of such treatment, wherein the antibody competes for binding to human FGF19 with an antibody of claim 1, wherein the relapse tumor growth is a hepatocellular carcinoma tumor growth or colorectal cancer tumor growth.

3. The method of inhibiting relapse tumor growth of claim 2, wherein the relapse tumor growth is a hepatocellular carcinoma tumor growth.

4. The method of inhibiting relapse tumor growth of claim 2, wherein the relapse tumor growth is a colorectal cancer relapse tumor growth.

5. The method of inhibiting relapse tumor growth of claim 2, further comprising administering to the subject an effective amount of a second medicament, wherein the anti-FGF19 antibody is a first medicament.

6. The method of inhibiting relapse tumor growth of claim 1, wherein a full length IgG form of the antibody specifically binds human FGF19 with a $k_{on}$ of $6 \times 10^5$ $(M^{-1}s^{-1})$ or better.

7. The method of inhibiting relapse tumor growth of claim 1, wherein a full length IgG form of the antibody specifically binds human FGF19 with a $k_{off}$ of $5 \times 10^{-6}$ $(s^{-1})$ or better.

8. The method of inhibiting relapse tumor growth of claim 1, wherein a full length IgG form of the antibody specifically binds human FGF19 with a binding affinity of 40 pM or better.

9. The method of treating inhibiting relapse tumor growth of claim 1, wherein the full length IgG form of the antibody specifically binds human FGF19 with a binding affinity of 20 pM or better.

10. The method of inhibiting relapse tumor growth of claim 1, wherein the antibody inhibits FGF19 promoted cell migration.

11. The method of inhibiting relapse tumor growth of claim 1, wherein the antibody inhibits FGF19-induced repression of CYP7α1 gene in a cell.

12. The method of inhibiting relapse tumor growth of claim 1, wherein the antibody inhibits FGF19-induced phosphorylation of one or more of FGFR4, MAPK, FRS and ERK2.

13. The method of inhibiting relapse tumor growth of claim 1, wherein the antibody inhibits Wnt pathway activation in a cell.

14. The method of inhibiting relapse tumor growth of claim 13, wherein Wnt pathway activation is characterized by one or more of tyrosine phosphorylation of β-catenin, expression of Wnt target genes, and E-cadherin binding to β-catenin.

15. The method of inhibiting relapse tumor growth of claim 1, wherein the antibody is a monoclonal antibody.

16. The method of inhibiting relapse tumor growth of claim 1, wherein the antibody is selected from the group consisting of a chimeric antibody, a humanized antibody, an affinity matured antibody, a human antibody, and a bispecific antibody.

17. The method of inhibiting relapse tumor growth of claim 1, wherein the antibody is an antibody fragment.

18. The method of inhibiting relapse tumor growth claim 1, wherein the antibody is an immunoconjugate.

* * * * *